US007173164B2

(12) United States Patent
Brugliera et al.

(10) Patent No.: US 7,173,164 B2
(45) Date of Patent: Feb. 6, 2007

(54) PLANT ANTHOCYANIDIN RUTINOSIDE AROMATIC ACYL TRANSFERASES

(75) Inventors: Filippa Brugliera, Preston (AU); Ronald Koes, Amsterdam (NL)

(73) Assignee: International Flower Developments Pty. Ltd., Victoria (AU)

( * ) Notice: Subject to any disclaimer, the term of this patent is extended or adjusted under 35 U.S.C. 154(b) by 489 days.

(21) Appl. No.: 10/259,549

(22) Filed: Sep. 27, 2002

(65) Prior Publication Data
US 2003/0172400 A1   Sep. 11, 2003

Related U.S. Application Data

(63) Continuation of application No. PCT/AU01/00358, filed on Mar. 30, 2001.

(30) Foreign Application Priority Data
Mar. 31, 2000 (AU) ..................... PQ6598

(51) Int. Cl.
C12N 15/29 (2006.01)
C12N 15/52 (2006.01)
C12N 15/82 (2006.01)
A01H 5/00 (2006.01)
A01H 5/10 (2006.01)

(52) U.S. Cl. ...................... 800/282; 800/298; 800/323; 800/323.1; 536/23.1; 536/23.2; 536/23.6; 435/320.1; 435/419

(58) Field of Classification Search ............... 536/23.1, 536/23.2, 23.6; 435/419, 320.1; 800/278, 800/282, 298, 323, 323.1
See application file for complete search history.

(56) References Cited

FOREIGN PATENT DOCUMENTS

CA        2213082       8/1996
WO        WO 00/32789   6/2000

OTHER PUBLICATIONS

Broun P. et al. Science vol. 282; Nov. 13, 1998, pp. 1315-1317.*
Branch et al. TIBS, vol. 23, Feb. 1998, pp. 45-50.*
Waterhouse P. et al., Trends in Plant Sciences, Nov. 1999, vol. 4, No. 11 pp. 452-457.*
Brouillard, Raymond, et al., "Flavonoids and Flower Colour", In: *The Flavonoids: advances in research since 1986 by J. B. Harborne*, London ; New York : Chapman & Hall, ; ISBN: 0412480700 (alk. paper),(1993),565-588.
Brugliera, Filippa, et al., "Isolation and characterization of a cDNA clone corresponding to the Rt locus of *Petunia hybrida*", *The Plant Journal*, vol. 5, No. 1, (1994),pp. 81-92.
Brugliera, Filippa, et al., "Isolation and characterization of a flavonoid 3'-hydroxylase cDNA clone corresponding to the Ht1 locus of *Petunia hybrida*", *The Plant Journal*, vol. 19, No. 4, (1999),pp. 441-451.

Dangles, Olivier, et al., "Anthocyanin Intramolecular Copigment Effect", *Phytochemistry*, vol. 34, No. 1, (1993),pp. 119-124.
Fujiwara, Hiroyuki, et al., "cDNA cloning, gene expression and subcellular localization of anthocyanin 5-aromatic acyltransferase from *Gentiana triflora*", *The Plant Journal*, vol. 16, No. 4, (1998),pp. 421-431.
Goto, Toshio, et al., "PMR Spectra of Natural Acylated Anthocyanins Determination of Stereostructure of Awobanin, Shisonin and Violanin", *Tetrahedron Letters* No. 27, (1978),pp. 2413-2416.
Griesbach, R J., et al., "*Petunia hybrida* Anthocyanins Acylated With Caffeic Acid", *Phytochemistry*, vol. 30, No. 5, (1991), 1729-1731.
Holton, Timothy A., et al., "Cloning and expression of cytochrome P450 genes controlling flower colour", *Nature*, vol. 366, (1993),pp. 276-279.
Holton, Timothy A., et al., "Genetics and Biochemistry of Anthocyanin Biosynthesis", *The Plant Cell*, vol. 7, (1995),pp. 1071-1083.
Hopp, Wolfgang, et al., "The uptake of acylated anthocyanin into isolated vacuoles from a cell suspension culture of *Daucus carota*", *Planta*, vol. 170, (1987),pp. 74-85.
Kondo, Tadao, et al., "Structure of Lobelinin A and B, Novel Anthocyanins Acylated with Three and Four Different Organic Acids, Respectively", *Tetrahedron Letters*, vol. 30, No. 44, (1989),pp. 6055-6058.
Kroon, Johan, et al., "Cloning and structural analysis of the anthocyanin pigmentation locus Rt of *Petunia hybrida*: characterization of insertion sequences in two mutant alleles", *The Plant Journal*, vol. 5, No. 1, (1994),pp. 69-80.
Lu, Ting S., et al., "Acylated Pelargonidin Glycosides In the Red-Purple Flowers of Pharbitis NIL", *Phytochemistry*, vol. 31, No. 1, (1992), 289-295.
St-Pierre, Benoit, et al., "Evolution of Acyltransferase Genes: Origin and Diversification of the BAHD Superfamily of Acyltransferases Involved in Secondary Metabolism", *In: Evolution of metabolic pathways by John T. Romeo*, Amsterdam ; New York ; Pergamon, ; ISBN: 0080438601,(2000),285-315.
Strack, Dieter, et al., "The Anthocyanins", *In: The Flavonoids: Advances in research since 1986 by JP Harborne*, Chapman & Hall, London—ISBN 0412480700, 1-22.

(Continued)

Primary Examiner—Russell P. Kallis
(74) Attorney, Agent, or Firm—Schwegman, Lundberg, Woessner & Kluth P.A.

(57) ABSTRACT

The present invention relates generally to a genetic sequence encoding a polypeptide having aromatic acyl group transfer activity and the use of the genetic sequence and/or its corresponding polypeptide thereof. More particularly, the present invention provides a genetic sequence encoding a polypeptide having aromatic acyl group transfer activity derived from *Petunia*, *Nierembergia* and *Viola* spp. Even more particularly, the present invention relates to a genetic sequence encoding a polypeptide having aromatic acyl group transferase activity to anthocyanidin-rutinoside. The present invention also provides a genetic sequence encoding a polypeptide having aromatic acyl group transferase activity to anthocyanidin 3-O-rutinoside. The instant invention further relates to antisense and sense molecules corresponding to all or part of the subject genetic sequence as well as genetically modified plants as well as cut flowers, parts and reproductive tissue from such plants.

27 Claims, 14 Drawing Sheets

OTHER PUBLICATIONS

Yoshida, Kumi, et al., "Intramolecular Stacking Conformation of Gentiodelphin, a Diacylated Anthocyanin from Gentiana Makinoi", *Tetrahedron*, vol. 48, No. 21, (1992),4313-4326.

Teusch, Monika, et al., "Genetic Control of Hydrozycinnamoyl-coenzyme A: Anthocyanidin 3-Glycoside-Hydroxycinnamoyltransferase from petals of *Matthiola incana*", *Phytochemistry*, vol. 26, No. 4, (1987),991-994.

Fujiwara, Hiroyuki.,et al.,"Anthocyanin 5-aromatic acyltransferase from *Gentiana triflora* Purification, chracterization and its role in anthocyanin biosynthesis", *Eur. J. Biochem 249*, FEBS 1997,(1997),45-51.

Fujiwara, Hiroyuki.,et al., "Purification and chracterization of anthocyanin 3-aromatic acyltransferase from *Perilla frutescens*", *Plant Science 1998*(1998),87-94.

Kamsteeg, John.,et al., "Identification, Properties and Genetic Control of Hydroxycinnamoyl-coenzyme A: Anthocyanidin 3-rhamnosyl (1-6) glucoside, 4"-hydroxycinnamoyl Transferase Isolated from Petals of *Silene dioica*", *Biochem. Physiol. Pflanzen 175*, (1980),403-411.

Yonekura-Sakakibara, Keiko.,et al., "Molecular and Biochemical Chracterization of a Novel Hydroxycinnamoyl-CoA: Anthocyanin 3-O-Glucoside-6"-O-Acyltransferase from *Perilla frutescens*", *Plant Cell Physiol. 41(4)*, (2000),495-502.

\* cited by examiner

Replicon: pBluescript SK II + vector 2.95kb

Insert: difC cDNA ~1.0kb

Replicon: pBluescript SK II + 2.95kb
Insert: C9 cDNA ~1.43kb

Replicon: pYE22m Asp718/EcoRI

Insert source: 1.8kb Asp718/EcoRI fragment from pCGP1904

Replicon: pCGP40 SacI/Asp718 vector (pCGN7334 based)

Insert source: 1.4kb SacI/Asp718 *C9* fragment from pCGP1904

Replicon: pWTT2132 SmaI

Insert: 3.3kb BgI II (blunted) fragment from pCGP1909

Replicon: pBluescript SK II + vector 2.95kb

Insert: NAR-AT cDNA ~1.4kb

Replicon: pCR 2.1 3.9kb
Insert: BPAR-AT2 ~1.2kb fragment

Replicon: pCR 2.1 3.9kb
Insert: LBAR-AT3 ~1.2kb fragment

Replicon: pCR 2.1 3.9kb
Insert: LBAR-AT17 ~1.2kb fragment

SEQUENCE LISTING

<160> NUMBER OF SEQ ID NOS: 31

<210> SEQ ID NO 1
<211> LENGTH: 1415
<212> TYPE: DNA
<213> ORGANISM: petunia

<400> SEQUENCE: 1

| | | | | | |
|---|---|---|---|---|---|
| gtttctagct | ttagccaaac | aagagataca | ttatgaatca | agtttgaat | ggttcttgtt | 60 |
| ttcaaattga | aatcttgaat | gaaaaactca | taaaaccatc | attaccaact | cctaatcacc | 120 |
| ttaattgtta | caagttatct | ttctttgatc | aacttgctcc | taattttgct | gtaccccttc | 180 |
| tttactttta | ccctacggtt | ccacctgaaa | aatccaactt | gcaaagtgct | gaatcaattc | 240 |
| atgcacaact | acaaaactca | ttatctgaga | cactaacaaa | attttatcca | cttgctggaa | 300 |
| gattttctga | agatggtact | tcaattgaat | gtcatgatca | agggtcatt | tacttagaag | 360 |
| caaaagtgaa | tggacaattg | aatgagttcc | tagacaatgc | atacaagaat | agtgatcttg | 420 |
| ttaaaatatt | tgtaccacct | ataagaatca | ggacagctga | attgccttat | agaccaatga | 480 |
| tggcaataca | agctacaatg | tttgaatgtg | gtggcttagc | tctagcagta | caaattgtcc | 540 |
| atacattagg | tgatggattt | tccggctgcg | cggtgaccga | tgaatgggct | aaggttagta | 600 |
| gaatggagaa | gagtagtaat | gctagaactt | tacaatttcg | ttctgatttg | gctgatgtat | 660 |
| ttccacctaa | gaaaaatatt | tttgacatgg | ttaagaaagg | taggcctaga | ggatatgaaa | 720 |
| tgaaaattgt | tactaggatc | ttcatgtttg | atgaagttgc | aatatcaaag | ttaaaggaga | 780 |
| atgtgaacaa | gtcattgagt | tattcatcaa | gagttgaagt | tgtgacagca | ctcatttgga | 840 |
| gaagtcttat | gcgagtggtg | aggtttaggg | ttggtcacaa | taggccatcc | atgctacaat | 900 |
| ttgccatgaa | tttacgtgga | agagcatctc | caaaactagt | aggtgaagat | cagaacttat | 960 |
| ttggcaattt | ctaccttgac | attccaataa | aatgtgtgcc | ttcacatgac | aatcaagatt | 1020 |
| tggaattgca | tgaaattgtg | accttaatta | gagacacaaa | gaacaaaatt | ctatctaaaa | 1080 |
| ttgccaatgc | ttcaagtgaa | gagattatct | cattagtgat | tgagtccaca | aataaaatac | 1140 |
| gagaagggta | taatgatgat | gaaattgacc | tttatcctac | ttcaagttta | tgtagatttc | 1200 |
| cactaaatga | gtgtgatttt | ggctgggcta | aaccaacttg | ggtgagcaga | attaatgttc | 1260 |
| catttcaaat | gttcttcttg | atggattcaa | aaactggaat | tgaagttaga | gtttgcttga | 1320 |
| atgaagatga | tatgttaaaa | cttgaaactg | atattgacat | tgtggagttt | agttctatgc | 1380 |
| caaaatagag | aagaattaag | tggaaaaaaa | aaaaa | | | 1415 |

<210> SEQ ID NO 2
<211> LENGTH: 457
<212> TYPE: PRT
<213> ORGANISM: petunia

<400> SEQUENCE: 2

Pro Asn Lys Arg Tyr Ile Met Asn Gln Ser Leu Asn Gly Ser Cys Phe
1               5                   10                  15

Gln Ile Glu Ile Leu Asn Glu Lys Leu Ile Lys Pro Ser Leu Pro Thr
            20                  25                  30

Pro Asn His Leu Asn Cys Tyr Lys Leu Ser Phe Phe Asp Gln Leu Ala
        35                  40                  45

Pro Asn Phe Ala Val Pro Leu Leu Tyr Phe Tyr Pro Thr Val Pro Pro
    50                  55                  60

-continued

```
Glu Lys Ser Asn Leu Gln Ser Ala Glu Ser Ile His Ala Gln Leu Gln
 65                  70                  75                  80

Asn Ser Leu Ser Glu Thr Leu Thr Lys Phe Tyr Pro Leu Ala Gly Arg
             85                  90                  95

Phe Ser Glu Asp Gly Thr Ser Ile Glu Cys His Asp Gln Gly Val Ile
            100                 105                 110

Tyr Leu Glu Ala Lys Val Asn Gly Gln Leu Asn Glu Phe Leu Asp Asn
        115                 120                 125

Ala Tyr Lys Asn Ser Asp Leu Val Lys Ile Phe Val Pro Pro Ile Arg
    130                 135                 140

Ile Arg Thr Ala Glu Leu Pro Tyr Arg Pro Met Met Ala Ile Gln Ala
145                 150                 155                 160

Thr Met Phe Glu Cys Gly Gly Leu Ala Leu Ala Val Gln Ile Val His
                165                 170                 175

Thr Leu Gly Asp Gly Phe Ser Gly Cys Ala Val Thr Asp Glu Trp Ala
            180                 185                 190

Lys Val Ser Arg Met Glu Lys Ser Asn Ala Arg Thr Leu Gln Phe
        195                 200                 205

Arg Ser Asp Leu Ala Asp Val Phe Pro Pro Lys Lys Asn Ile Phe Asp
    210                 215                 220

Met Val Lys Lys Gly Arg Pro Arg Gly Tyr Glu Met Lys Ile Val Thr
225                 230                 235                 240

Arg Ile Phe Met Phe Asp Glu Val Ala Ile Ser Lys Leu Lys Glu Asn
                245                 250                 255

Val Asn Lys Ser Leu Ser Tyr Ser Ser Arg Val Glu Val Thr Ala
            260                 265                 270

Leu Ile Trp Arg Ser Leu Met Arg Val Val Arg Phe Arg Val Gly His
        275                 280                 285

Asn Arg Pro Ser Met Leu Gln Phe Ala Met Asn Leu Arg Gly Arg Ala
    290                 295                 300

Ser Pro Lys Leu Val Gly Glu Asp Gln Asn Leu Phe Gly Asn Phe Tyr
305                 310                 315                 320

Leu Asp Ile Pro Ile Lys Cys Val Pro Ser His Asp Asn Gln Asp Leu
                325                 330                 335

Glu Leu His Glu Ile Val Thr Leu Ile Arg Asp Thr Lys Asn Lys Ile
            340                 345                 350

Leu Ser Lys Ile Ala Asn Ala Ser Glu Glu Ile Ile Ser Leu Val
        355                 360                 365

Ile Glu Ser Thr Asn Lys Ile Arg Glu Gly Tyr Asn Asp Asp Glu Ile
370                 375                 380

Asp Leu Tyr Pro Thr Ser Ser Leu Cys Arg Phe Pro Leu Asn Glu Cys
385                 390                 395                 400

Asp Phe Gly Trp Ala Lys Pro Thr Trp Val Ser Arg Ile Asn Val Pro
                405                 410                 415

Phe Gln Met Phe Phe Leu Met Asp Ser Lys Thr Gly Ile Glu Val Arg
            420                 425                 430

Val Cys Leu Asn Glu Asp Asp Met Leu Lys Leu Glu Thr Asp Ile Asp
        435                 440                 445

Ile Val Glu Phe Ser Ser Met Pro Lys
        450                 455
```

<210> SEQ ID NO 3
<211> LENGTH: 45

```
<212> TYPE: DNA
<213> ORGANISM: Artificial Sequence
<220> FEATURE:
<223> OTHER INFORMATION: A primer

<400> SEQUENCE: 3
gagagagaga gagagagaga tctcgagttt tttttttttt ttttt            45

<210> SEQ ID NO 4
<211> LENGTH: 25
<212> TYPE: DNA
<213> ORGANISM: Artificial Sequence
<220> FEATURE:
<223> OTHER INFORMATION: A primer

<400> SEQUENCE: 4
gagatacacc atggatcaaa gtttg                                  25

<210> SEQ ID NO 5
<211> LENGTH: 29
<212> TYPE: DNA
<213> ORGANISM: Artificial Sequence
<220> FEATURE:
<223> OTHER INFORMATION: A primer

<400> SEQUENCE: 5
cgggatcctt ttggcataga actaaactc                              29

<210> SEQ ID NO 6
<211> LENGTH: 1728
<212> TYPE: DNA
<213> ORGANISM: Nierembergia

<400> SEQUENCE: 6
gttttcaact ttagtaaaaa ttaaaaaaaa atttacaata tgagtcaaat taccaagcaa    60
aatttgaatg gttcttcttg tattgacatt gaaatcttga atgaaaaact catcaaacca   120
tcactaccaa ctccaaatca ccttcattct tacaagttat gtttctttga tcaacttgct   180
cctaattttg ctgtaccct  tctttacttt taccttccg ccctccaga aaaccggag    240
```
(Note: the above line near 240 shows: cctaattttg ctgtacccct tctttacttt taccttccg cccctccaga aaaaccggag)
```
ctacaaagtg ctgaatcgat ccatacacaa ctacaaaact cgttatccga gacgttgacg   300
aaatttatc cacttgccgg taggttgtca caagatggta catcaattga gtgtcatgac   360
caagggggtaa tttacttaga agcaaaagta aattgtcaat taaatgaatt cttagacaat   420
gcttataaga atagtgatct tgttaaactc tttgtaccac caataagaat taggacagct   480
gaattaccta atagaccatt ccttgcaatt caagcaacaa tatttcaatg tggtggatta   540
ggtttagctg tacaaatggt tcatacgata ggtgatggat tttcggggttg cgcgttaacg   600
gatgaatggt gtaaggttag tagaatggag aaggaaaatg ttagaaattt acaatttcgt   660
tgtgatttgg ctaatgtttt tcaacctaaa gataatgttt ttgagatgat taagaaaggt   720
agacctagag gatatgagat gaaaattgtt acaaggattt tcatgtttga tgaagttgca   780
atatctaagt tgaaagaaaa tgtgaacaag tcttgaaat attcttcaag agttgaagtt   840
gtcacatcac ttgtttggag aagtcttatg aaagttgtca agttaagaca tggtaaaaat   900
aggccatcca tgttgcaatt tgctatgaat tttcgtggaa gagctgatcc aaaacttgta   960
ggggaagatc aaaactttt ttggaaacttc taccttgaca taccaataaa atgtataccct  1020
tcacatgaca atggagattt agaattacat gaaattgtga cattaattag agatgaaaag  1080
aacaaaacat tatcaaaaat tggtaatgct tcaagtgaag agatattctc attggtaatt  1140
```

-continued

```
gattcaataa atcaaataaa agaagggtat aatgatgatg aaattgacct ttatccaact    1200
tcaagtttat gtagatttcc attgaatgaa tctgattttg gttgggctaa accaatttgg    1260
gtaagtaggg taaatgtacc atttcaaatg ttttctcttga tggattcaaa aaatggaatt   1320
gaagttagag tttgcttgaa tgaagatgat atgattcaac ttgaaagtga tgatgatatt    1380
gtggagttca gttatgtgcc caaatagttt tagaggaaac agcctcttac agaaatgcag    1440
gtagggttat ctttgtggtc gagctctctt tcagactccg cacatagcgg gagcatagtg    1500
caccgggatg ccctttttac ttagttctaa gcattaacta agtgagcttg attttctttt   1560
tttttctgtt tttgtacttc aatcttcttg ttgttgtctc tctacctcca cgagaggtag    1620
ggtaaggttt gtgtaatctt catgttgttg ttgtaatctt ctcgttgttt aacgggcttt    1680
ctgttataca ttattacttt attttgttt aaaaaaaaaa aaaaaaaa                  1728
```

<210> SEQ ID NO 7
<211> LENGTH: 460
<212> TYPE: PRT
<213> ORGANISM: Nierembergia

<400> SEQUENCE: 7

```
Lys Lys Ile Tyr Asn Met Ser Gln Ile Thr Lys Gln Asn Leu Asn Gly
1               5                   10                  15

Ser Ser Cys Ile Asp Ile Glu Ile Leu Asn Glu Lys Leu Ile Lys Pro
            20                  25                  30

Ser Leu Pro Thr Pro Asn His Leu His Ser Tyr Lys Leu Cys Phe Phe
        35                  40                  45

Asp Gln Leu Ala Pro Asn Phe Ala Val Pro Leu Leu Tyr Phe Tyr Pro
    50                  55                  60

Ser Ala Pro Pro Glu Lys Pro Glu Leu Gln Ser Ala Glu Ser Ile His
65                  70                  75                  80

Thr Gln Leu Gln Asn Ser Leu Ser Glu Thr Leu Thr Lys Phe Tyr Pro
                85                  90                  95

Leu Ala Gly Arg Leu Ser Gln Asp Gly Thr Ser Ile Glu Cys His Asp
            100                 105                 110

Gln Gly Val Ile Tyr Leu Glu Ala Lys Val Asn Cys Gln Leu Asn Glu
        115                 120                 125

Phe Leu Asp Asn Ala Tyr Lys Asn Ser Asp Leu Val Lys Leu Phe Val
    130                 135                 140

Pro Pro Ile Arg Ile Arg Thr Ala Glu Leu Pro Asn Arg Pro Phe Leu
145                 150                 155                 160

Ala Ile Gln Ala Thr Ile Phe Gln Cys Gly Gly Leu Gly Leu Ala Val
                165                 170                 175

Gln Met Val His Thr Ile Gly Asp Gly Phe Ser Gly Cys Ala Leu Thr
            180                 185                 190

Asp Glu Trp Cys Lys Val Ser Arg Met Glu Lys Glu Asn Val Arg Asn
        195                 200                 205

Leu Gln Phe Arg Cys Asp Leu Ala Asn Val Phe Gln Pro Lys Asp Asn
    210                 215                 220

Val Phe Glu Met Ile Lys Lys Gly Arg Pro Arg Gly Tyr Glu Met Lys
225                 230                 235                 240

Ile Val Thr Arg Ile Phe Met Phe Asp Glu Val Ala Ile Ser Lys Leu
                245                 250                 255

Lys Glu Asn Val Asn Lys Ser Leu Lys Tyr Ser Ser Arg Val Glu Val
            260                 265                 270
```

```
Val Thr Ser Leu Val Trp Arg Ser Leu Met Lys Val Val Lys Leu Arg
        275                 280                 285

His Gly Lys Asn Arg Pro Ser Met Leu Gln Phe Ala Met Asn Phe Arg
        290                 295                 300

Gly Arg Ala Asp Pro Lys Leu Val Gly Glu Asp Gln Asn Phe Phe Gly
305                 310                 315                 320

Asn Phe Tyr Leu Asp Ile Pro Ile Lys Cys Ile Pro Ser His Asp Asn
            325                 330                 335

Gly Asp Leu Glu Leu His Glu Ile Val Thr Leu Ile Arg Asp Glu Lys
            340                 345                 350

Asn Lys Thr Leu Ser Lys Ile Gly Asn Ala Ser Ser Glu Glu Ile Phe
            355                 360                 365

Ser Leu Val Ile Asp Ser Ile Asn Gln Ile Lys Glu Gly Tyr Asn Asp
        370                 375                 380

Asp Glu Ile Asp Leu Tyr Pro Thr Ser Ser Leu Cys Arg Phe Pro Leu
385                 390                 395                 400

Asn Glu Ser Asp Phe Gly Trp Ala Lys Pro Ile Trp Val Ser Arg Val
                405                 410                 415

Asn Val Pro Phe Gln Met Phe Phe Leu Met Asp Ser Lys Asn Gly Ile
            420                 425                 430

Glu Val Arg Val Cys Leu Asn Glu Asp Asp Met Ile Gln Leu Glu Ser
        435                 440                 445

Asp Asp Asp Ile Val Glu Phe Ser Tyr Val Pro Lys
450                 455                 460
```

<210> SEQ ID NO 8
<211> LENGTH: 44
<212> TYPE: DNA
<213> ORGANISM: Artificial Sequence
<220> FEATURE:
<223> OTHER INFORMATION: A primer
<220> FEATURE:
<221> NAME/KEY: variant
<222> LOCATION: (36)..(36)
<223> OTHER INFORMATION: n = a or g or c or t

<400> SEQUENCE: 8
cctactacta atcatgaaca atcttatcct cttwsnttyt tyga        44

<210> SEQ ID NO 9
<211> LENGTH: 37
<212> TYPE: DNA
<213> ORGANISM: Artificial Sequence
<220> FEATURE:
<223> OTHER INFORMATION: A primer
<220> FEATURE:
<221> NAME/KEY: variant
<222> LOCATION: (27)..(27)
<223> OTHER INFORMATION: n = a or g or c or t

<400> SEQUENCE: 9
cttgatcctc ctgaacctca aaattantty ggnaayt        37

<210> SEQ ID NO 10
<211> LENGTH: 40
<212> TYPE: DNA
<213> ORGANISM: Artificial Sequence
<220> FEATURE:
<223> OTHER INFORMATION: A primer
<220> FEATURE:
<221> NAME/KEY: variant
<222> LOCATION: (36)..(36)
<223> OTHER INFORMATION: n = a or g or c or t

```
<400> SEQUENCE: 10
tcttgtagat ttcatcttta tgattgtgay ttyggntggg                    40

<210> SEQ ID NO 11
<211> LENGTH: 28
<212> TYPE: DNA
<213> ORGANISM: Artificial Sequence
<220> FEATURE:
<223> OTHER INFORMATION: A primer
<220> FEATURE:
<221> NAME/KEY: variant
<222> LOCATION: (21)..(21)
<223> OTHER INFORMATION: n = a or g or c or t

<400> SEQUENCE: 11
gccaaatagg ctttccccan ccraartc                                 28

<210> SEQ ID NO 12
<211> LENGTH: 45
<212> TYPE: DNA
<213> ORGANISM: Artificial Sequence
<220> FEATURE:
<223> OTHER INFORMATION: A primer

<400> SEQUENCE: 12
ctgagagaac tagtctcgag ctctagaaca agctttttttt ttttt             45

<210> SEQ ID NO 13
<211> LENGTH: 36
<212> TYPE: DNA
<213> ORGANISM: Artificial Sequence
<220> FEATURE:
<223> OTHER INFORMATION: A primer
<220> FEATURE:
<221> NAME/KEY: variant
<222> LOCATION: (24)..(24)
<223> OTHER INFORMATION: n = i (deoxyinosine)
<220> FEATURE:
<221> NAME/KEY: variant
<222> LOCATION: (25)..(25)
<223> OTHER INFORMATION: n = i
<220> FEATURE:
<221> NAME/KEY: variant
<222> LOCATION: (29)..(29)
<223> OTHER INFORMATION: n = i
<220> FEATURE:
<221> NAME/KEY: variant
<222> LOCATION: (30)..(30)
<223> OTHER INFORMATION: n = i
<220> FEATURE:
<221> NAME/KEY: variant
<222> LOCATION: (34)..(34)
<223> OTHER INFORMATION: n = i
<220> FEATURE:
<221> NAME/KEY: variant
<222> LOCATION: (35)..(35)
<223> OTHER INFORMATION: n = i

<400> SEQUENCE: 13
ggccacgcgt cgactagtac gggnngggnn gggnng                        36

<210> SEQ ID NO 14
<211> LENGTH: 1231
<212> TYPE: DNA
<213> ORGANISM: black pansy

<400> SEQUENCE: 14
aagtaattat cagttaacaa gatggaaatt aaaatcctct caagagaaac caaaaccatc    60
```

-continued

| | |
|---|---|
| agaccatcct ttacttcttc cacaccaaaa cacccagcaa catttaacct cactgttctt | 120 |
| gatcaaatct cccctcaatt ttacatgcta atcattctct actactcccc tgttcacaaa | 180 |
| ctttcaattc cagaaacgtc ccatcattta caaaaatctt tctcagaaac actcgcaaga | 240 |
| ttctaccctc tggcgggtcg aatgcgagat gattggacct gcgtcgattg caacgacgaa | 300 |
| ggtgcgcttt acgtcgaagc tcgagtggag ggcgacatgt catcggtggc gctttcgcag | 360 |
| cagaccaccg aagggttaca aacctgttg cccttaaacc cccacgggga aatacctgat | 420 |
| gaattgagct cccaagtgat cgtggccgtc caagtcaatc atttcgactg tggtgggata | 480 |
| gcaattgctg tttgcctctg gcatgaggtt gcagatgcat ccactctagc caattttatc | 540 |
| aaaatctggg ctgaaattgc tcgaggccac cgcgtggaag aaactgtgga tgatttggtg | 600 |
| attgataaca cctccatctt tatcccacag gacatgacca gccctacggc ccctatattt | 660 |
| tttaagaaac ctgctccagt cacggacagc ttgacaatga aaagttttt gtttcttagt | 720 |
| tccaagattt cttctttgca gaaacaagta acaggttctg atctgcgtcg cccaactcgt | 780 |
| ttcgagaccc tgtcagccct gttatggggg gctttcgcgg ccataaatag tggagaagag | 840 |
| caagacaata cagtatcggg agtgaactta ctgcttgctt tagatttgag gaaaagactg | 900 |
| gatccccagt tgcctggatg ttccattgga aacgtgagcc aatcaatacc cgcattttgg | 960 |
| ccactgaata gcatcagtgt tgatgggagt aacctgacag agtactacaa tcttttagca | 1020 |
| gagaaaattc gcgacacaat gaagtctttg accgacgagc atataaggaa gttccatgga | 1080 |
| gggggtgggt tgtataagat gttgatggag gttggtagaa acaaacctaa gaaggggaa | 1140 |
| gagggtaaga agaagaagat gtttggtatg actagtttgt gtagatttcc gttttacgaa | 1200 |
| tcggacttcg gctggggaaa gcctatttgg c | 1231 |

<210> SEQ ID NO 15
<211> LENGTH: 408
<212> TYPE: PRT
<213> ORGANISM: black pansy

<400> SEQUENCE: 15

```
Leu Ser Val Asn Lys Met Glu Ile Lys Ile Leu Ser Arg Glu Thr Lys
1               5                   10                  15

Thr Ile Arg Pro Ser Phe Thr Ser Thr Pro Lys His Pro Ala Thr
            20                  25                  30

Phe Asn Leu Thr Val Leu Asp Gln Ile Ser Pro Gln Phe Tyr Met Leu
        35                  40                  45

Ile Ile Leu Tyr Tyr Ser Pro Val His Lys Leu Ser Ile Pro Glu Thr
    50                  55                  60

Ser His His Leu Gln Lys Ser Phe Ser Glu Thr Leu Ala Arg Phe Tyr
65                  70                  75                  80

Pro Leu Ala Gly Arg Met Arg Asp Asp Trp Thr Cys Val Asp Cys Asn
                85                  90                  95

Asp Glu Gly Ala Leu Tyr Val Glu Ala Arg Val Glu Gly Asp Met Ser
            100                 105                 110

Ser Val Ala Leu Ser Gln Gln Thr Thr Glu Gly Leu Gln Asn Leu Leu
        115                 120                 125

Pro Leu Asn Pro His Gly Glu Ile Pro Asp Glu Leu Ser Ser Gln Val
    130                 135                 140

Ile Val Ala Val Gln Val Asn His Phe Asp Cys Gly Gly Ile Ala Ile
145                 150                 155                 160

Ala Val Cys Leu Trp His Glu Val Ala Asp Ala Ser Thr Leu Ala Asn
```

```
                   165                 170                 175
Phe Ile Lys Ile Trp Ala Glu Ile Ala Arg Gly His Arg Val Glu Glu
                180                 185                 190

Thr Val Asp Asp Leu Val Ile Asp Asn Thr Ser Ile Phe Ile Pro Gln
            195                 200                 205

Asp Met Thr Ser Pro Thr Ala Pro Ile Phe Phe Lys Lys Pro Ala Pro
        210                 215                 220

Val Thr Asp Ser Leu Thr Met Lys Lys Phe Leu Phe Leu Ser Ser Lys
225                 230                 235                 240

Ile Ser Ser Leu Gln Lys Gln Val Thr Gly Ser Asp Leu Arg Arg Pro
                245                 250                 255

Thr Arg Phe Glu Thr Leu Ser Ala Leu Leu Trp Gly Ala Phe Ala Ala
                260                 265                 270

Ile Asn Ser Gly Glu Glu Gln Asp Asn Thr Val Ser Gly Val Asn Leu
            275                 280                 285

Leu Leu Ala Leu Asp Leu Arg Lys Arg Leu Asp Pro Gln Leu Pro Gly
        290                 295                 300

Cys Ser Ile Gly Asn Val Ser Gln Ser Ile Pro Ala Phe Trp Pro Leu
305                 310                 315                 320

Asn Ser Ile Ser Val Asp Gly Ser Asn Leu Thr Glu Tyr Tyr Asn Leu
                325                 330                 335

Leu Ala Glu Lys Ile Arg Asp Thr Met Lys Ser Leu Thr Asp Glu His
                340                 345                 350

Ile Arg Lys Phe His Gly Gly Gly Leu Tyr Lys Met Leu Met Glu
            355                 360                 365

Val Gly Arg Asn Lys Pro Lys Glu Gly Glu Glu Gly Lys Lys Lys
        370                 375                 380

Met Phe Gly Met Thr Ser Leu Cys Arg Phe Pro Phe Tyr Glu Ser Asp
385                 390                 395                 400

Phe Gly Trp Gly Lys Pro Ile Trp
                405

<210> SEQ ID NO 16
<211> LENGTH: 1227
<212> TYPE: DNA
<213> ORGANISM: black pansy

<400> SEQUENCE: 16
aagtaataat cacttaacaa aatggagata aaaccctct caaaagaaac caaaccatc       60
aaaccatctt ttacttcttc cacaccaaaa cacccagcaa cgtttaacct cacggttctt    120
gatcaaatct cccctcaatt ttacatgcca atcattctat actactcccc tgctcacaaa    180
ctttcaattc cagaaacgtc ccatcattta caaaaatctt tctcagaaac actcgcaaga    240
ttctaccctc tggcgggtcg aatgcgggat gattggacct gcgtcgattg caacgaccaa    300
ggtgcggttt tcgtcgaagc tcgagtggag ggcgacatgt catcggtggc gctttcgcag    360
cagaccaccg aagggctaca gaacctgttg cccttaaacc cccacgggga ataccctgat    420
gaattgagct cccaagtgat cgtgggcgtc caagtcaatc actttgactg tggtgggata    480
gcaattgctg tttgcctctg gcatgaggtt gcagatgcat ccactctagc caattttatc    540
aaaatctggg ctgaaattgc tcgaggccac cccgtccaag aaactgtgga tgatttggtg    600
attgataaca cctccatctt tattccacag gacatgacga gccctacggc ccctaaattt    660
gtcaagaaac ctgctccggt cacggacagc ttgacaatga aaaagttttt gtttcttagt    720
```

-continued

```
tcaaagattt cttctttgca gaaacaagca ccaggttctg atctgcgtcg cccaactcgt    780
ttcgagaccc tgtccgccct gttatggggg gctttcgcgg ccataaatag tgaagacaat    840
gcagtatcgg gagtgaactt actacttgct ttagatttga ggaaaagatt ggatcctcaa    900
ttgccaggat gttctattgg aaacgtgagc caatcaatac ccgcattttg gccactgaat    960
agcgtcagcg ttgataggag taacctgaca gagtactaca atcttttagc agagaaaatt   1020
cgcgagacaa tgaagtcttt gaccgacgag catataagga agttccatgg aggaggtggg   1080
ttgtataaga tgttgatgga ggttggtaga aacaaatcta agaaggggga agaaggtaag   1140
aagaagaagg agaccaagat gtttggtatg actagtttgt gtagatttcc gttttacgaa   1200
tcggacttcg gatggggaaa gcctatt                                       1227
```

<210> SEQ ID NO 17
<211> LENGTH: 406
<212> TYPE: PRT
<213> ORGANISM: black pansy

<400> SEQUENCE: 17

```
Ser Leu Asn Lys Met Glu Ile Lys Thr Leu Ser Lys Glu Thr Lys Thr
1               5                  10                  15

Ile Lys Pro Ser Phe Thr Ser Thr Pro Lys His Pro Ala Thr Phe
            20                  25                  30

Asn Leu Thr Val Leu Asp Gln Ile Ser Pro Gln Phe Tyr Met Pro Ile
        35                  40                  45

Ile Leu Tyr Tyr Ser Pro Ala His Lys Leu Ser Ile Pro Glu Thr Ser
    50                  55                  60

His His Leu Gln Lys Ser Phe Ser Glu Thr Leu Ala Arg Phe Tyr Pro
65                  70                  75                  80

Leu Ala Gly Arg Met Arg Asp Asp Trp Thr Cys Val Asp Cys Asn Asp
                85                  90                  95

Gln Gly Ala Val Phe Val Glu Ala Arg Val Glu Gly Asp Met Ser Ser
            100                 105                 110

Val Ala Leu Ser Gln Gln Thr Thr Glu Gly Leu Gln Asn Leu Leu Pro
        115                 120                 125

Leu Asn Pro His Gly Glu Ile Pro Asp Glu Leu Ser Ser Gln Val Ile
    130                 135                 140

Val Gly Val Gln Val Asn His Phe Asp Cys Gly Gly Ile Ala Ile Ala
145                 150                 155                 160

Val Cys Leu Trp His Glu Val Ala Asp Ala Ser Thr Leu Ala Asn Phe
                165                 170                 175

Ile Lys Ile Trp Ala Glu Ile Ala Arg Gly His Pro Val Gln Glu Thr
            180                 185                 190

Val Asp Asp Leu Val Ile Asp Asn Thr Ser Ile Phe Ile Pro Gln Asp
        195                 200                 205

Met Thr Ser Pro Thr Ala Pro Lys Phe Val Lys Pro Ala Pro Val
    210                 215                 220

Thr Asp Ser Leu Thr Met Lys Lys Phe Leu Phe Leu Ser Ser Lys Ile
225                 230                 235                 240

Ser Ser Leu Gln Lys Gln Ala Pro Gly Ser Asp Leu Arg Arg Pro Thr
                245                 250                 255

Arg Phe Glu Thr Leu Ser Ala Leu Leu Trp Gly Ala Phe Ala Ala Ile
            260                 265                 270

Asn Ser Glu Asp Asn Ala Val Ser Gly Val Asn Leu Leu Leu Ala Leu
        275                 280                 285
```

```
Asp Leu Arg Lys Arg Leu Asp Pro Gln Leu Pro Gly Cys Ser Ile Gly
    290                 295                 300
Asn Val Ser Gln Ser Ile Pro Ala Phe Trp Pro Leu Asn Ser Val Ser
305                 310                 315                 320
Val Asp Arg Ser Asn Leu Thr Glu Tyr Tyr Asn Leu Leu Ala Glu Lys
                325                 330                 335
Ile Arg Glu Thr Met Lys Ser Leu Thr Asp Glu His Ile Arg Lys Phe
            340                 345                 350
His Gly Gly Gly Gly Leu Tyr Lys Met Leu Met Glu Val Gly Arg Asn
        355                 360                 365
Lys Ser Lys Glu Gly Glu Gly Lys Lys Lys Glu Thr Lys Met
    370                 375                 380
Phe Gly Met Thr Ser Leu Cys Arg Phe Pro Phe Tyr Glu Ser Asp Phe
385                 390                 395                 400
Gly Trp Gly Lys Pro Ile
            405
```

<210> SEQ ID NO 18
<211> LENGTH: 19
<212> TYPE: DNA
<213> ORGANISM: Artificial Sequence
<220> FEATURE:
<223> OTHER INFORMATION: A primer

<400> SEQUENCE: 18
cgtcgaagct cgagtggag                                            19

<210> SEQ ID NO 19
<211> LENGTH: 21
<212> TYPE: DNA
<213> ORGANISM: Artificial Sequence
<220> FEATURE:
<223> OTHER INFORMATION: A primer

<400> SEQUENCE: 19
gtttaagggc aacaggttct g                                         21

<210> SEQ ID NO 20
<211> LENGTH: 18
<212> TYPE: DNA
<213> ORGANISM: Artificial Sequence
<220> FEATURE:
<223> OTHER INFORMATION: A primer

<400> SEQUENCE: 20
caggttctga tctgcgtc                                             18

<210> SEQ ID NO 21
<211> LENGTH: 20
<212> TYPE: DNA
<213> ORGANISM: Artificial Sequence
<220> FEATURE:
<223> OTHER INFORMATION: A primer

<400> SEQUENCE: 21
caagtagtaa gttcactccc                                           20

<210> SEQ ID NO 22
<211> LENGTH: 1231
<212> TYPE: DNA
<213> ORGANISM: light blue pansy

```
<400> SEQUENCE: 22
aagtaattat cacttaacaa gatggaaatt aaaatcctct caagagaaac caaaaccatc      60
agaccatctt ttacttcttc cacaccaaaa cacccagcaa catttaacct cactgttctt     120
gatcaaatct cccctcaatt ttacatgcca atcattctct actactcccc tgttcacaaa     180
ctttcaattt cagaaacctc ccatcattta caaaaatctt tctcagaaac actcgcaaga     240
ttctaccctc tggcgggtcg aatgcgagat gattggacct cgtcgattg caacgacgaa      300
ggtgcgcttt acgtcgaagc tcgagtggag ggcgacatgt catcggtggc gctttcgcag     360
cagaccaccg aagggttaca aacctgttg cccttaaacc cccacgggga aatacctgat      420
gaattgagct cccaagtgac cgtggccgtc caagtcaatc attttgactg tggtgggata     480
gcaattgctg tttgcctctg gcatgaggtt gcagatgcat ccaccctagc caattttatc     540
aaaatctggg ctgaaattgc tcgaggccac cgcgtccaag aaactgtgga tgatctggtg     600
attgataaca cctccatctt tatcccacag gacatgacca gccctacggc ccctatattt     660
gttaagaaac ctgctccagt cacggacagc ttgacaatga aaagttttt gtttcttagt      720
tccaagattt ctttttttgca gaaacaagta acaggctctg atctgcgtcg cccaactcgt    780
ttcgagaccc tgtcagccct gttatggggg gctttcgcgg ccataaatag tggagaagag     840
caagacaata cagtatcggg agtgaactta ctacttgctt tagatttgag gaaaagactg     900
gatccccagt tgccaggatg ttccattgga acgtgagcc aatcaatacc cgcattttgg      960
ccactgaata gcgtcagtgt tgatacgagt aacctgacag agtactacaa tcttttagca    1020
agagaaattt gtgacacaat gaagtctttg accgacgagc atataaggaa gttccatgga    1080
ggggtgggt tgtacaagat gttgatggag gttggtagaa acaaacctaa agaagggaa      1140
gagggtaaga agaagaagat gttggtatg actagtttgt gtagatttcc gttttacgaa     1200
tcggatttcg gatggggaaa gcctatttgg c                                   1231

<210> SEQ ID NO 23
<211> LENGTH: 403
<212> TYPE: PRT
<213> ORGANISM: light blue pansy

<400> SEQUENCE: 23

Met Glu Ile Lys Ile Leu Ser Arg Glu Thr Lys Thr Ile Arg Pro Ser
1               5                   10                  15

Phe Thr Ser Ser Thr Pro Lys His Pro Ala Thr Phe Asn Leu Thr Val
            20                  25                  30

Leu Asp Gln Ile Ser Pro Gln Phe Tyr Met Pro Ile Ile Leu Tyr Tyr
        35                  40                  45

Ser Pro Val His Lys Leu Ser Ile Ser Glu Thr Ser His His Leu Gln
    50                  55                  60

Lys Ser Phe Ser Glu Thr Leu Ala Arg Phe Tyr Pro Leu Ala Gly Arg
65                  70                  75                  80

Met Arg Asp Asp Trp Thr Cys Val Asp Cys Asn Asp Glu Gly Ala Leu
                85                  90                  95

Tyr Val Glu Ala Arg Val Glu Gly Asp Met Ser Ser Val Ala Leu Ser
            100                 105                 110

Gln Gln Thr Thr Glu Gly Leu Gln Asn Leu Pro Leu Asn Pro His
        115                 120                 125

Gly Glu Ile Pro Asp Glu Leu Ser Ser Gln Val Thr Val Ala Val Gln
    130                 135                 140
```

```
Val Asn His Phe Asp Cys Gly Ile Ala Ile Ala Val Cys Leu Trp
145                 150                 155                 160

His Glu Val Ala Asp Ala Ser Thr Leu Ala Asn Phe Ile Lys Ile Trp
            165                 170                 175

Ala Glu Ile Ala Arg Gly His Arg Val Gln Glu Thr Val Asp Asp Leu
        180                 185                 190

Val Ile Asp Asn Thr Ser Ile Phe Ile Pro Gln Asp Met Thr Ser Pro
    195                 200                 205

Thr Ala Pro Ile Phe Val Lys Lys Pro Ala Pro Val Thr Asp Ser Leu
210                 215                 220

Thr Met Lys Lys Phe Leu Phe Leu Ser Ser Lys Ile Ser Phe Leu Gln
225                 230                 235                 240

Lys Gln Val Thr Gly Ser Asp Leu Arg Arg Pro Thr Arg Phe Glu Thr
            245                 250                 255

Leu Ser Ala Leu Leu Trp Gly Ala Phe Ala Ala Ile Asn Ser Gly Glu
        260                 265                 270

Glu Gln Asp Asn Thr Val Ser Gly Val Asn Leu Leu Leu Ala Leu Asp
    275                 280                 285

Leu Arg Lys Arg Leu Asp Pro Gln Leu Pro Gly Cys Ser Ile Gly Asn
290                 295                 300

Val Ser Gln Ser Ile Pro Ala Phe Trp Pro Leu Asn Ser Val Ser Val
305                 310                 315                 320

Asp Thr Ser Asn Leu Thr Glu Tyr Tyr Asn Leu Leu Ala Glu Lys Ile
            325                 330                 335

Cys Asp Thr Met Lys Ser Leu Thr Asp Glu His Ile Arg Lys Phe His
        340                 345                 350

Gly Gly Gly Gly Leu Tyr Lys Met Leu Met Glu Val Gly Arg Asn Lys
    355                 360                 365

Pro Lys Glu Gly Glu Glu Gly Lys Lys Lys Met Phe Gly Met Thr
370                 375                 380

Ser Leu Cys Arg Phe Pro Phe Tyr Glu Ser Asp Phe Gly Trp Gly Lys
385                 390                 395                 400

Pro Ile Trp

<210> SEQ ID NO 24
<211> LENGTH: 1189
<212> TYPE: DNA
<213> ORGANISM: light blue pansy

<400> SEQUENCE: 24
acttaacaag atggaaatta aaatcctctc aaaagaaacc aaaaccatca aaccatcttc    60
cacaccaaaa cacccagcaa catttaatct tactgttctt gatcaaatct cccctcaatt   120
ttacatgcca atcattctct actactcccc tgtccacaaa ctttcaattc agaaacgtc    180 ccatcattta caaaaatctt tctcagaaac actcgcaaga ttctacccgc tggcgggtcg    240
aatgcgagat gattggacct gcgttgattg caacgacgaa ggtgcgcttt acgtcgaagc    300
tcgagtggag ggcgacatgt catcggtggc gctttcgcag cagaccaccg aagggttaca    360
gaacctgttg cccttaaacc cccacgggga atacctgat gaattgagct cccaagtgat    420
cgtggccgtc caagtcaatc attttgactg tggtgggata gcaattgctg tttgcctctg    480
gcatgaggtt gcagatgcat ccactctagc caattttatc aaaatctggg ctgaaattgc    540
tcgaggccac cgcgtggaag aaactgtgga tgatttggtg attgataaca cctccatctt    600
tatcccacag gacatgacca gccctacggc ccctatattt gttaagaaac ctgctccagt    660
```

-continued

```
cacggacagc ttgacaatga aaaagtttttt gtttcttagt tccaagatttt cttctttgca    720 gaaacaagta acaggttctg atctgcgtcg cccaactcgt ttcgagaccc tgttagccct    780
gttatggggg gctttcgcgg ccataaatag tggagaagag caagacaata cagtatcggg    840
agtgaactta ctacttgctt tagatttgag gaaaagactg gatccccagt tgccaggatg    900
ttccattgga aacgtgagcc aatcaatacc cgcattttgg ccactgaata gtgtcagtgt    960
tgataggagt aacctgacag agtactacaa tcttttagca gagaaaattc gcgacacaat   1020
gaagtctttg accgacgagc atataaggaa gttccatgga gggggtgggt tgtataagat   1080
gttgatggag gttggtagaa acaaacctaa agaagggaa gagggtaaga agaagaagat   1140
gtttggtatg actagtttgt gtagatttcc gttttacgaa tcggacttc             1189
```

<210> SEQ ID NO 25
<211> LENGTH: 393
<212> TYPE: PRT
<213> ORGANISM: light blue pansy

<400> SEQUENCE: 25

```
Met Glu Ile Lys Ile Leu Ser Lys Glu Thr Lys Thr Ile Lys Pro Ser
1               5                   10                  15

Ser Thr Pro Lys His Pro Ala Thr Phe Asn Leu Thr Val Leu Asp Gln
            20                  25                  30

Ile Ser Pro Gln Phe Tyr Met Pro Ile Ile Leu Tyr Tyr Ser Pro Val
        35                  40                  45

His Lys Leu Ser Ile Pro Glu Thr Ser His His Leu Gln Lys Ser Phe
    50                  55                  60

Ser Glu Thr Leu Ala Arg Phe Tyr Pro Leu Ala Gly Arg Met Arg Asp
65                  70                  75                  80

Asp Trp Thr Cys Val Asp Cys Asn Asp Glu Gly Ala Leu Tyr Val Glu
                85                  90                  95

Ala Arg Val Glu Gly Asp Met Ser Ser Val Ala Leu Ser Gln Gln Thr
            100                 105                 110

Thr Glu Gly Leu Gln Asn Leu Leu Pro Leu Asn Pro His Gly Glu Ile
        115                 120                 125

Pro Asp Glu Leu Ser Ser Gln Val Ile Ala Val Gln Val Asn His
    130                 135                 140

Phe Asp Cys Gly Gly Ile Ala Ile Ala Val Cys Leu Trp His Glu Val
145                 150                 155                 160

Ala Asp Ala Ser Thr Leu Ala Asn Phe Ile Lys Ile Trp Ala Glu Ile
                165                 170                 175

Ala Arg Gly His Arg Val Glu Glu Thr Val Asp Asp Leu Val Ile Asp
            180                 185                 190

Asn Thr Ser Ile Phe Ile Pro Gln Asp Met Thr Ser Pro Thr Ala Pro
        195                 200                 205

Ile Phe Val Lys Lys Pro Ala Pro Val Thr Asp Ser Leu Thr Met Lys
    210                 215                 220

Lys Phe Leu Phe Leu Ser Ser Lys Ile Ser Ser Leu Gln Lys Gln Val
225                 230                 235                 240

Thr Gly Ser Asp Leu Arg Arg Pro Thr Arg Phe Glu Thr Leu Leu Ala
                245                 250                 255

Leu Leu Trp Gly Ala Phe Ala Ala Ile Asn Ser Gly Glu Glu Gln Asp
            260                 265                 270

Asn Thr Val Ser Gly Val Asn Leu Leu Leu Ala Leu Asp Leu Arg Lys
```

```
              275                 280                 285
Arg Leu Asp Pro Gln Leu Pro Gly Cys Ser Ile Gly Asn Val Ser Gln
    290                 295                 300

Ser Ile Pro Ala Phe Trp Pro Leu Asn Ser Val Ser Val Asp Arg Ser
305                 310                 315                 320

Asn Leu Thr Glu Tyr Tyr Asn Leu Leu Ala Glu Lys Ile Arg Asp Thr
                325                 330                 335

Met Lys Ser Leu Thr Asp Glu His Ile Arg Lys Phe His Gly Gly Gly
            340                 345                 350

Gly Leu Tyr Lys Met Leu Met Glu Val Gly Arg Asn Lys Pro Lys Glu
        355                 360                 365

Gly Glu Glu Gly Lys Lys Lys Met Phe Gly Met Thr Ser Leu Cys
    370                 375                 380

Arg Phe Pro Phe Tyr Glu Ser Asp Phe
385                 390
```

<210> SEQ ID NO 26
<211> LENGTH: 14
<212> TYPE: DNA
<213> ORGANISM: Artificial Sequence
<220> FEATURE:
<223> OTHER INFORMATION: A primer
<220> FEATURE:
<221> NAME/KEY: variant
<222> LOCATION: (3)..(3)
<223> OTHER INFORMATION: n = I
<220> FEATURE:
<221> NAME/KEY: variant
<222> LOCATION: (6)..(6)
<223> OTHER INFORMATION: n = I

<400> SEQUENCE: 26
ytnwsnttyt tyga                                                      14

<210> SEQ ID NO 27
<211> LENGTH: 23
<212> TYPE: DNA
<213> ORGANISM: Artificial Sequence
<220> FEATURE:
<223> OTHER INFORMATION: A primer
<220> FEATURE:
<221> NAME/KEY: variant
<222> LOCATION: (15)..(15)
<223> OTHER INFORMATION: n = i
<220> FEATURE:
<221> NAME/KEY: variant
<222> LOCATION: (21)..(21)
<223> OTHER INFORMATION: n = i

<400> SEQUENCE: 27
gargaycara ayywnttygg naa                                            23

<210> SEQ ID NO 28
<211> LENGTH: 24
<212> TYPE: DNA
<213> ORGANISM: Artificial Sequence
<220> FEATURE:
<223> OTHER INFORMATION: A primer
<220> FEATURE:
<221> NAME/KEY: variant
<222> LOCATION: (4)..(4)
<223> OTHER INFORMATION: n = i
<220> FEATURE:
<221> NAME/KEY: variant
<222> LOCATION: (10)..(10)
<223> OTHER INFORMATION: n = i -continued

```
<400> SEQUENCE: 28
gttnccraan wrrttytgrt cytc                                    24

<210> SEQ ID NO 29
<211> LENGTH: 17
<212> TYPE: DNA
<213> ORGANISM: Artificial Sequence
<220> FEATURE:
<223> OTHER INFORMATION: A primer
<220> FEATURE:
<221> NAME/KEY: variant
<222> LOCATION: (9)..(9)
<223> OTHER INFORMATION: n = i
<220> FEATURE:
<221> NAME/KEY: variant
<222> LOCATION: (15)..(15)
<223> OTHER INFORMATION: n = i

<400> SEQUENCE: 29
gayttyggnt gggsnaa                                            17

<210> SEQ ID NO 30
<211> LENGTH: 18
<212> TYPE: DNA
<213> ORGANISM: Artificial Sequence
<220> FEATURE:
<223> OTHER INFORMATION: A primer
<220> FEATURE:
<221> NAME/KEY: variant
<222> LOCATION: (4)..(4)
<223> OTHER INFORMATION: n = i
<220> FEATURE:
<221> NAME/KEY: variant
<222> LOCATION: (10)..(10)
<223> OTHER INFORMATION: n = i

<400> SEQUENCE: 30
yttnscccan ccraartc                                           18

<210> SEQ ID NO 31
<211> LENGTH: 45
<212> TYPE: DNA
<213> ORGANISM: Artificial Sequence
<220> FEATURE:
<223> OTHER INFORMATION: A primer

<400> SEQUENCE: 31
gagagagaga gagagagaga tctccagttt tttttttttt ttttt             45
```

US 7,173,164 B2

PLANT ANTHOCYANIDIN RUTINOSIDE AROMATIC ACYL TRANSFERASES

RELATED APPLICATIONS

This application is a continuation under 35 U.S.C. 111(a) of PCT/AU01/00358 filed Mar. 30, 2001 and published in English as WO 01/72984 A1 on Oct. 4, 2001, which claims priority from Australian application PQ 6598 filed Mar. 31, 2000, which applications and publication are incorporated herein by reference.

FIELD OF THE INVENTION

The present invention relates generally to a genetic sequence encoding a polypeptide having aromatic acyl group transfer activity and the use of the genetic sequence and/or its corresponding polypeptide thereof. More particularly, the present invention provides a genetic sequence encoding a polypeptide having aromatic acyl group transfer activity derived from *Petunia, Nierembergia* and *Viola* spp. Even more particularly, the present invention relates to a genetic sequence encoding a polypeptide having aromatic acyl group transferase activity to anthocyanidin-rutinoside. The present invention also provides a genetic sequence encoding a polypeptide having aromatic acyl group transferase activity to anthocyanidin 3-O-rutinoside. The instant invention further relates to antisense and sense molecules corresponding to all or part of the subject genetic sequence as well as genetically modified plants as well as cut flowers, parts and reproductive tissue from such plants.

BACKGROUND OF THE INVENTION

Bibliographic details of the publications referred to by author in this specification are collected at the end of the description.

Reference to any prior art in this specification is not, and should not be taken as, an acknowledgment or any form of suggestion that this prior art forms part of the common general knowledge in Australia or any other country.

The flower and ornamental plant industry strives to develop new and different varieties of flowers and/or plants. In the flower industry in particular, an effective way to create such novel varieties is through the manipulation of flower colour where classical breeding techniques have been used with some success to produce a wide range of colours for most of the commercial varieties of flowers and/or plants. This approach has been limited, however, by the constraints of a particular species' gene pool and for this reason it is rare for a single species to have the full spectrum of coloured varieties. For example, the development of novel coloured varieties of plants or plant parts such as flowers, foliage and stems would offer a significant opportunity in both the cut flower and ornamental markets.

In the flower industry, the development of novel coloured varieties of major species such as rose, chrysanthemum, tulip, lily, carnation, gerbera, orchid, lisianthus, begonia, torenia, geranium, petunia and nierembergia would be of great interest. A more specific example would be the development of a blue rose or gerbera for the cut flower market.

In addition, the development of novel coloured varieties of plant parts such as vegetables, fruits and seeds would offer significant opportunities in agriculture, for example, novel coloured seeds would be useful as proprietary tags for plants.

Flower and fruit colour is predominantly due to flavonoids which contribute a range of colours from yellow to red to blue. The flavonoid molecules which make the major contribution to flower colour are the anthocyanins which are glycosylated derivatives of cyanidin, delphinidin, petunidin, peonidin, malvidin and pelargonidin, and are localized in the vacuole.

The flavonoid pigments are secondary metabolites of the phenylpropanoid pathway. The biosynthetic pathway for the flavonoid pigments (flavonoid pathway) is well established, (Ebel and Hahlbrock, 1988; Hahlbrock and Grisebach, 1979; Wiering and De Vlaming, 1984; Schram et al., 1984; Stafford, 1990, Holton and Cornish, 1995) and is shown in FIGS. 1A and B. Three reactions and enzymes are involved in the conversion of phenylalanine to p-coumaroyl-CoA, one of the first key substrates in the flavonoid pathway. The enzymes are phenylalanine ammonia-lyase (PAL), cinnamate 4-hydroxylase (C4H) and 4-coumarate: CoA ligase (4CL). The first committed step in the pathway involves the condensation of three molecules of malonyl-CoA (provided by the action of acetyl CoA carboxylase (ACC) on acetyl CoA and $CO_2$) with one molecule of p-coumaroyl-CoA. This reaction is catalyzed by the enzyme chalcone synthase (CHS). The product of this reaction, 2',4,4',6', tetrahydroxy chalcone, is normally rapidly isomerized by the enzyme chalcone flavanone isomerase (CHI) to produce naringenin. Naringenin is subsequently hydroxylated at the 3 position of the central ring by flavanone 3-hydroxylase (F3H) to produce dihydrokaempferol (DHK).

The B-ring of DHK can be hydroxylated at either the 3', or both the 3' and 5' positions, to produce dihydroquercetin (DHQ) and dihydromyricetin (DHM), respectively. The pattern of hydroxylation of the B-ring plays a key role in determining petal colour, with DHK generally leading to the production of the brick red pelargonidin-based pigments, DHQ generally leading to the red/pink cyanidin-based pigments and DHM generally leading to the blue/violet delphinidin-based pigments.

The dihydroflavonols (DHK, DHQ and DHM) can also be acted upon by flavonol synthase to produce the flavonols kaempferol, quercetin and myricetin. The flavonols are colourless but act as copigments with the anthocyanins to enhance flower colour.

The next step in the pathway, leading to the production of the coloured anthocyanins from the dihydroflavonols, involves dihydroflavonol-4-reductase (DFR) with the production of the leucoanthocyanidins. These flavonoid molecules are unstable under normal physiological conditions and glycosylation at the 3-position, through the action of glycosyltransferases, stabilizes the anthocyanidin molecule thus allowing accumulation of the anthocyanins. In general, the glycosyltransferases transfer the sugar moieties from UDP sugars and show high specificities for the position of glycosylation and relatively low specificities for the acceptor substrates (Seitz and Hinderer, 1988). Anthocyanins can occur as 3-monosides, 3-biosides and 3-triosides as well as 3,5-diglycosides and 3,7-diglycosides associated with the sugars glucose, galactose, rhamnose, arabinose and xylose (Strack and Wray, 1993).

Glycosyltransferases involved in the stabilization of the anthocyanidin molecule include UDP glucose: flavonoid 3-glucosyltransferase (3GT), which transfers a glucose moiety from UDP glucose to the 3-O-position of the anthocyanidin molecule to produce anthocyanidin 3-O-glucoside. In petunia and pansy (amongst others), these anthocyanins can then be glycosylated by another glycosyltransferase, UDP rhamnose: anthocyanidin 3-glucoside rhamnosyltransferase (3RT), which adds a rhamnose group to the 3-O-bound glucose of the anthocyanin molecule to produce the anthocyanidin 3-rutinosides, and once acylated, can be further modified by UDP glucose: anthocyanidin 3-(p-coumaroyl)-rutinoside 5 glucosyltransferase (5GT).

Many anthocyanidin glycosides exist in the form of polyacylated derivatives. Acylation may be important for uptake of anthocyanins into the vacuoles as was demonstrated by Hopp and Seitz (1987). The acyl groups that modify the anthocyanidin glycosides can be divided into 2 major classes based upon their structure. The aliphatic acyl groups such as malonic acid or succinic acid and the aromatic class such as the hydroxy cinnamic acids including p-coumaric acid, caffeic acid and ferulic acid and the benzoic acids such as p-hydroxybenzoic acid. Aromatic acyl groups have been reported to cause intra and/or intermolecular co-pigmentation that leads to the stabilization of the anthocyanin molecule with a bathochromic shift (a positive shift in the wavelength of the maximum of absorption of the visible band) and a subsequent bluing of the colour (Dangles et al., 1993: Lu et al., 1992) (Brouillard and Dangles, 1993). In fact many blue flowers have been shown to contain aromatically acylated delphinidin pigments (Goto and Kondo, 1991).

A number of plants contain anthocyanins aromatically acylated at a glucose (Brouillard and Dangles, 1993) that may be attached to the anthocyanin molecule at positions C3, C5, C7, C3' or C5' (see Strack and Wray (1993) for figure of anthocyanin structure). For example, *Perilla ocimoides* has been shown to contain the anthocyanin shisonin in which coumaric acid is bound to glucose at position C3 of cyanidin 3,5-diglucoside (Goto et al., 1987). *Gentiana makinoi* has been shown to contain the anthocyanin gentiodelphin which contains an aromatic acyl group attached to a glucose at position C3' and an aromatic acyl group attached to a glucose at position C5 (Yoshida et al., 1992). However, the anthocyanins in *Petunia hybrida* flowers are acylated by p-coumaric acid or caffeic acid at a rhamnose group attached to a glucose group at position C3 to produce anthocyanidin 3-p-coumaroylrutinoside 5-glucosides and anthocyanidin 3-caffeoylrutinoside 5-glucosides (Griesbach et al., 1991). This is also the case in a number of other flowers such as petals of *Silene dioica* (Kamsteeg et al., 1980), flowers of *Viola tricolour* contain violanin (delphinidin 3-coumaroyl-rutinoside 5-glucoside) (Goto et al., 1978), *Lobelia erinus* flowers contain anthocyanins with a 3-coumaroylrutinoside group (Kondo et al., 1989), *Iris ensenta* flowers contain malvidin 3-coumaroylrutinoside-5-glucoside, petunidin 3-coumaroylrutinoside-5-glucoside and delphinidin 3-coumaroylrutinoside-5-glucoside (Yabuya, T., 1991) and *Eustoma grandiflorum* flowers contain delphinidin 3-coumaroylrhamnosylgalactoside-5-glucoside and pelargonidin 3-coumaroylrhamnosylgalactoside-5-glucoside (Asen et al., 1986). All of which would probably produce an aromatic acyltransferase that is able to attach an aromatic acyl group to the rhamnose group that is attached to a glycosyl at position C3 of the anthocyanin molecule.

The isolation of flavonoid aromatic acyltransferases which transfer aromatic acyl groups to the glucose attached to the flavonoid molecule has been disclosed in PCT/JP96/00348 (International Patent Publication No. WO 96/25500) entitled A gene encoding a protein having acyl group transfer activity. These sequences include the 5-aromatic acyltransferase from *Gentiana triflora* (Fujiwara et al., 1998), the encoded amino acid sequences of anthocyanidin-glucoside aromatic acyltransferases from *Gentiana triflora* (pGAT4 and pGAT106), *Senecio cruentus* (pCAT8), *Lavandula angustifolia* (pLAT21), *Perilla ocimoides* (pSAT8) and a *Petunia hybrida* homologue (pPAT48).

In addition to the above modifications, pH and copigmentation with other flavonoids such as flavonols and flavones can affect petal colour. Flavonols and flavones can also be aromatically acylated (Brouillard and Dangles, 1993).

The ability to control the activity of anthocyanidin 3-rutinoside acyltransferase would provide a means of manipulating petal colour thereby enabling a single species to express a broader spectrum of flower colours. Such control may be by modulating the level of production of an indigenous enzyme or by introducing a non-indigenous enzyme.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1, <400>2, etc. A sequence listing is provided after the claims.

One aspect of the present invention provides an isolated nucleic acid molecule comprising a sequence of nucleotides encoding, or complementary to a sequence encoding AR-AT or a functional derivative of the enzyme.

A further aspect of the present invention is directed to an isolated nucleic acid molecule comprising a sequence of nucleotides encoding, or complementary to a sequence encoding AR-AT or a functional mutant, derivative, part, fragment, homologue or analogue of AR-AT.

Another aspect of the present invention provides a nucleic acid molecule comprising a nucleotide sequence or complementary nucleotide sequence substantially as set forth in SEQ ID NO:1 or having at least about 50% similarity thereto or capable of hybridizing to the sequence set forth in SEQ ID NO:1 under low stringency conditions.

Yet another aspect of the present invention provides a nucleic acid molecule comprising a nucleotide sequence or complementary nucleofide sequence substantially as set forth in SEQ ID NO:6 or having at least about 50% similarity thereto or capable of hybridizing to the sequence set forth in SEQ ID NO:6 or its complementary strand under low stringency conditions.

Still another aspect of the present invention provides a nucleic acid molecule comprising a nucleotide sequence or complementary nucleotide sequence substantially as set forth in SEQ ID NO:14 or having at least about 50% similarity thereto or capable of hybridizing to the sequence set forth in SEQ ID NO:14 or its complementary strand under low stringency conditions.

Still a further aspect of the present invention provides a nucleic acid molecule comprising a nucleotide sequence or complementary nucleotide sequence substantially as set forth in SEQ ID NO:16 or having at least about 50% similarity thereto or capable of hybridizing to the sequence set forth in SEQ ID NO:16 or its complementary strand under low stringency conditions.

Even yet another aspect of the present invention provides a nucleic acid molecule comprising a nucleotide sequence or complementary nucleotide sequence substantially as set forth in SEQ ID NO:22 or having at least about 50% similarity thereto or capable of hybridizing to the sequence set forth in SEQ ID NO:22 or its complementary strand under low stringency conditions.

Even still another aspect of the present invention provides a nucleic acid molecule comprising a nucleotide sequence or complementary nucleotide sequence substantially as set forth in SEQ ID NO:24 or having at least about 50% similarity thereto or capable of hybridizing to the sequence set forth in SEQ ID NO:24 or its complementary strand under low stringency conditions.

A further aspect of the present invention provides an isolated nucleic acid molecule comprising a nucleotide sequence or complementary nucleotide sequence substantially as set forth in SEQ ID NO:1 or SEQ ID NO:6 or SEQ ID NO:14 or SEQ ID NO:16 or SEQ ID NO:22 or SEQ ID NO:24 or having at least about 50% similarity thereto or capable of hybridising to the sequence set forth in SEQ ID NO:1 or SEQ ID NO:6 or SEQ ID NO:14 or SEQ ID NO:16 or SEQ ID NO:22 or SEQ ID NO:24 or complementary strands of either under low stringency conditions, wherein said nucleotide sequence encodes a polypeptide having AR-AT activity.

Another aspect of the present invention provides a nucleic acid molecule comprising a sequence of nucleotides encoding or complementary to a sequence encoding an amino acid sequence substantially as set forth in SEQ ID NO:2 or an amino acid sequence having at least about 50% similarity thereto.

Yet another aspect of the present invention provides a nucleic acid molecule comprising a sequence of nucleotides encoding or complementary to a sequence encoding an amino acid sequence substantially as set forth in SEQ ID NO:7 or an amino acid sequence having at least about 50% similarity thereto.

Still another aspect of the present invention provides a nucleic acid molecule comprising a sequence of nucleotides encoding or complementary to a sequence encoding an amino acid sequence substantially as set forth in SEQ ID NO:15 or an amino acid sequence having at least about 50% similarity thereto.

Still a further aspect of the present invention provides a nucleic acid molecule comprising a sequence of nucleotides encoding or complementary to a sequence encoding an amino acid sequence substantially as set forth in SEQ ID NO:17 or an amino acid sequence having at least about 50% similarity thereto.

Even yet another aspect of the present invention provides a nucleic acid molecule comprising a sequence of nucleotides encoding or complementary to a sequence encoding an amino acid sequence substantially as set forth in SEQ ID NO:23 or an amino acid sequence having at least about 50% similarity thereto.

Even still another aspect of the present invention provides a nucleic acid molecule comprising a sequence of nucleotides encoding or complementary to a sequence encoding an amino acid sequence substantially as set forth in SEQ ID NO:25 or an amino acid sequence having at least about 50% similarity thereto.

A further aspect of the present invention provides an oligonucleotide of 5–50 nucleotides having substantial similarity or complementarity to a part or region of a molecule with a nucleotide sequence set forth in SEQ ID NO:1 or SEQ ID NO:6 or SEQ ID NO:14 or SEQ ID NO:16 or SEQ ID NO:22 or SEQ ID NO:24 or a complementary form thereof.

Another aspect of the present invention provides a method for producing a transgenic flowering plant capable of synthesizing AR-AT, said method comprising stably transforming a cell of a suitable plant with a nucleic acid sequence which comprises a sequence of nucleotides encoding said AR-AT under conditions permitting the eventual expression of said nucleic acid sequence, regenerating a transgenic plant from the cell and growing said transgenic plant for a time and under conditions sufficient to permit the expression of the nucleic acid sequence. The transgenic plant may thereby produce non-indigenous AR-AT at elevated levels relative to the amount expressed in a comparable non-transgenic plant.

Yet another aspect of the present invention contemplates a method for producing a transgenic plant with reduced indigenous or existing AR-AT activity, said method comprising stably transforming a cell of a suitable plant with a nucleic acid molecule which comprises a sequence of nucleotides encoding or complementary to a sequence encoding an AR-AT activity, regenerating a transgenic plant from the cell and where necessary growing said transgenic plant under conditions sufficient to permit the expression of the nucleic acid.

Still another aspect of the present invention contemplates a method for producing a genetically modified plant with reduced indigenous or existing AR-AT activity, said method comprising altering the AR-AT gene through modification of the indigenous sequences via homologous recombination from an appropriately altered AR-AT gene or derivative or part thereof introduced into the plant cell, and regenerating the genetically modified plant from the cell.

Still a further aspect of the present invention contemplates a method for producing a transgenic flowering plant exhibiting altered inflorescence properties, said method comprising stably transforming a cell of a suitable plant with a nucleic acid sequence of the present invention, regenerating a transgenic plant from the cell and growing said transgenic plant for a time and under conditions sufficient to permit the expression of the nucleic acid sequence into an AR-AT.

Eve yet another aspect of the present invention contemplates a method for producing a flowering plant exhibiting altered inflorescence properties, said method comprising alteration of the AR-AT gene through modification of the indigenous sequences via homologous recombination from an appropriately altered AR-AT gene or derivative or part thereof introduced into the plant cell, and regenerating the genetically modified plant from the cell.

Even still another aspect of the present invention extends to a method for producing a transgenic plant capable of expressing a recombinant gene encoding an AR-AT or part thereof or which carries a nucleic acid sequence which is substantially complementary to all or a part of a mRNA molecule optionally transcribable where required to effect regulation of an AR-AT, said method comprising stably transforming a cell of a suitable plant with the isolated nucleic acid molecule comprising a sequence of nucleotides encoding, or complementary to a sequence encoding, an AR-AT, where necessary under conditions permitting the eventual expression of said isolated nucleic acid molecule, and regenerating a transgenic plant from the cell.

A further aspect of the present invention extends to all transgenic plants or parts of transgenic plants or progeny of the transgenic plants containing all or part of the nucleic acid sequences of the present invention, or antisense forms thereof and/or any homologues or related forms thereof and, in particular, those transgenic plants which exhibit altered inflorescence properties.

Another aspect of the present invention is directed to recombinant forms of AR-AT.

Yet aspect of the present invention contemplates the use of the genetic sequences described herein in the manufacture of a genetic construct capable of expressing an AR-AT or down-regulating an indigenous AR-AT enzyme in a plant.

Still another aspect of the present invention is directed to a prokaryotic or eukaryotic organism carrying a genetic sequence encoding an AR-AT extrachromasomally in plasmid form.

Still a further aspect of the present invention extends to a recombinant polypeptide comprising a sequence of amino acids substantially as set forth in SEQ ID NO:2 or SEQ ID NO:7 or SEQ ID NO:15 or SEQ ID NO:17 or SEQ ID NO:23 or SEQ ID NO:25 or an amino acid sequence having at least about 50% similarity to SEQ ID NO:2 or SEQ ID NO:7 or SEQ ID NO:15 or SEQ ID NO:17 or SEQ ID NO:23 or SEQ ID NO:25 or a derivative of said polypeptide.

Figure 1A:
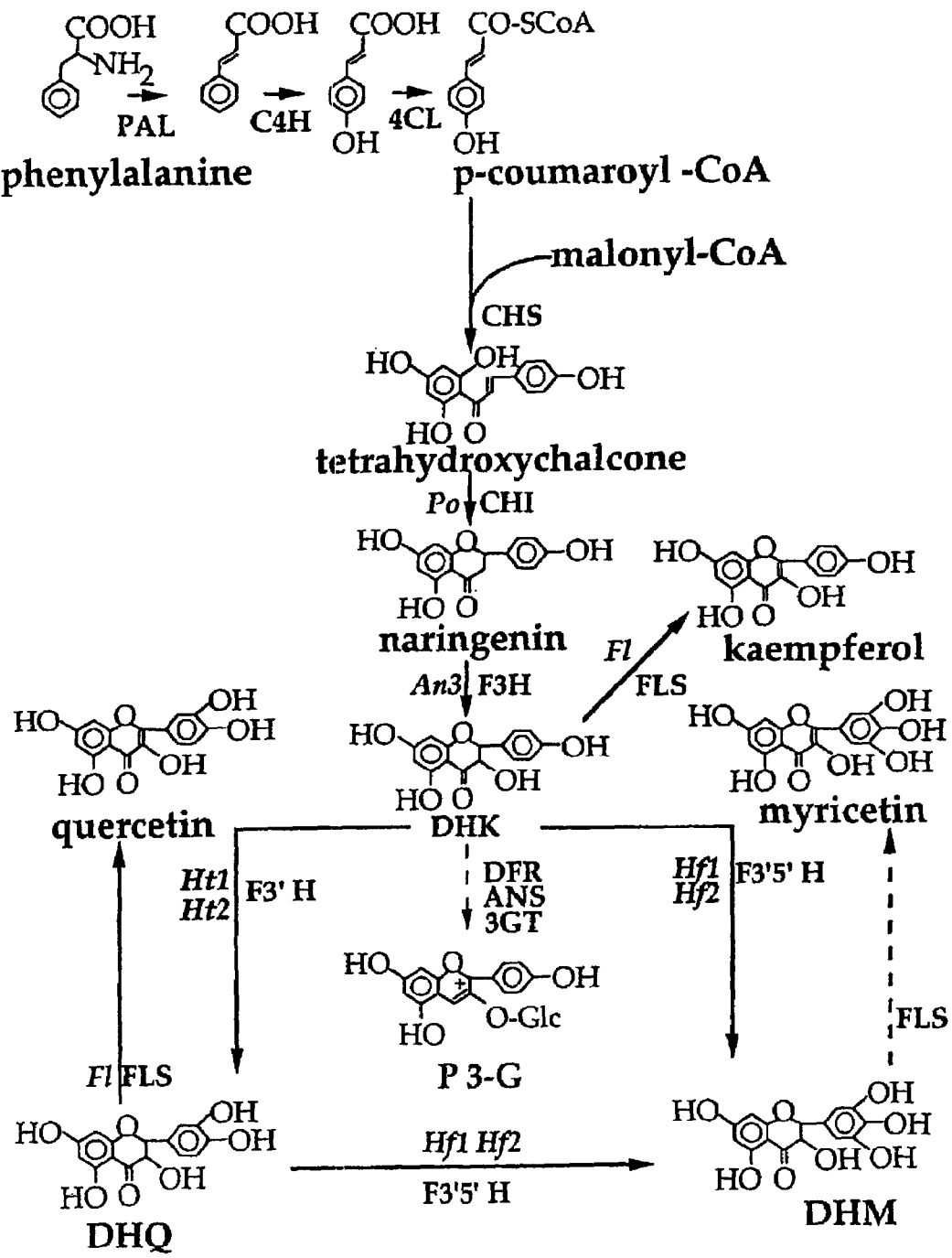
FIGS. 1A and 1B are schematic representations of the biosynthesis pathway for the flavonoid pigments in petunia. Enzymes involved in the pathway have been indicated as follows: PAL=Phenylalanine ammonia-lyase; C4H=Cinnamate 4-hydroxylase; 4CL=4-coumarate: CoA ligase; CHS=Chalcone synthase; CHI=Chalcone flavanone isomerase; F3H=Flavanone 3-hydroxylase; DFR=Dihydroflavonol-4-reductase; ANS=Anthocyanidin synthase, 3GT=UDP-glucose: flavonoid 3-O-glucosyltransferase; 3RT=UDP rhamnose: anthocyanidin 3-glucoside rhamnosyltransferase, AR-AT=Anthocyanidin-rutinoside acyltransferase, 5GT=Anthocyanin 5-glucosyltransferase; 3' OMT=Anthocyanin 3' methyltransferase, 3'5' OMT=Anthocyanin 3',5' methyltransferase. Other abbreviations include: DHK=dihydrokaempferol, DHQ=dihydroquercetin, DHM=dihydromyricetin, P 3-G=pelargonidin 3-glucoside. Some of the genetic loci that control these reactions in petunia are shown in italics alongside the enzymes. Myricetin and pelargonidin based pigments occur rarely in petunia.

A summary of sequence identifiers is provided herewith.

SUMMARY OF SEQENCE IDENTIFIERS

| SEQUENCE ID NO: | DESCRIPTION |
| --- | --- |
| 1 | petunia AR AT.nt |
| 2 | petunia AR AT.aa |
| 3 | "GAGATTTT" |
| 4 | petatF |
| 5 | petatR |
| 6 | Nierembergia AR AT.nt |
| 7 | Nierembergia AR AT.aa |
| 8 | Atf11 |
| 9 | Atf2 |
| 10 | Atf3 |
| 11 | ATr3 |
| 12 | dT(17)Ad2Ad1 |
| 13 | GI anchor |
| 14 | pCGP3074 (BPAR-AT2).nt |
| 15 | pCGP3074 (BPAR-AT2).aa |
| 16 | pCGP3075 (BPAR-AT3).nt |
| 17 | pCGP3075 (BPAR-AT3).aa |
| 18 | BPAT2F |
| 19 | BPAT2R |
| 20 | BPAT3F |
| 21 | BPAT3R |
| 22 | pCGP3076 (LBAR-AT3).nt |
| 23 | pCGP3076 (LBAR-AT3).aa |
| 24 | pCGP3077 (LBAR-AT17).nt |
| 25 | pCGP3077 (LBAR-AT17).aa |
| 26 | Primer 1f |
| 27 | Primer 3f |
| 28 | Primer 3r |
| 29 | Primer 4f |
| 30 | Primer 4r |
| 31 | XhoTTTT |

DETAILED DESCRIPTION OF THE PREFERRED EMBODIMENTS

In accordance with the present invention, a genetic sequence encoding anthocyanidin-rutinoside acyltransferase (hereinafter referred to as "AR-AT"), has been identified and cloned. The recombinant sequence permits the modulation of aromatic acylation of the rhamnose moiety of rutinoside (i.e. being comprised of glucose-rhamnose unit) when it is attached to a flavonoid molecule. Substrates include anthocyanins with a rutinoside group attached via an oxygen to position 3 of anthocyanin such as delphinidin 3-rutinoside, cyanidin 3-rutinoside and pelargonidin 3-rutinoside, thereby providing a means to manipulate petal colour. It is expected that AR-AT will also aromatically acylate anthocyanins with a rutinoside group attached via an oxygen at other positions on the anthocyanin molecule such as position 5, position 7, position 3', position 4' and position 5'. Accordingly, the present invention relates to the altering of AR-AT activity in plants, which encompasses elevating or reducing (i.e. modulating) levels of existing AR-AT activity by introducing a sequence of the present invention. Reduction in levels of AR-AT activity may also be referred to as down-regulation. Moreover, the present invention extends to plants and reproductive or vegetative parts thereof including flowers, seeds, vegetables, leaves, stems, etc., and more particularly, ornamental transgenic plants. The term transgenic also includes progeny plants from the transgenic plants.

Accordingly, one aspect of the present invention provides an isolated nucleic acid molecule comprising a sequence of nucleotides encoding, or complementary to a sequence encoding AR-AT or a functional derivative of the enzyme.

The present invention is described and exemplified herein by reference to the identification, cloning and manipulation of genetic sequences encoding AR-AT which, up to the present time, is a particularly convenient and useful flavonoid aromatic acylating enzyme for the practice of the invention herein disclosed. This is done, however, with the understanding that the present invention extends to all novel AR-AT enzymes and their functional derivatives.

For convenience and by way of short hand notation only, reference herein to a flavonoid acylating enzyme includes AR-ATs acting on flavonoids such as anthocyanins, flavonols and/or flavones. Preferably, the flavonoid acylating enzyme is AR-AT. The AR-AT enzyme may also be considered to include a polypeptide or protein having AR-AT activity or AR-AT-like activity. The latter encompasses derivatives having altered AR-AT activities.

A preferred aspect of the present invention, therefore, is directed to an isolated nucleic acid molecule comprising a sequence of nucleotides encoding, or complementary to a sequence encoding AR-AT or a functional mutant, derivative, part, fragment, homologue or analogue of AR-AT.

By the term "nucleic acid molecule" is meant a genetic sequence in a non-naturally occurring condition. Generally, this means isolated away from its natural state or synthesized or derived in a non-naturally-occurring environment. More specifically, it includes nucleic acid molecules formed or maintained in vitro, including genomic DNA fragments recombinant or synthetic molecules and nucleic acids in combination with heterologous nucleic acids. It also extends to the genomic DNA or cDNA or part thereof encoding AR-AT or a part thereof in reverse orientation relative to its or another promoter. It further extends to naturally occurring sequences following at least a partial purification relative to other nucleic acid sequences.

The term genetic sequences is used herein in its most general sense and encompasses any contiguous series of nucleotide bases specifying directly, or via a complementary series of bases, a sequence of amino acids in an AR-AT enzyme. Such a sequence of amino acids may constitute a full-length AR-AT such as is set forth in SEQ ID NO:2 or SEQ ID NO:7 or SEQ ID NO:15 or SEQ ID NO:17 or SEQ ID NO:23 or SEQ ID NO:25 or an active truncated form thereof or may correspond to a particular region such as an N-terminal, C-terminal or internal portion of the enzyme. A genetic sequence may also be referred to as a sequence of nucleotides or a nucleotide sequence and include a recombinant fusion of two or more sequences.

In accordance with the above aspects of the present invention there is provided a nucleic acid molecule comprising a nucleotide sequence or complementary nucleotide sequence substantially as set forth in SEQ ID NO:1 or having at least about 50% similarity thereto or capable of hybridizing to the sequence set forth in SEQ ID NO:1 under low stringency conditions.

Alternative percentage similarity encompassed by the present invention include at least about 60% or at least about 70% or at least about 80% or at least about 90% or above, such as about 95% or about 96% or about 97% or about 98% or about 99%.

In a related embodiment, there is provided a nucleic acid molecule comprising a nucleotide sequence or complementary nucleotide sequence substantially as set forth in SEQ ID NO:6 or having at least about 50% similarity thereto or capable of hybridizing to the sequence set forth in SEQ ID NO:6 or its complementary strand under low stringency conditions.

In another embodiment, there is provided a nucleic acid molecule comprising a nucleotide sequence or complementary nucleotide sequence substantially as set forth in SEQ ID NO:14 or having at least about 50% similarity thereto or capable of hybridizing to the sequence set forth in SEQ ID NO:14 or its complementary strand under low stringency conditions.

In a further embodiment, there is provided a nucleic acid molecule comprising a nucleotide sequence or complementary nucleotide sequence substantially as set forth in SEQ ID NO:16 or having at least about 50% similarity thereto or capable of hybridizing to the sequence set forth in SEQ ID NO:16 or its complementary strand under low stringency conditions.

In still another embodiment, there is provided a nucleic acid molecule comprising a nucleotide sequence or complementary nucleotide sequence substantially as set forth in SEQ ID NO:22 or having at least about 50% similarity thereto or capable of hybridizing to the sequence set forth in SEQ ID NO:22 or its complementary strand under low stringency conditions.

In yet another embodiment, there is provided a nucleic acid molecule comprising a nucleotide sequence or complementary nucleotide sequence substantially as set forth in SEQ ID NO:24 or having at least about 50% similarity thereto or capable of hybridizing to the sequence set forth in SEQ ID NO:24 or its complementary strand under low stringency conditions.

In a particularly preferred embodiment, there is provided an isolated nucleic acid molecule comprising a nucleotide sequence or complementary nucleotide sequence substantially as set forth in SEQ ID NO:1 or SEQ ID NO:6 or SEQ ID NO:14 or SEQ ID NO:16 or SEQ ID NO:22 or SEQ ID NO:24 or having at least about 50% similarity thereto or capable of hybridising to the sequence set forth in SEQ ID NO:1 or SEQ ID NO:6 or SEQ ID NO:14 or SEQ ID NO:16 or SEQ ID NO:22 or SEQ ID NO:24 or complementary strands of either under low stringency conditions, wherein said nucleotide sequence encodes a polypeptide having AR-AT activity.

For the purposes of determining the level of stringency to define nucleic acid molecules capable of hybridizing to SEQ ID NO:1 or SEQ ID NO:6 or SEQ ID NO:14 or SEQ ID NO:16 or SEQ ID NO:22 or SEQ ID NO:24, reference herein to a low stringency includes and encompasses from at least about 0 to at least about 15% v/v formamide and from at least about 1M to at least about 2 M salt for hybridization, and at least about 1 M to at least about 2 M salt for washing conditions. Generally, low stringency is at from about 25–30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15M salt for hybridization, and at least about 0.01 M to at least about 0.15 M salt for washing conditions. In general, washing is carried out $T_m=69.3+0.41$ (G+C)% (Marmur and Doty, 1962). However, the $T_m$ of a duplex DNA decreases by 1° C. with every increase of 1% in the number of mismatch base pairs (Bonner and Laskey, 1974). Formamide is optional in these hybridization conditions. Accordingly, particularly preferred levels of stringency are defined as follows: low stringency is 6×SSC buffer, 1.0% w/v SDS at 25–42° C.; a moderate stringency is 2×SSC buffer, 1.0% w/v SDS at a temperature in the range 20° C. to 65° C.; high stringency is 0.1×SSC buffer, 0.1% w/v SDS at a temperature of at least 65° C.

Another aspect of the present invention provides a nucleic acid molecule comprising a sequence of nucleotides encoding or complementary to a sequence encoding an amino acid sequence substantially as set forth in SEQ ID NO:2 or an amino acid sequence having at least about 50% similarity thereto.

In a related embodiment, there is provided a nucleic acid molecule comprising a sequence of nucleotides encoding or complementary to a sequence encoding an amino acid sequence substantially as set forth in SEQ ID NO:7 or an amino acid sequence having at least about 50% similarity thereto.

In another embodiment, there is provided a nucleic acid molecule comprising a sequence of nucleotides encoding or complementary to a sequence encoding an amino acid sequence substantially as set forth in SEQ ID NO:15 or an amino acid sequence having at least about 50% similarity thereto.

In a further embodiment, there is provided a nucleic acid molecule comprising a sequence of nucleotides encoding or complementary to a sequence encoding an amino acid sequence substantially as set forth in SEQ ID NO:17 or an amino acid sequence having at least about 50% similarity thereto.

In yet another embodiment, there is provided a nucleic acid molecule comprising a sequence of nucleotides encoding or complementary to a sequence encoding an amino acid sequence substantially as set forth in SEQ ID NO:23 or an amino acid sequence having at least about 50% similarity thereto.

In still another embodiment, there is provided a nucleic acid molecule comprising a sequence of nucleotides encoding or complementary to a sequence encoding an amino acid sequence substantially as set forth in SEQ ID NO:25 or an amino acid sequence having at least about 50% similarity thereto.

The term similarity as used herein includes exact identity between compared sequences at the nucleotide or amino acid level. Where there is non-identity at the nucleotide level, similarity includes differences between sequences which result in different amino acids that are nevertheless related to each other at the structural, functional, biochemical and/or conformational levels. Where there is non-identity at the amino acid level, similarity includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al. (1997). A detailed discussion of sequence analysis can be found in Unit 19.3 of Ausubel et al. (1998).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

The nucleic acid sequences contemplated herein also encompass oligonucleotides useful as genetic probes for amplification reactions or as antisense or sense molecules capable of regulating expression of the corresponding gene in a plant. An antisense molecule as used herein may also encompass a genetic construct comprising the structural genomic or cDNA gene or part thereof in reverse orientation relative to its or another promoter. It may also encompass a homologous genetic sequence. An antisense or sense molecule may also be directed to terminal or internal portions of the gene encoding a polypeptide having AR-AT activity.

With respect to this aspect of the invention, there is provided an oligonucleotide of 5–50 nucleotides having substantial similarity or complementarity to a part or region of a molecule with a nucleotide sequence set forth in SEQ ID NO:1 or SEQ ID NO:6 or SEQ ID NO:14 or SEQ ID NO:16 or SEQ ID NO:22 or SEQ ID NO:24 or a complementary form thereof. By substantial similarity or complementarity in this context is meant a hybridizable similarity under low, alternatively and preferably medium and alternatively and most preferably high stringency conditions specific for oligonucleotide hybridization (Sambrook et al., 1989). Such an oligonucleotide is useful, for example, in screening AR-AT genetic sequences from various sources or for monitoring an introduced genetic sequence in a transgenic plant. The preferred oligonucleotide is directed to a conserved AR-AT genetic sequence or a sequence conserved within a plant genus, plant species and/or plant strain or variety.

In one aspect of the present invention, the oligonucleotide corresponds to the 5' or the 3' end of the AR-AT genetic sequence. For convenience, the 5' end is considered herein to define a region substantially between the start codon of the structural gene to a centre portion of the gene, and the 3' end is considered herein to define a region substantially between the centre portion of the gene and the terminating codon of the structural gene. It is clear, therefore, that oligonucleotides or probes may hybridize to the 5' end or the 3' end or to a region common to both the 5' and the 3' ends. The present invention extends to all such probes.

In one embodiment, the nucleic acid sequence encoding an AR-AT or various functional derivatives thereof is used to reduce the level of an endogenous AR-AT (e.g. via co-suppression), or alternatively the nucleic acid sequence encoding this enzyme or various derivatives or parts thereof is used in the antisense orientation to reduce the level of AR-AT. Although not wishing to limit the present invention to any one theory or mode of action, it is possible that an antisense AR-AT transcript or fragment or part thereof (for example, an oligonucleotide molecule) would form a duplex with all or part of the naturally occurring mRNA specified for the enzyme thus preventing accumulation of or translation from the mRNA into active enzyme. In a further alternative, ribozymes could be used to inactivate target nucleic acid sequences.

Still a further embodiment encompasses post-transcriptional inhibition to reduce translation into polypeptide material.

Reference herein to the altering of AR-AT activity relates to an elevation or reduction in activity of up to 30% or more preferably of 30–50%, or even more preferably 50–75% or still more preferably 75% or greater above or below the normal endogenous or existing levels of activity. Such elevation or reduction may be referred to as modulation of AR-AT enzyme activity. Generally, modulation is at the level of transcription or translation of AR-AT genetic sequences.

The nucleic acids of the present invention may be a ribonucleic acid or deoxyribonucleic acids, single or double stranded and linear or covalently closed circular molecules. Preferably, the nucleic acid molecule is cDNA. The present invention also extends to other nucleic acid molecules which hybridize under low, preferably under medium and most preferably under high stringency conditions with the nucleic acid molecules of the present invention and in particular to the sequence of nucleotides set forth in SEQ ID NO:1 or SEQ ID NO:6 or SEQ ID NO:14 or SEQ ID NO:16 or SEQ ID NO:22 or SEQ ID NO:24 a part or region thereof. In its most preferred embodiment, the present invention extends to a nucleic acid molecule having a nucleotide sequence set forth in SEQ ID NO:1 or SEQ ID NO:6 or SEQ ID NO:14 or SEQ ID NO:16 or SEQ ID NO:22 or SEQ ID NO:24 or to a molecule having at least 40%, more preferably at least 45%, even more preferably at least 55%, still more preferably at least 65–70%, and yet even more preferably greater than 85% similarity at the level of nucleotide or amino acid sequence to at least one or more regions of the sequence set forth in SEQ ID NO:1 or SEQ ID NO:6 or SEQ ID NO:14 or SEQ ID NO:16 or SEQ ID NO:22 or SEQ ID NO:24 and wherein the nucleic acid encodes or is complementary to a sequence which encodes an enzyme having AR-AT activity. It should be noted, however, that nucleotide or amino acid sequences may have similarities below the above given percentages and yet still encode AR-AT activity and such molecules may still be considered in the scope of the present invention where they have regions of sequence conservation. The present invention further extends to nucleic acid molecules in the form of oligonucleotide primers or probes capable of hybridizing to a portion of the nucleic acid molecules contemplated above, and in particular those set forth in SEQ ID NO:1 or SEQ ID NO:6 or SEQ ID NO:14 or SEQ ID NO:16 or SEQ ID NO:22 or SEQ ID NO:24, under low, preferably under medium and most preferably under high stringency conditions. Preferably the portion corresponds to the 5' or the 3' end of the gene. For convenience the 5' end is considered herein to define a region substantially between the start codon of the structural genetic sequence to a centre portion of the gene, and the 3' end is considered herein to define a region substantially between the centre portion of the gene and the terminating codon of the structural genetic sequence. It is clear, therefore, that oligonucleotides or probes may hybridize to the 5' end or the 3' end or to a region common to both the 5' and the 3' ends. The present invention extends to all such probes.

The term gene is used in its broadest sense and includes cDNA corresponding to the exons of a gene. Accordingly, reference herein to a gene is to be taken to include:

(i) a classical genomic gene consisting of transcriptional and/or translational regulatory sequences and/or a coding region and/or non-translated sequences (i.e. introns, 5'- and 3'-untranslated sequences); or (ii) mRNA or cDNA corresponding to the coding regions (i.e. exons) and 5'- and 3'-untranslated sequences of the gene.

The term gene is also used to describe synthetic or fusion molecules encoding all or part of an expression product. In particular embodiments, the term nucleic acid molecule and gene may be used interchangeably.

The nucleic acid or its complementary form may encode the full-length enzyme or a part or derivative thereof. By "derivative" is meant any single or multiple amino acid substitutions, deletions, and/or additions relative to the naturally occurring enzyme and which retains AR-AT activity. In this regard, the nucleic acid includes the naturally occurring nucleotide sequence encoding AR-AT or may contain single or multiple nucleotide substitutions, deletions and/or additions to said naturally occurring sequence. The nucleic acid of the present invention or its complementary form may also encode a "part" of the AR-AT, whether active or inactive, and such a nucleic acid molecule may be useful as an oligonucleotide probe, primer for polymerase chain reactions or in various mutagenic techniques, or for the generation of antisense molecules.

Reference herein to a "part" of a nucleic acid molecule, nucleotide sequence or amino acid sequence, preferably relates to a molecule which contains at least about 10 contiguous nucleotides or five contiguous amino acids, as appropriate.

Amino acid insertional derivatives of the AR-AT of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Typical substitutions are those made in accordance with Table 1.

TABLE 1

Suitable residues for amino acid substitutions

| Original residue | Exemplary substitutions |
|---|---|
| Ala | Ser |
| Arg | Lys |
| Asn | Gln; His |
| Asp | Glu |
| Cys | Ser |
| Gln | Asn; Glu |
| Glu | Asp |
| Gly | Pro |
| His | Asn; Gln |
| Ile | Leu; Val |
| Leu | Ile; Val |
| Lys | Arg; Gln; Glu |
| Met | Leu; Ile; Val |
| Phe | Met; Leu; Tyr |
| Ser | Thr |
| Thr | Ser |
| Trp | Tyr |
| Tyr | Trp; Phe |
| Val | Ile; Leu; Met |

Where the AR-AT is derivatized by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield, 1964) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al., (1989).

Other examples of recombinant or synthetic mutants and derivatives of the AR-AT enzyme of the present invention include single or multiple substitutions, deletions and/or additions of any molecule associated with the enzyme such as carbohydrates, lipids and/or proteins or polypeptides.

The terms "analogues" and "derivatives" also extend to any functional chemical equivalent of AR-AT and also to any amino acid derivative described above. For convenience, reference to AR-AT herein includes reference to any functional mutant, derivative, part, fragment, homologue or analogue thereof.

The present invention is exemplified using nucleic acid sequences derived from petunia, *Nierembergia* or *Viola* spp. since this represents the most convenient and preferred source of material to date. However, one skilled in the art will immediately appreciate that similar sequences can be isolated from any number of sources such as other plants or certain microorganisms. All such nucleic acid sequences encoding directly or indirectly an AR-AT are encompassed by the present invention regardless of their source. Examples of other suitable sources of genes encoding anthocyanidin 3-rutinoside acyl transferases include, but are not limited to *Viola tricolour, Lobelia erinus, Eustoma grandiflorum, Iris ensenta, Antirrhinum* spp., *cyclamen, Metrosideros, Alstroemeria, Potentilla* spp., *Saintpaulia ionantha, Bromeliaceae* spp. and *geranium*.

In accordance with the present invention, a nucleic acid sequence encoding AR-AT may be introduced into and expressed in a transgenic plant in either orientation thereby providing a means either to convert suitable substrates, if synthesized in the plant cell, ultimately into anthocyanidin 3-acylrutinosides, or alternatively to inhibit such conversion of metabolites by reducing or eliminating endogenous or existing AR-AT activity. The production of these anthocyanins will modify petal colour and may contribute to the production of a bluer colour. Expression of the nucleic acid sequence in the plant may be constitutive, inducible or developmental and may also be tissue-specific. The word expression is used in its broadest sense to include production of RNA or of both RNA and protein. It also extends to partial expression of a nucleic acid molecule.

According to this aspect of the present invention, there is provided a method for producing a transgenic flowering plant capable of synthesizing AR-AT, said method comprising stably transforming a cell of a suitable plant with a nucleic acid sequence which comprises a sequence of nucleotides encoding said AR-AT under conditions permitting the eventual expression of said nucleic acid sequence, regenerating a transgenic plant from the cell and growing said transgenic plant for a time and under conditions sufficient to permit the expression of the nucleic acid sequence. The transgenic plant may thereby produce non-indigenous AR-AT at elevated levels relative to the amount expressed in a comparable non-transgenic plant.

Another aspect of the present invention contemplates a method for producing a transgenic plant with reduced indigenous or existing AR-AT activity, said method comprising stably transforming a cell of a suitable plant with a nucleic acid molecule which comprises a sequence of nucleotides encoding or complementary to a sequence encoding an AR-AT activity, regenerating a transgenic plant from the cell and where necessary growing said transgenic plant under conditions sufficient to permit the expression of the nucleic acid.

Yet another aspect of the present invention contemplates a method for producing a genetically modified plant with reduced indigenous or existing AR-AT activity, said method comprising altering the AR-AT gene through modification of the indigenous sequences via homologous recombination from an appropriately altered AR-AT gene or derivative or part thereof introduced into the plant cell, and regenerating the genetically modified plant from the cell.

As used herein an "indigenous" enzyme is one, which is native to or naturally expressed in a particular cell. A "non-indigenous" enzyme is an enzyme not native to the cell but expressed through the introduction of genetic material into a plant cell; for example, through a transgene. An "endogenous" enzyme is an enzyme produced by a cell but which may or may not be indigenous to that cell.

In a preferred embodiment, the present invention contemplates a method for producing a transgenic flowering plant exhibiting altered inflorescence properties, said method comprising stably transforming a cell of a suitable plant with a nucleic acid sequence of the present invention, regenerating a transgenic plant from the cell and growing said transgenic plant for a time and under conditions sufficient to permit the expression of the nucleic acid sequence into an AR-AT. Alternatively, said method may comprise stably transforming a cell of a suitable plant with a nucleic acid sequence of the present invention or its complementary sequence, regenerating a transgenic plant from the cell and growing said transgenic plant for a time and under conditions sufficient to alter the level of activity of the indigenous or existing AR-AT. Preferably the altered level would be less than the indigenous or existing level of AR-AT activity in a comparable non-transgenic plant. Without wishing to limit the present invention, one theory of mode of action is that reduction of the indigenous AR-AT activity requires the expression of the introduced nucleic acid sequence or its complementary sequence. However, expression of the introduced genetic sequence or its complement may not be required to achieve the desired effect: namely, a flowering plant exhibiting altered inflorescence properties.

In a related embodiment, the present invention contemplates a method for producing a flowering plant exhibiting altered inflorescence properties, said method comprising alteration of the AR-AT gene through modification of the indigenous sequences via homologous recombination from an appropriately altered AR-AT gene or derivative or part thereof introduced into the plant cell, and regenerating the genetically modified plant from the cell.

Preferably, the altered inflorescence includes the production of different shades of blue or red flowers or other colours, depending on the genotype and physiological conditions of the recipient plant.

Accordingly, the present invention extends to a method for producing a transgenic plant capable of expressing a recombinant gene encoding an AR-AT or part thereof or which carries a nucleic acid sequence which is substantially complementary to all or a part of a mRNA molecule optionally transcribable where required to effect regulation of an AR-AT, said method comprising stably transforming a cell of a suitable plant with the isolated nucleic acid molecule comprising a sequence of nucleotides encoding, or complementary to a sequence encoding, an AR-AT, where necessary under conditions permitting the eventual expression of said isolated nucleic acid molecule, and regenerating a transgenic plant from the cell. By suitable plant is meant a plant capable of producing anthocyanidin 3-rutinosides and possessing the appropriate physiological properties required for the development of the colour desired.

One skilled in the art will immediately recognize the variations applicable to the methods of the present invention, such as increasing or decreasing the expression of the enzyme naturally present in a target plant leading to differing shades of colours such as different shades of blue or red The present invention, therefore, extends to all transgenic plants or parts of transgenic plants or progeny of the transgenic plants containing all or part of the nucleic acid sequences of the present invention, or antisense forms thereof and/or any homologues or related forms thereof and, in particular, those transgenic plants which exhibit altered inflorescence properties. The transgenic plants may contain an introduced nucleic acid molecule comprising a nucleotide sequence encoding or complementary to a sequence encoding an AR-AT. Generally, the nucleic acid would be stably introduced into the plant genome, although the present invention also extends to the introduction of an AR-AT nucleotide sequence within an autonomously-replicating nucleic acid sequence such as a DNA or RNA virus capable of replicating within the plant cell. The invention also extends to seeds from such transgenic plants. Such seeds, especially if coloured, are useful as proprietary tags for plants. Any and all methods for introducing genetic material into plant cells are encompassed by the present invention.

A further aspect of the present invention is directed to recombinant forms of AR-AT. The recombinant forms of the enzyme will provide a source of material for research to develop, for example, more active enzymes and may be useful in developing in vitro systems for production of coloured compounds.

Still a further aspect of the present invention contemplates the use of the genetic sequences described herein in the manufacture of a genetic construct capable of expressing an AR-AT or down-regulating an indigenous AR-AT enzyme in a plant.

Another aspect of the present invention is directed to a prokaryotic or eukaryotic organism carrying a genetic sequence encoding an AR-AT extrachromasomally in plasmid form.

The present invention further extends to a recombinant polypeptide comprising a sequence of amino acids substantially as set forth in SEQ ID NO:2 or SEQ ID NO:7 or SEQ ID NO:15 or SEQ ID NO:17 or SEQ ID NO:23 or SEQ ID NO:25 or an amino acid sequence having at least about 50% similarity to SEQ ID NO:2 or SEQ ID NO:7 or SEQ ID NO:15 or SEQ ID NO:17 or SEQ ID NO:23 or SEQ ID NO:25 or a derivative of said polypeptide.

A "recombinant polypeptide" means a polypeptide encoded by a nucleotide sequence introduced into a cell directly or indirectly by human intervention or into a parent or other relative or precursor of the cell. A recombinant polypeptide may also be made using cell-free, in vitro transcription systems. The term "recombinant polypeptide" includes an isolated polypeptide or when present is a cell or cell preparation. It may also be in a plant or parts of a plant regenerated from a cell which produces said polypeptide.

A "polypeptide" includes a peptide or protein and is encompassed by the term "enzyme".

The recombinant polypeptide may also be a fusion molecule comprising two or more heterologous amino acid sequences.

The present invention is further described by the following non-limiting Examples.

EXAMPLE 1

Plant Material

The *Petunia hybrida* cultivars used are presented in Table 2.

TABLE 2

*Petunia hybrida* cultivars

| Plant variety | Properties | Source/Reference |
|---|---|---|
| V23 | An1, An2, An3, An4, An6, An8, An9, An10, ph1, Hf1, Hf2, ht1, Rt, po, Bl, Fl | Wallroth et al. (1986) Doodeman et al. (1984) |
| R51 | An1, An2, An3, an4, An6, An8, An9, An10, An11, Ph1, hf1, hf2, Ht1, rt, Po, bl, fl | Wallroth et al. (1986) Doodeman et al. (1984) |
| VR | V23 × R51 F1 Hybrid | |
| Br140 | An1, An2, an4, an6/An6*, Ph1, Ph2, Ph5, Hf1, Ht1, Rt, po, Mt1, mf1, mf2, Gf, fl | INRA |
| Old Glory Blue (OGB) | F$_1$ Hybrid (commercial cultivar) | Ball Seed, USA |
| V26 | An1, An2, An3, an4, An6, An8, An9, An10, An11, Ph1, ph2, Ph5, Hf1, hf2, Ht1, Rt, po, Bl, Gf, Mt1, Mt2, mf1, mf2, Fl | INRA |
| W162 | an1 | Vrije Universiteit, Amsterdam |

INRA = Institut National de la Recherche Agronomique, Cedex, France

OGB petunia plants were grown in specialized growth rooms with a 14 hr day length at a light intensity of 10,000 lux and a temperature of 22 to 26° C. OGB flowers were harvested at developmental stages defined as follows:

Stage 1: Unpigmented, closed bud (<25 mm in length).
Stage 2: Pigmented, closed bud (25–35 mm in length).
Stage 3: Dark purple bud with emerging corolla (>35 mm in length).
Stage 4: Dark purple opened flower pre-anther dehiscence (>50 mm in length).
Stage 5: Fully opened flower with all anthers dehisced.

Pansy Developmental Stages

In general, pansy flowers were harvested at the developmental stages defined as follows:

Stage 1: Pigmented, closed bud (<14 mm in length).
Stage 2: Strongly pigmented closed bud (14–16 mm in length).
Stage 3: Strongly pigmented bud with emerging petals (16–22 mm in length).

-continued

Stage 4: Strongly pigmented flower with emerging petals (22–25 mm in length).
Stage 5: Fully opened flower (>24 mm in length).

EXAMPLE 2

Bacterial Strains

The *Escherichia coli* strains used were:

| | |
|---|---|
| DH5α | supE44, Δ(lacZYA-ArgF)U169, (ø80lacZΔM15), hsdR17($r_k^-$, $m_k^+$), recA1, endA1, gyrA96, thi-1, relA1, deoR. (Hanahan, 1983 and BRL, 1986). |
| XL1-Blue | supE44, hsdR17($r_k^-$, $m_k^+$), recA1, endA1, gyrA96, thi-1, relA1, lac$^-$,[F'proAB, lacI$^q$, lacZΔM15, Tn10(tet$^R$)] (Bullock et al., 1987). |
| PLK-F' | recA, hsdR17($r_k^-$, $m_k^+$), mcrA$^-$, mcrB$^-$lac$^-$, supE44, galK2, galT22, metB1, [F' proAB, lacI$^q$, lacZΔM15, Tn10(tet$^R$)] (Stratagene). |

EXAMPLE 3

General Methods

In general, the methods followed were as described in Sambrook et al. (1989).

The disarmed *Agrobacterium tumefaciens* strain used was AGL0 (Lazo et al., 1991).

The cloning vectors pBluescript, pBluescribe and PCR script were obtained from STRATAGENE. pCR7 2.1 was obtained from INVITROGEN.

*E. coli* Transformation

Transformation of the *E. coli* strains was performed according to the method of Inoue et al., (1990).

$^{32}$P-Labelling of DNA Probes

DNA fragments (50 to 100 ng) were radioactively labelled with 50 μCi of [α-$^{32}$P]-dCTP using a Gigaprime kit (GENEWORKS). Unincorporated [α-$^{32}$P]-dCTP was removed by chromatography on a Sephadex G-50 (Fine) column.

Plasmid Isolation

Helper phage R408 (STRATAGENE) was used to excise pBluescript phagemids containing petunia cDNA inserts from the amplified λZAP cDNA libraries using methods described by the manufacturer. *E. coli* XL1-Blue were transfected with the phagemid mixture and the colonies were plated out on LB plates (Sambrook et al, 1989) containing 100 μg/mL ampicillin. Single colonies were analyzed for cDNA inserts by growing in LB broth (Sambrook et al., 1989) with ampicillin (100 μg/mL) and isolating the plasmid using the alkali-lysis procedure (Sambrook et al., 1989) or using The WizardPlus SV minipreps DNA purification system (Promega). Once the presence of a cDNA insert had been determined, larger amounts of plasmid DNA were prepared from 50 mL overnight cultures using a QIAfilter Plasmid midi kit (QIAGEN).

DNA Sequence Analysis

DNA sequencing was performed using the PRISM ™ Ready Reaction Dye Primer Cycle Sequencing Kits from Applied Biosystems. The protocols supplied by the manufacturer were followed. The cycle sequencing reactions were performed using a Perkin Elmer PCR machine (GeneAmp PCR System 9600) and run on an automated 373A DNA sequencer (Applied Biosystems).

Homology searches against Genbank, SWISS-PROT and EMBL databases were performed using the FASTA and TFASTA programs (Pearson and Lipman, 1988) or BLAST programs (Altschul et al., 1990). Percentage sequence similarities were obtained using the LFASTA program (Pearson and Lipman, 1988). In all cases, ktup values of 6 for nucleotide sequence comparisons and 2 for amino acid sequence comparisons were used, unless otherwise specified.

Multiple sequence alignments and bootstrap trees were produced using ClustalW (Thompson et al., 1996) and njplot (mgouy@biomserv.univ-lyon1.fr) respectively.

EXAMPLE 4

Isolation of a Partial Anthocyanidin Rutinoside Acyltransferase (AR-AT) cDNA Clone From *Petunia hybrida*

Construction and Screening of a *P. hybrida* cv. V26 Petal cDNA Library

A cDNA library was constructed based on mRNA from corolla limb tissue of the line V26 (An1$^+$) (Kroon et al., 1994). Around 30,000 pfu of the V26 floral cDNA library were plated at a density of 800 pfu per 90 mm plate. Duplicate lifts of these were taken onto Hybond-N membranes (Amersham) and treated as recommended by the manufacturer. The filters were hybridized with first strand cDNA from an An1$^+$ (V26) and an an1$^-$ line (W162). Hybridization conditions included a prehybridization step in 50% v/v formamide, 5×SSPE, 5×Denhardt's, 0.1% w/v SDS, 100 μg/mL herring sperm DNA at 42° C. for 3 hours. For hybridization 1.0×10$^8$ cpm $^{32}$P-labelled first strand cDNA and 100 μg of poly (A) were added and incubation was continued for 16–48 hours at 42° C. The filters were washed in 1×SSC/0.1% w/v SDS at 60° C. for 30 minutes and then exposed to Kodak XAR film for 3 to 4 days. Two hundred and seventy plaque forming units (pfu) out of 30,000 showed substantially stronger hybridization to the An1$^+$ cDNA probe than to the an1$^-$ cDNA probe. Of these, 35 which did not hybridize to previously cloned pigmentation genes (chs, chi and dfr) were purified to homogeneity. Pairwise cross-hybridizations demonstrated that these 35 clones represented 7 distinct classes of genes—difA, difC, difF, difG, difH and difI. DifG has subsequently been shown to represent the Rt gene of *Petunia hybrida* (Kroon et al., 1994). The expression profiles of the remaining 6 classes were shown to display a spatial, temporal and genetic control similar to that of difG (Kroon et al., 1994).

Figure 2:
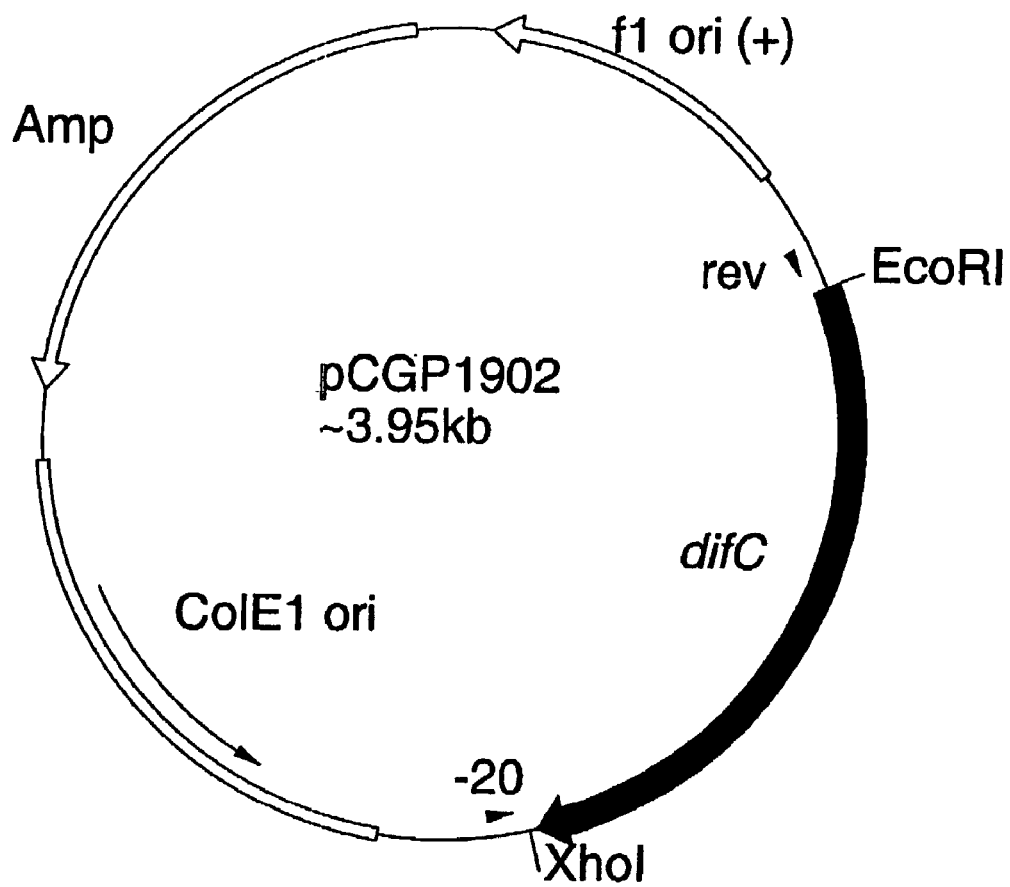
FIG. 2 is a diagrammatic representation of the plasmid pCGP1902 containing the difC cDNA clone from *P. hybrida*. $^{32}$P-labelled fragments of the 1.0 kb EcoRI/XhoI fragment were used to probe the Old Glory Blue petal cDNA library. Abbreviations are as follows: Amp=the ampicillin resistance gene, fi ori (+)=fl filamentous phage origin of replication, ColE1ori=plasmid origin of replication, rev=approximate location of the M13 reverse primer site used in sequence analysis, −20=approximate location of the M13 −20 primer site used in sequence analysis. A selection of restriction endonuclease recognition sites are also marked.

The difC clone was shown to be around 1 kb and the plasmid was assigned the designation pCGP1902 (FIG. 2). RFLP analysis indicated that the difC clone was weakly linked to the Hf2 locus on chromosome V and so was a candidate for the Gf gene. The Gf locus controls the acylation of the anthocyanidin 3-rutinosides in petunia. The difC clone was selected for further analysis.

EXAMPLE 5

Isolation of a Full-length AR-AT cDNA Clone From *Petunia hybrida*

Construction of OGB Petal cDNA Library

Total RNA was isolated from the petal tissue of *P. hybrida* cv Old Glory Blue (OGB) stage 3 to 4 flowers using the method of Turpen and Griffith (1986). Poly(A)$^+$ RNA was selected from the total RNA by three cycles of oligo-dT cellulose chromatography (Aviv and Leder, 1972).

Two micrograms of poly(A)$^+$ RNA were reverse transcribed in a 20 μL volume containing 1×Superscript ™ reaction buffer, 10 mM dithiothreitol, 500 μM dATP, 500 μM dGTP, 500 μM dTTP, 500 μM 5-methyl-dCTP, 0.75 μg oligonucleotide (SEQ ID NO:3) and 2 μL Superscript™ reverse transcriptase (BRL). The reaction mix was incubated at 37° C. for 50 minutes, 44° C. for 10 minutes and then placed on ice.

A second strand reaction mix (140 μL) was added to the first strand reaction mix. The second strand reaction mix consisted of 21 mM Tris-HCl, 104 mM KCl, 5.3 mM MgCl$_2$, 171 μM β-NAD, 11.4 mM (NH$_4$)$_2$SO$_4$, 214 μM dATP, 642 μM dCTP, 214 μM dGTP, 214 μM dTTP, 4 mM DTT, 10 μCi $^{32}$P-dCTP (3000 Ci/mMole), 15 units *E. coli* DNA ligase, 40 units *E. coli* DNA polymerase I (Boehringer) and 0.8 units RNAse H. The final mixture was incubated for 150 minutes at 16° C. To make the double-stranded cDNA blunt-ended, 10 units T4 DNA polymerase was added, and the reaction continued for a further 15 minutes at 16° C. The reaction was stopped and the cDNA purified by phenol/chloroform extraction, followed by chloroform extraction and ethanol precipitation.

EcoRI adaptors (Promega) were ligated with the cDNA and then kinased using conditions recommended by the manufacturer. The enzymes were denatured by heat (70° C., 20 minutes) and the DNA was purified by phenol/chloroform extraction and ethanol precipitation. The cDNA was digested with 50 units xhoI (Boehringer) in a reaction volume of 100 μL, using conditions recommended by the manufacturer. The enzyme was heat killed (70° C., 20 minutes) and the mixture passed through an S400 spin column (Pharmacia) which had been equilibrated in STE buffer (Sambrook et al., 1989). The eluate was phenol/chloroform extracted and ethanol precipitated. After microcentrifugation at 4° C. for 30 minutes the cDNA pellet was rinsed with 70% v/v ethanol, air dried and resuspended in 10 μL of TE buffer (1 mM Tris-HCl (pH 7.5), 1 mM EDTA).

A 2.5 μL aliquot of the cDNA mixture was ligated with 1 μg λZAPII EcoRI/XhoI/CIAP (calf intestinal alkaline phosphatase) treated vector (Stratagene) in 5 μL reaction buffer consisting of 50 mM Tris-HCl (pH 7.0), 10 mM MgCl$_2$, 10 mM dithiothreitol, 1 mM ATP and 2 units T4 DNA ligase. The reaction was performed at 4° C. for 4 days.

After incubating at room temperature for two hours, the ligation reaction mixture was packaged using the Packagene system (Promega). The total number of recombinants was 1×10$^6$ pfu.

After transfecting PLK-F' cells, the packaged λZAPII/cDNA was plated at 50,000 pfu per 15 cm diameter plate. The plates were incubated at 37° C. for eight hours, and the phage were eluted in 100 mM NaCl, 8 mM MgSO$_4$, 50 mM Tris-HCl pH 8.0, 0.01% gelatin (Phage Storage Buffer (PSB)). Chloroform was added and the phage stored at 4° C. as an amplified library.

40,000 pfu of the amplified library were plated onto NZY plates (Sambrook et al., 1989) at a density of 20,000 pfu per 15 cm plate after transfecting XL1-Blue MRF' cells, and incubated at 37° C. for 8 hours. After incubation at 4° C. overnight, duplicate lifts were taken onto Colony/Plaque Screen ™ filters (DuPont) and treated as recommended by the manufacturer.

Screening of OGB Library

Prior to hybridization, the duplicate plaque lifts were washed in prewashing solution (50 mM Tris-HCl pH 7.5, 1 M NaCl, 1 mM EDTA, 0.1% w/v sarcosine) at 65° C. for 30 minutes; stripped in 0.4 M sodium hydroxide at 65° C. for 30 minutes; then washed in a solution of 0.2 M Tris-HCl pH 8.0, 0.1×SSC, 0.1% w/v SDS at 65° C. for 30 minutes and finally rinsed in 2×SSC, 1.0% w/v SDS.

The duplicate lifts from the OGB petal cDNA library were screened with $^{32}$P-labelled fragments of an EcoRI/XhoI difC fragment from pCGP1902 (FIG. 2).

Hybridization conditions included a prehybridization step in 50% v/v formamide, 1 M NaCl, 10% w/v dextran sulphate, 1% w/v SDS at 42° C. for at least 1 hour. The $^{32}$P-labelled fragments (at 1×10$^6$ cpm/mL) were then added to the hybridization solution and hybridization was continued at 42° C. for a further 16 hours. The filters were then washed in 2×SSC, 1% w/v SDS at 42° C. for 2×30 minutes followed by a wash in 0.2×SSC, 1% w/v SDS at 65° C. for 30 minutes and exposed to Kodak XAR film with an intensifying screen at ¥70° C. for 4 hours.

Figure 3:
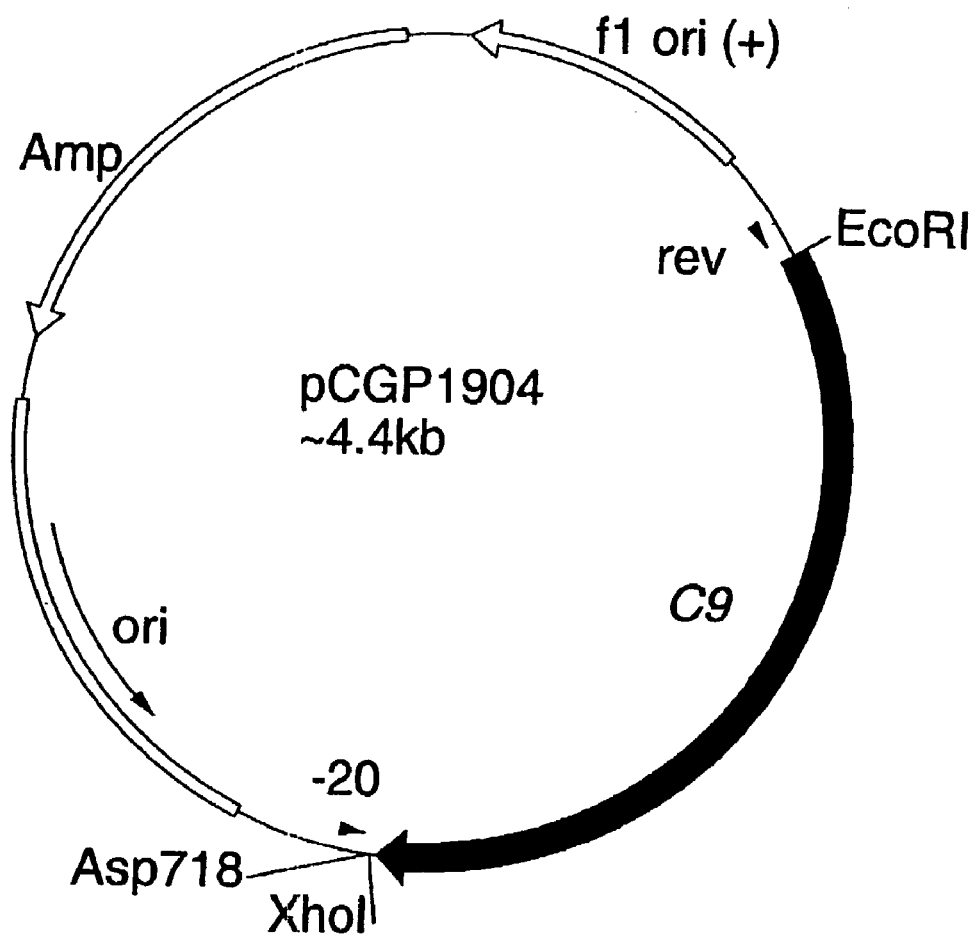
FIG. 3 is a diagrammatic representation of the plasmid pCGP1904 containing the C9 cDNA clone from *P. hybrida*. Abbreviations are as follows: Amp=the ampicillin resistance gene, fl ori (+)=fl filamentous phage origin of replication, ColE1ori=plasmid origin of replication, rev=approximate location of the M13 reverse primer site used in sequence analysis, −20=approximate location of the M13 −20 primer site used in sequence analysis. A selection of restriction endonuclease recognition sites are also marked.

Ten hybridizing plaques (designated as C1 to C10) were picked into PSB. These were rescreened to isolate pure clones, using the hybridization conditions as described for the initial screening of the cDNA library. The plasmids contained in the λZAP bacteriophage vector were rescued and sequence data was generated from the 3' and 5' ends of the cDNA inserts. Of these C9 represented the longest cDNA clone (~1.4 kb) and the plasmid was designated pCGP1904 (FIG. 3).

The complete sequence of the C9 cDNA clone (SEQ ID NO:1) (contained in pCGP1904) was determined by compilation of sequence from different pUC18 subclones obtained using standard procedures for the generation of randomly-overlapping clones (Sambrook et al., 1989). The sequence contained a putative open reading frame of 1371 bases which encodes a putative polypeptide of 457 amino acids (SEQ ID NO:2).

EXAMPLE 6

Acyltransferase Activity of the C9 cDNA Clone Expressed in Yeast

A yeast expression system was used to determine whether the C9 cDNA clone coded for an acyltransferase enzyme that was able to acylate the rutinoside attached to a flavonoid molecule.

Construction of pCGP912

Figure 4:
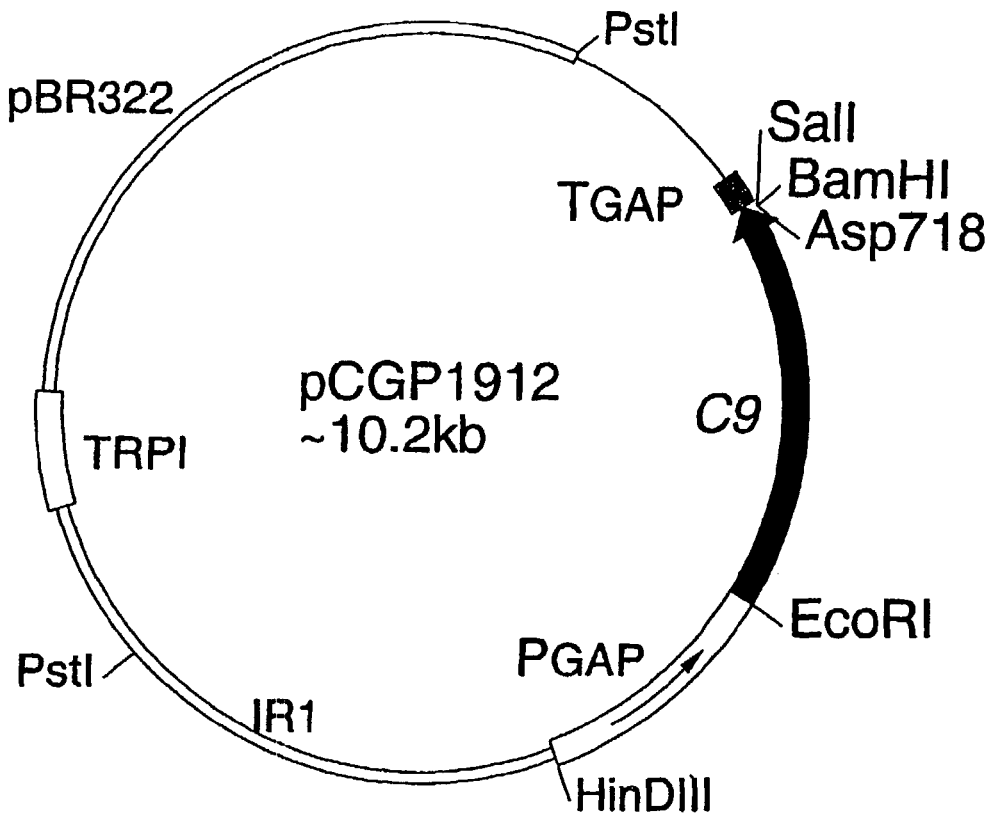
FIG. 4 is a diagrammatic representation of the yeast expression plasmid pCGP1912. The C9 cDNA insert from pCGP1904 was cloned in a sense orientation behind the yeast glyceraldehyde 3-phosphate dehydrogenase promoter (PGAP) in the expression vector pYE22m. Abbreviations are as follows: TRP1=Trp1 gene, TGAP=terminator sequence from the yeast glyceraldehyde 3-phosphate dehydrogenase gene, IR1=inverted repeat of 2 μm plasmid, pBR322=origin of replication from *E. coli*. A selection of restriction endonuclease recognition sites are also marked.

The plasmid pCGP1912 (FIG. 4) was constructed by cloning the C9 cDNA insert from pCGP1904 (FIG. 3) in a sense orientation behind the yeast glyceraldehyde 3-phosphate dehydrogenase promoter of pYE22m (Tanaka et al., 1988).

The 1.4 kb C9 cDNA fragment was released upon digestion of the plasmid pCGP1904 with Asp718/EcoRI. The cDNA fragment was isolated and purified using a Bresaclean kit (Bresatec) and ligated with Asp718/EcoRI ends of pYE22m. The ligation was carried with an Amersham Ligation kit using conditions recommended by the manufacturer. Correct ligation of the insert in pYE22m was established by Asp718/EcoRI restriction endonuclease digestion of the plasmid DNA isolated from ampicillin-resistant yeast transformants.

Yeast Transformation

The yeast strain G-1315 (Mat α, trp1) (Ashikari et al., 1989) was transformed with pCGP1912 (FIG. 4) according to Ito et al. (1983). The transformants were selected by their ability to restore G-1315 to tryptophan prototrophy.

Acyltransferase Assay of Yeast Extracts

The reactions were set up as detailed in Table 3 and incubated for 1 hour at 30° C. Each reaction was stopped by the addition of 25 μL $CHCl_3:CH_3COOH$ (2:1) containing 5% HCOOH followed by vortexing the mixture. After centrifugation at 13,000 rpm for 5 minutes, the upper phase was collected and evaporated to dryness in a evacuated chamber centrifuge. The pellet was redissolved in 3 μL $H_2O:CH_3COOH$ (12:1) and 1.5 μL was spotted onto a TLC (thin-layer chromatography)-cellulose plate. The TLC plate was chromatographed in $CH_3COOH:HCl:H_2O$ (30:3:67).

TABLE 3

Set up and results of acyltransferase assays of crude petunia petal homogenate and transformed yeast extracts (AT-1 to AT-4)

| | Positive control Br140 | | AT-1 | | AT-2 | | AT-3 | | AT-4 | | Br140/ AT-1 | | Control | |
|---|---|---|---|---|---|---|---|---|---|---|---|---|---|---|
| Tube # | 1 | 2 | 3 | 4 | 5 | 6 | 7 | 8 | 9 | 10 | 11 | 12 | 13 | 14 |
| Homogenate (in μL) | 20 | 20 | 20 | 20 | 20 | 20 | 20 | 20 | 20 | 20 | 20 10 | 20 10 | — | — |
| D3R 2 mg/mL (in μL) | 5 | 5 | 5 | 5 | 5 | 5 | 5 | 5 | 5 | 5 | 5 | 5 | 5 | 5 |
| Caffeoyl CoA 2 mg/mL (in μL) | 10 | – | 10 | – | 10 | – | 10 | – | 10 | – | 10 | – | 10 | – |
| 100 nM $PO_4$ pH 8/5 mM 2 ME (in μL) | 15 | 25 | 15 | 25 | 15 | 25 | 15 | 25 | 15 | 25 | 5 | 15 | 35 | 45 |
| Results: Acylation | + | – | + | – | + | – | + | – | + | – | + | – | – | – |

Preparation of Yeast Extracts for Assay of Acyltransferase Activity

Four single isolates of G-1315/pCGP1912 (AT-1 to AT-4) were inoculated into 30 mL of Modified Burkholder's medium (20.0 g/L dextrose, 2.0 g/L L-asparagine, 1.5 g/L $KH_2PO_4$, 0.5 g/L $MgSO_4.7H_2O$, 0.33 g/L $CaCl_2$, 2 g/L $(NH_4)_2SO_4$, 0.1 mg/L KI, 0.92 g/L $(NH_4)_6Mo_7O_{24}.4H_2O$, 0.1 mg/L nitrilotriacetic acid, 0.99 mg/L $FeSO_4.7H_2O$, 1.25 mg/L EDTA, 5.47 mg/L $ZnSO_4.7H_2O$, 2.5 mg/L $FeSO_4.7H_2O$, 0.77 mg/L $MnSO_4.7H_2O$, 0.196 mg/L $CuSO_4.5H_2O$, 0.124 mg/L $Co(NH_4)_2(SO_4)_2.6H_2O$, 0.088 mg/L $Na_2B_4O_7.10H_2O$, 0.2 mg/L thiamine, 0.2 mg/L pyridoxine, 0.2 mg/L nicotinic acid, 0.2 mg/L pantothenate, 0.002 mg/L biotin, 10 mg/L inositol) and was subsequently incubated at 30° C. for 3 nights with gentle shaking. Cells were collected by centrifugation for 5 minutes at 5000 rpm and resuspended in 1 mL of 50 mM $PO_4$ (pH 7.5), 2 mM 2-β-mercaptoethanol. The cells were then homogenized using 20 strokes in a glass Dounce homogenizer. The homogenized suspension was centrifuged at 13,000 rpm for 10 minutes at 4° C.

Preparation of Petal Extract of Br140 (a Source of AR-AT)

To prepare a crude homogenate of the petunia AR-AT, one gram of petal tissue from Br140 was homogenized along with one gram of sand and 0.5 g PVP in 5 mL of 100 mM $PO_4$ pH 7.0/5 mM 2 βME (β-mercaptoethanol) using a mortar and pestle. The crude homogenate was filtered through miracloth and the filtrate was then centrifuged for 10 minutes at 13,000 rpm at 4° C. The supernatant was then passed through an NAP-5 column using 100 mM $PO_4$ pH 8.0/5 mM 2 βME. This crude homogenate was used in the acyltransferase activity assay described below in Table 3.

D3R=delphinidin 3-rutinoside, Br140 crude petal homogenate, AT-1 to AT-4=extracts of yeast transformed with pCGP1912, +=Acylated delphinidin 3-rutinoside observed on TLC (co-migrating with the products obtained from the reaction using crude petunia petal homogenate (Tube 1), –=Only delphinidin 3-rutinoside detected on TLC. No acylation observed.

The results showed that acylation was observed in the crude Br140 extract (positive control) and in the yeast extracts from AT-1 to AT-4, but only in the presence of caffeoyl Co-A (Tubes 1, 3, 5, 7, 9 and 11). No acylation was observed with D3R and caffeoyl CoA without addition of either the crude Br140 petal homogenate or extracts from yeast transformed with pCGP1912 (AT-1 to AT-4). The TLC results provided direct evidence that the C9 cDNA clone coded for an AR-AT that was able to acylate D3R utilizing caffeoyl CoA.

HPLC Analysis

The remaining 1.5 μL of sample was analyzed by HPLC using a Phenomenex Ultracarb 5 ODS (30) column (150×4.6 mm). The solvent system used was $CH_3CN:TFA:H_2O$ (21.6: 0.1:67) and a flow rate of 1 minute was used. The detector was at 520 nm and the peaks were collected manually.

TABLE 4

HPLC results showing the retention times of the peaks produced in the acyltransferase assays

| Tube # | Homogenate | D3R | Caffeoyl CoA | Peak 1 RT | Peak 2 RT | Peak 3 RT |
|---|---|---|---|---|---|---|
| 1 | Br140 | + | – | 1.363 | 1.807 | none |
| 2 | Br140 | + | + | 1.378 | 1.808 | 2.255 |

TABLE 4-continued

HPLC results showing the retention times of the peaks produced in the acyltransferase assays

| Tube # | Homogenate | D3R | Caffeoyl CoA | Peak 1 RT | Peak 2 RT | Peak 3 RT |
|---|---|---|---|---|---|---|
| 3 | AT-1 | + | − | 1.362 | 1.798 | none |
| 4 | AT-1 | + | + | 1.379 | 1.809 | 2.265 |
| 5 | AT-2 | + | − | 1.362 | 1.804 | none |
| 6 | AT-2 | + | + | 1.380 | 1.806 | 2.275 |

D3R = delphinidin 3-rutinoside,
Br140 = crude petal homogenate,
AT-1 to AT-4 = extracts of yeast transformed with pCGP1912,
+ = included in reaction,
− = not added to reaction,
RT = retention time in minutes.

D3R=delphinidin 3-rutinoside, Br140 =crude petal homogenate, AT-1 to AT-4=extracts of yeast transformed with pCGP1912, +=included in reaction, −=not added to reaction, RT=retention time in minutes.

HPLC analysis of D3R alone produced 2 distinct peaks with retention times of 1.3 and 1.9. These 2 peaks were collected and run on a TLC system. The 2 peaks comigrated and are thought to be isomers of D3R.

The HPLC analysis detected an extra peak with a retention time of 2.2 in reaction tubes containing D3R, caffeoyl CoA and either the petunia Br140 crude homogenate or the transformed yeast extract (Tubes 2, 4 and 6) (Table 4).

This provided evidence to suggest that the petunia C9 cDNA clone encoded an AR-AT which was able to acylate D3R as was the AR-AT enzyme contained in the petunia Br140 petal extract (positive control).

EXAMPLE 7

Acyltransferase Activity of the Petunia AR-AT (C9) cDNA Clone Expressed in *E. coli*

The C9 cDNA clone was also expressed in an *E. coli* expression system and assayed for AR-AT activity.

Generation of NcoI and BamHi Sites at 5' and 3' Ends, Respectively (Construction of pCGP3105)

In order to clone the petunia C9 clone (petunia AR-AT=PAR-AT) into an *E. coli* expression vector, pQE60 (QIAGEN), an NcoI site was required at the initiating ATG and a BamHI site was required just before the putative stop codon. The following oligonucleotides (Table 5) were designed to generate an NcoI site at the initiating ATG and a BamHI site just prior to the putative stop codon:

TABLE 5

| SEQ ID NO: | Name | Sequence |
|---|---|---|
| 4 | petatF | G AGA TAC ACC ATG GAT CAA AGT TTG |
| 5 | petatR | CG GGA TCC TTT TGG CAT AGA ACT AAA CTC |

The petatF (SEQ ID NO:4) and petatR (SEQ ID NO:5) oligonucleotides were used as primers along with pCGP1904 as template to amplify a petunia AR-AT clone with NcoI recognition site at the initiating AUG and BamHI recognition site just prior to the putative stop codon. The resulting PCR products were electrophoresed through a gel and fragments at around 1.2 kb were excised, purifed and then cloned into PCR-Script (STRATAGENE) following procedures recommended by the manufacturer. The resulting plasmid was designated pCGP3105 (mut PAR-AT).

The petatF (SEQ ID NO:4) oligonucleotide used in the PCR contained three bases that differed from the petunia AR-AT sequence. Thus, the sequence was changed from 5' G AGA TAC ATT ATG AAT CAA AGT TTG 3' to 5' G AGA TAC ACC ATG GAT CAA AGT TTG 3'. As a consequence the translated amino acids around the putative initiating Methionine were changed from RYIMNQ to RYTMDQ.

Cloning into pQE60 Vectors (Construction of pCGP3106)

The cloned PCR product contained in pCGP3105 was released upon digestion with NcoI and BamHI. The resulting 1.4 kb fragment was isolated on a gel, excised, purified and then ligated with NcoI/BamHI ends of pQE60 vector (QIAGEN) according to the manufacturer's recommendations. Transformants were analyzed for the presence of the specific 1.4 kb insert using a number of restriction endonuclease digests. The resulting plasmid was designated pCGP3106 (petunia AR-AT in pQE60).

Acyltransferase Activity

The activity of the petunia C9 clone in pCGP3106 was assessed on the substrates delphinidin 3-glucoside and delphinidin 3-rutinoside using assay conditions as described in Fujiwara et al., 1997 (Table 6).

TABLE 6

Results of acyltransferase assays of extracts of *E. coli* containing pCGP3106 or pQE60 control vector using delphinidin 3-rutinoside or delphinidin 3-glucoside as substrate.

|  | D3R | D3G |
|---|---|---|
| pQE60 vector control + caffeoyl CoA | − | − |
| pQE60 vector control + coumaroyl CoA | − | nd |
| pCGP3106 + caffeoyl CoA | + | − |
| pCGP3106 + coumaroyl CoA | + | nd |

D3R = delphinidin 3-rutinoside
D3G = delphinidin 3-glucoside
nd = not done
+ = acylation of the substrate occurred as observed by a new peak on the HPLC
− = no reaction observed, only substrate observed on HPLC The results obtained with expression of the C9 cDNA clone in an *E. coli* expression system provide further evidence to suggest that the C9 cDNA clone from petunia codes for an AR-AT that is able to acylate delphinidin 3-rutinoside using either caffeoyl Co-A or coumaroyl Co-A as an acyl donor. There was no activity observed when delphinidin 3-glucoside was used as substrate.

EXAMPLE 8

Antisense Expression of AR-AT in Plants

Construction of pCGP40

Plasmid pCGP40 was constructed by removing the GUS gene (Jefferson et al., 1987) as a BamHI-SacI fragment from pCGN7334 and replacing it with the BamHI-SacI fragment from pBluescribe M13⁻ that includes the multicloning site. Plasmid pCGN7334, obtained from Calgene Inc. (California, USA), was constructed by inserting the fragment containing the Mac-GUS-mas gene fusion into the XhoI site of pCGN7329 (Comai et al., 1990).

Construction of pCGP1909 and pCGP9117

Figure 5:
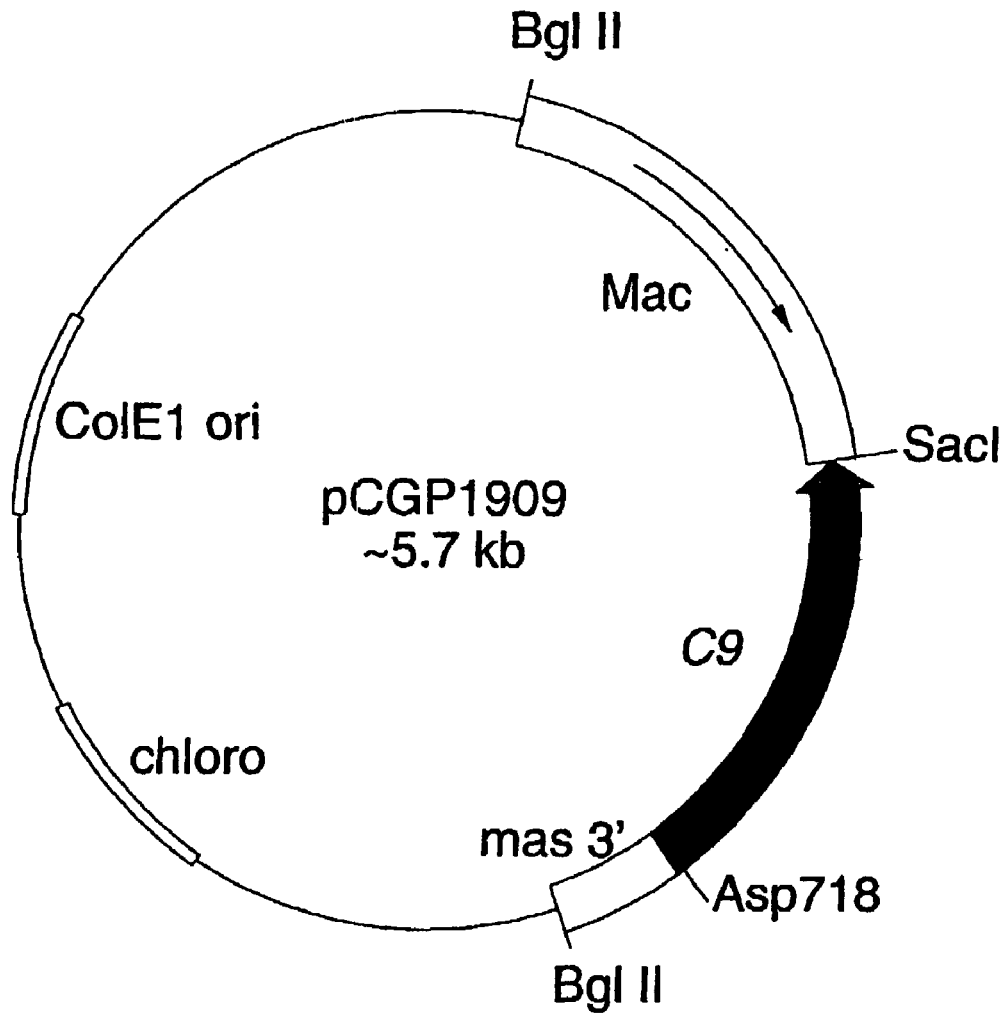
FIG. 5 is a diagrammatic representation of the expression plasmid pCGP1909. The petunia AR-AT cDNA insert (C9) from pCGP1904 was cloned in an antisense orientation behind the Mac promoter of the expression vector pCGP40. Abbreviations are as follows: chloro=chloramphenicol resistance gene, mas 3'=the terminator region from the mannopine synthase (mas) gene of *Agrobacterium*, Mac=Hybrid promoter consisting of the promoter from the mas gene and an enhancing seqeunce from the cauliflower mosaic virus 35S (CaMV35S) promoter, oriColE1=a high copy origin of replication from a Colcinin E1 plasmid. A selection of restriction endonuclease recognition sites are also marked.

Plasmid pCGP1909 (FIG. 5) was constructed by cloning the cDNA insert from pCGP1904 (FIG. 3) in an antisense orientation behind the Mac promoter (Comai et al., 1990) of pCGP40. The GUS coding region in pCGP40 was removed upon digestion with SacI/Asp718. The vector containing the Mac promoter and mas terminator was purified using GeneClean Kit (Bresatec) and ligated with SacI/Asp718 ends of the C9 cDNA fragment released from pCGP1904. The ligation was carried out using the Amersham ligation kit using conditions recommended by the manufacturer. Correct insertion of the C9 insert in pCGP1909 was established by SacI/Asp718 restriction analysis of DNA isolated from chloramphenicol-resistant transformants.

Figure 6:
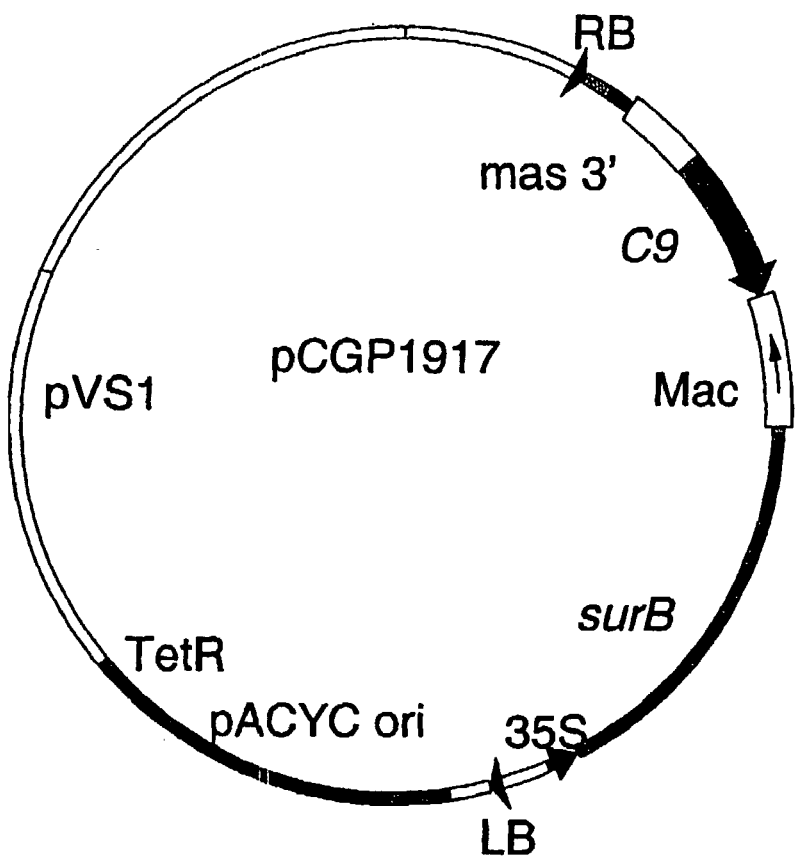
FIG. 6 is a diagrammatic representation of the binary plasmid pCGP1917. The chimaeric antisense AR-AT gene from pCGP1909 was cloned into the binary vector pWTT2132 (DNA Plant Technology) in a tandem orientation with the chimaeric surB gene. Abbreviations are as follows: Tet=the tetracycline resistance gene; LB=left border; RB=right border; surB=the coding region and terminator sequence from the acetolactate synthase gene from tobacco; 35S=the promoter region from the cauliflower mosaic virus 35S gene, mas 3'=the terminator region from the mannopine synthase gene of *Agrobacterium*; pVS1=a broad host range origin of replication from a plasmid from *Pseuodomonas aeruginosa*, pACYCori=modified replicon from pACYC184 from *E. coli*. A selection of restriction endonuclease recognition sites are also marked.

Plasmid pCGP1917 (FIG. 6) was constructed by cloning Mac-C9-mas gene fusion from pCGP1909 (FIG. 5) into the binary vector pWTT2132 (DNAP). The C9 chimaeric gene was isolated from pCGP1909 upon restriction with BglII and the resulting 5' overhang was repaired using the Klenow fragment of DNA polymerase I. The C9 chimaeric gene was purified using a Bresaclean Kit (Bresatec) and was ligated with pWTT2132 that had been restricted with SmaI and then dephosphorylated. Correct insertion of the insert in pCGP1917 was established by Asp718 restriction endonuclease digestion of DNA isolated from tetracycline resistant *E. coli* transformants.

*A. tumefaciens* Transformations with pCGP1917

Plasmid pCGP1917 (FIG. 6) was introduced into the *Agrobacterium tumefaciens* strain AGL0 by adding 5 μg of plasmid DNA to 100 μL of competent AGL0 cells. (Competent AGL0 cells were prepared by inoculating a 50 mL MG/L (Garfinkel and Nester, 1980) culture and growing for 16 hrs with shaking at 28° C. The cells were then pelleted and resuspended in 0.5 mL of 85% v/v 100 mM $CaCl_2$/15% v/v glycerol.

The DNA-Agrobacterium mixture was frozen by incubation in liquid $N_2$ for 2 minutes and then allowed to thaw by incubation at 37° C. for 5 minutes. The DNA/bacterial mix was then placed on ice for a further 10 minutes. The cells were then mixed with 1 mL of MG/L media and incubated with shaking for 16 hours at 28° C. Cells of *A. tumefaciens* carrying pCGP1917 were selected on MG/L agar plates containing 50 μg/mL tetracycline. The presence of pCGP1917 was confirmed by Southern analysis of DNA isolated from the tetracycline-resistant *A. tumefaciens* transformants.

Antisense Suppression of AR-AT Activity in *P. hybrida*

The T-DNA of the plasmid pCGP1917 (FIG. 6) was introduced into *P. hybrida* cv. VR via Agrobacterium-mediated transformation in order to reduce the level of the petunia AR-AT activity and, therefore, modify the types of anthocyanin accumulating and the flower colours produced.

*P. hybrida* Transformations (a) Plant Material

Leaf tissue from mature plants of *P. hybrida* cv VR was sterilized in 1.25% w/v sodium hypochlorite for 2 minutes and then rinsed three times in sterile water. The leaf tissue was then cut into 25 $mm^2$ squares and precultured on MS media (Murashige and Skoog, 1962) supplemented with 0.05 mg/L kinetin and 1.0 mg/L 2,4-dichlorophenoxyacetic acid (2,4-D) for 24 hours.

(b) Co-Cultivation of *Agrobacterium* and *Petunia* Tissue

*A. tumefaciens* strain AGL0 (Lazo et al., 1991) containing the binary vector pCGP1917 (FIG. 6) was maintained at 4° C. on MG/L (Garfinkel and Nester, 1980) agar plates with 50 mg/L tetracycline. A single colony was grown overnight in liquid medium containing 1% w/v Bacto-peptone, 0.5% w/v Bacto-yeast extract and 1% w/v NaCl. A final concentration of $5 \times 10^8$ cells/mL was prepared the next day by dilution in liquid MS medium containing B5 vitamins (Gamborg et al., 1968) and 3% w/v sucrose (BPM). The leaf discs were dipped for 2 minutes into BPM containing AGL0/pCGP1917 as described above. The leaf discs were then blotted dry and placed on co-cultivation media for 4 days. The co-cultivation medium consisted of SH medium (Schenk and Hildebrandt, 1972) supplemented with 0.05 mg/L kinetin and 1.0 mg/L 2,4-D and included a feeder layer of tobacco cell suspension spread over the co-cultivation medium with a filter paper placed on top of the tobacco cell suspension.

(c) Recovery of Transgenic *Petunia* Plants

After co-cultivation, the leaf discs were transferred to MS medium supplemented with 3% w/v sucrose, 1 mg/L α-benzylaminopurine (BAP), 0.1 mg/L α-naphthalene acetic acid (NAA), 2 μg/L Chlorsulfuron (Chem Service), 350 mg/L cefotaxime and 0.3% w/v Gelrite Gellan Gum (Schweizerhall) (selection medium). Regenerating explants were transferred to fresh selection medium after 4 weeks. Adventitious shoots which survived the Chlorsulfuron selection were isolated and transferred to BPM containing 2 μg/L Chlorsulfuron (Chem Service) and 200 mg/L cefotaxime for root induction. All cultures were maintained under a 16 hr photoperiod (60 μmol. $m^{-2}$, $s^{-1}$ cool white fluorescent light) at 23±2° C. When roots reached 2–3 cm in length the transgenic petunia plantlets were transferred to autoclaved Debco 51410/2 potting mix in 8 cm tubes. After 4 weeks plants were replanted into 15 cm pots using the same potting mix and maintained at 23° C. under a 14 hour photoperiod (300 μmol $m^{-2}$, $s^{-1}$ mercury halide light).

Transgenic Analysis of pCGP1917/VR *Petunia* Plants

Twenty-two independent transgenic plants were produced and grown to flowering. A selection of plants produced flowers with dark pink sectors which differed to the purple coloured VR control. A selection of flower colours observed is shown in Table 7. The pigments accumulating in the flowers of the transgenic plants were analyzed by TLC (thin-layer chromatography).

TABLE 7

Petal colours of VR, SD controls and 1917/VR transgenic flowers.

| Accession Number | RHSCC Code | Petal Colour |
|---|---|---|
| VR control | 78a/80a | purple |
| SD control | 63b/c | dark pink |
| 9327 | Variegated 78a and 63b or 86b sectors | Variegated purple and dark pink sectors |
| 9283 | 78a | purple (VR-like) |

RHSCC = Royal Horticultural Society Colour Chart (Kew, UK).
SD control = Skr4 × Da hybrid that accumulates delphinidin-based pigments (Brugliera et al., 1994).

The codes are taken from the Royal Horticultural Society's Colour Chart (Kew, UK). They provide an alternative means by which to describe the colour phenotypes observed. The designated numbers, however, should be taken only as a guide to the perceived colours and should not be regarded as limiting the possible colours which may be obtained.

Extraction of Anthocyanins and Flavonols

Prior to TLC analysis, the anthocyanin and flavonol molecules present in petal and stamen extracts were acid hydrolyzed to remove glycosyl moieties from the anthocyanidin or flavonol core. Anthocyanidin and flavonol standards were used to help identify the compounds present in the floral extracts.

Anthocyanins and flavonols were extracted and hydrolyzed by boiling between 100 to 200 mg of petal limbs, or five stamens, in 1 mL of 2 M hydrochloric acid for 30 minutes. The hydrolyzed anthocyanins and flavonols were extracted with 200 µL of iso-amylalcohol. This mixture was then dessicated under vacuum and resuspended in a smaller volume of methanol/1% v/v HCl. The volume of methanol/1% v/v HCl used was based on the initial fresh weight of the petal so that the relative levels of flavonoids in the petals could be estimated. Extracts from the stamens were resuspended in 1 µL of methanol/1% v/v HCl. A 1 µL aliquot of the extracts from the pCGP1917 in VR petals was spotted onto a TLC plate.

TLC Analysis of Floral Extracts

Figure 1B:
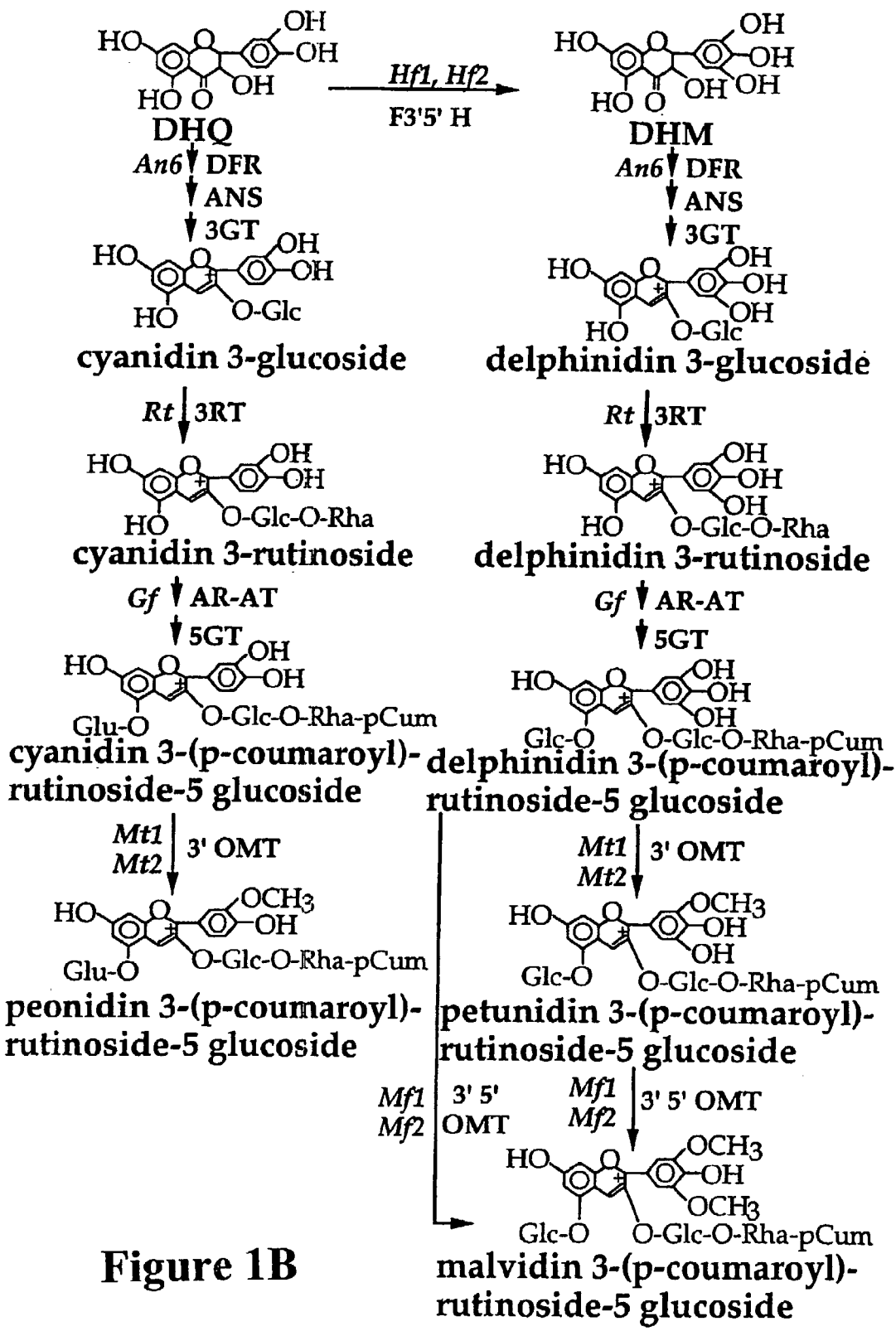

Acid-hydrolyzed floral extracts were run in a Forestal solvent system (HOAc:water:HCl; 30:10:3) (Markham, 1982). TLC analysis of the acid-hydrolyzed petal extracts revealed that 8 of the 22 independent events produced petals that accumulated delphinidin along with petunidin and malvidin. VR petals predominantly accumulate malvidin-based pigments (FIG. 1b). Suppression of AR-AT activity in petunia would lead to an accumulation of delphinidin based pigments. The transgenic data provides evidence that antisense expression of the petunia AR-AT sequence did suppress AR-AT activity and lead to the production of delphinidin-based pigments in a line that normally produces malvidin pigments. The flowers of the transgenics that produced delphinidin-based pigments (along with petunidin and malvidin-based pigments) were of a mottled appearance with sectors of purple "VR-like" colour and sectors of a dark pink colour (Table 7).

EXAMPLE 9

Isolation of AR-AT cDNA Clone From *Nierembergia*

Preparation of a *Nierembergia* Petal cDNA Library

A λZAPII (EcoRI/XhoI directional) kit (Stratagene) was used to prepare a petal cDNA library from RNA isolated from petals of opening buds of *Nierembergia* sp. Cv. Fairy Bells (Suntory Ltd.) according to the conditions recommended by the manufacturer.

Figure 7:
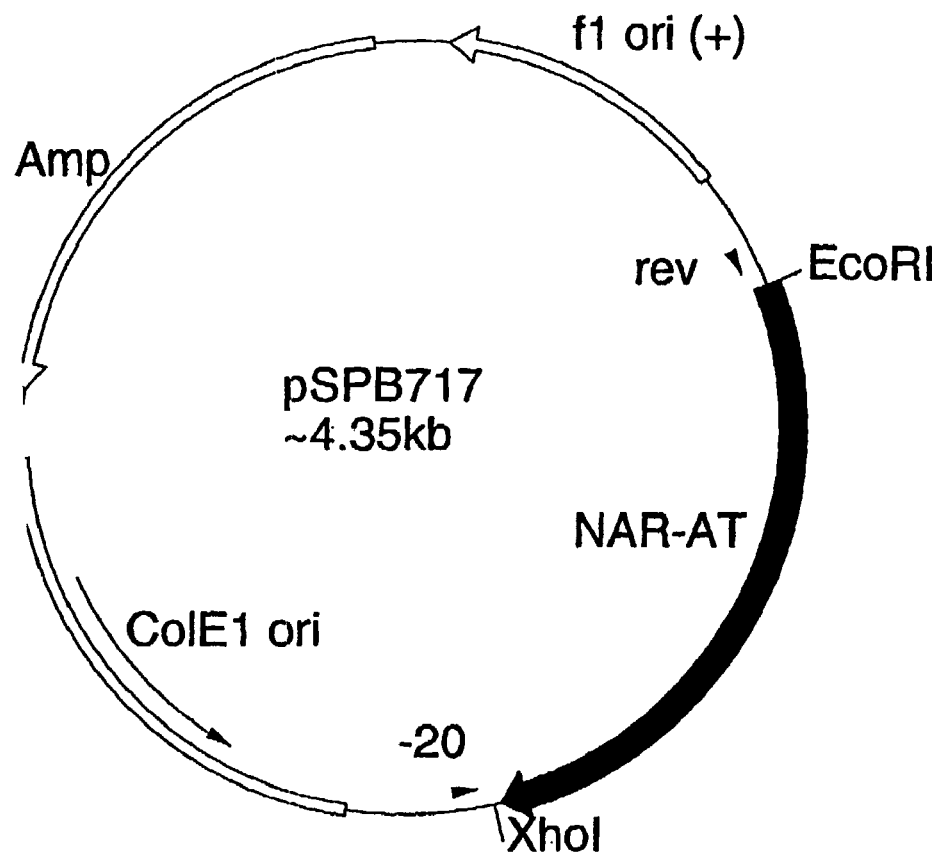
FIG. 7 is a diagrammatic representation of the plasmid pSPB717 containing the NAR-AT cDNA clone from *Nierembergia* spp. cv. Fairy Bells Abbreviations are as follows: Amp=the ampicillin resistance gene, fl ori (+)=fl filamentous phage origin of replication, ColE1ori=plasmid origin of replication, rev=approximate location of the M13 reverse primer site used in sequence analysis, −20=approximate location of the M13 −20 primer site used in sequence analysis. A selection of restriction endonuclease recognition sites are also marked.

About 200,000 pfus were screened with DIG-labelled petunia AR-AT (C9) cDNA clone from pCGP1904 (FIG. 3) using low stringency conditions as described by Tanaka et al., 1996. Twenty hybridizing plaques were picked into PSB. They were rescreened to isolate purified plaques, using the hybridization conditions as described for the initial screening of the cDNA library. The plasmids contained in the λZAPII bacteriophage vector were rescued and sequence data was generated from the 3' and 5' ends of the cDNA inserts. Of these NAR-AT represented the longest cDNA clone (~1.7 kb) and the plasmid was designated as pSPB717 (FIG. 7).

The complete sequence of the NAR-AT cDNA clone (SEQ ID NO:6) was determined by compilation of sequence from different pUC18 subclones obtained using standard procedures for the generation of randomly-overlapping clones (Sambrook et al., 1989). The sequence contained a putative open reading frame of 1365 bases which encodes a putative polypeptide of 455 amino acids (SEQ ID NO:7). The deduced amino acid sequence of the NAR-AT clone shared 85% identity at the amino acid level with that of the petunia AR-AT clone (SEQ ID NO: 2).

EXAMPLE 10

Isolation of AR-AT cDNA Clones From *Viola* spp

Preparation of Pansy Petal cDNA Libraries

A λZAPII (EcoRI/XhoI directional) kit (Stratagene) was used to prepare 2 petal cDNA libraries. One from RNA isolated from petals of opening buds of *Viola* spp. cv. black pansy and the other from RNA isolated from petals of opening buds of *Viola* spp. cv. light blue pansy according to the conditions recommended by the manufacturer. The total number of recombinants were: $1.7 \times 10^6$ pfu (black pansy) and $1.8 \times 10^6$ pfu (light blue pansy).

PCR of AT Sequences From Black and Light Blue Pansy

CODEHOP Design of Primers for PCR of AT Sequences From Pansy

In order to isolate AR-AT sequences from pansy, oligonucleotide primers were designed to areas of amino acid sequence similarity between the acyltransferases that acylate the 3 or 5-glucose of anthocyanidin 3-glucoside or anthocyanidin 3,5-diglucoside (International Patent Application No. PCT/JP96/00348 (International Patent Publication No. WO 96/25500)) and the *Petunia* and *Nierembergia* AR-AT sequences that are able to acylate the rhamnose group on anthocyanidin 3-rutinosides.

The CODEHOP(COnsensus-DEgenerate Hybrid Oligonucleotide Primers) strategy (Rose et al., 1998) (outlined at http://blocks.fhcrc.org/codehop.html) was used. The CODEHOP program designs a pool of primers containing all possible 11- or 12-mers for a 3' degenerate "core" region and having the most probable nucleotide predicted for each position in a 5' non-degenerate "clamp" region (Table 8).

TABLE 8

Oligonucleotides designed to areas of sequence similarity between acyltransferase sequences identified by the CODEHOP program

| SEQ ID NO: | Name | Sequence (5' to 3') |
|---|---|---|
| 8 | ATf1 | CCT ACT ACT AAT CAT GAA CAA TCT TAT CCT CTT wsn tty tty ga |
| 9 | ATf2 | CTT GAT CCT CCT GAA CCT CAA AAT TAn tty ggn aay t |

TABLE 8-continued

Oligonucleotides designed to areas of sequence similarity between acyltransferase sequences identified by the CODEHOP program

| SEQ ID NO: | Name | Sequence (5' to 3') |
|---|---|---|
| 10 | ATf3 | TCT TGT AGA TTT CAT CTT TAT GAT TGT GAy tty ggn tgg g |
| 11 | Atr3 | G CCA AAT AGG CTT TCC Cca ncc raa rtc | where R = A or G,
Y = C or T,
M = A or C,
K = G or T,
S = G or C,
W = A or T,
H = A or C or T,
B = G or C or T,
V = A or G or C,
D = A or G or T,
N = A or G or C or T,
I = deoxyinosine.

TABLE 9

Other oligonucleotides designed for use in PCR of AR-AT sequences

| SEQ ID NO: | Name | Sequence (5' to 3') |
|---|---|---|
| 12 | dT(17)Ad2Ad1 | CTG AGA GAA CTA GTC TCG AGC TCT AGA ACA AGC TTT TTT TTT TTT |
| 13 | GI-anchor | GGC CAC GCG TCG ACT AGT ACG GGI IGG GII GGG IIG |

I = deoxyinosine

Total RNA was prepared from black pansy petal buds (stage 3) using the Plant RNAeasy kit (QIAGEN). One microgram of RNA was used as a template to prepare cDNA using Superscript II (Stratgene) and the dT(17)Ad2Ad1 (SEQ ID NO:12) (Table 9) oligonucleotide using conditions as recommended by the manufacturer. The cDNA was purified by passing it through a PCR purification column (QIAGEN) and eluting in 50 µL 10 Mm Tris-HCl, pH 8.5. The cDNA was subsequently C-tailed using terminal transferase (Boehringer Mannheim) using conditions recommended by the manufacturer. The C-tailed cDNA was then purified through a PCR purification column (QIAGEN) and eluted in 50 µL 10 mM Tris-HCl, pH 8.5.

The C-tailed cDNA (1 µL) was subsequently used as template in a PCR with 2.5 µL 10×HotSTART QIAGEN buffer, 4 µL 1.25 mM dNTP, 5 µL 50 ng/µL primer Atr3 (SEQ ID NO:11), 5 µL 50 ng/µL GI-anchor primer (SEQ ID NO:13) (Table 9), 2 µL pure water and 0.5 µL HotSTART Taq polymerase (QIAGEN). The reaction was heated to 95° C. for 15 minutes then run through 35 cycles of 94° C. for 30 seconds, 50° C. for 30 seconds, 72° C. for 90 seconds, followed by 72° C. for 10 minutes.

The PCR products were electrophoresed through a 1% w/v agarose gel and the expected 1.2 kb products were excised and purified. The 1.2 kb fragments were ligated with pCR7 2.1 (Invitrogen). A random selection of 18 transformants of the black pansy petal PCR products were analyzed for the presence of inserts by digesting with EcoRI. Seven transformants that contained inserts of the expected 1.2 kb size (BPAR-AT 2, 3, 5, 9, 10, 14 and 15) were sequenced using the M13 Reverse and M13 Forward -21 primers.

The putative translated sequences of BPAR-AT 2, 3, 5, 9, 10, 14 and 15 all contained conserved amino acid motifs that are found in acyltranferases isolated to date (St-Pierre and De Luca, 2000). However, the deduced amino acid sequence of BPAR-AT 2 and BPAR-AT 3 closely aligned with that of the petunia AR-AT sequence (SEQ ID NO:3) and were selected for further analysis.

Figure 8:
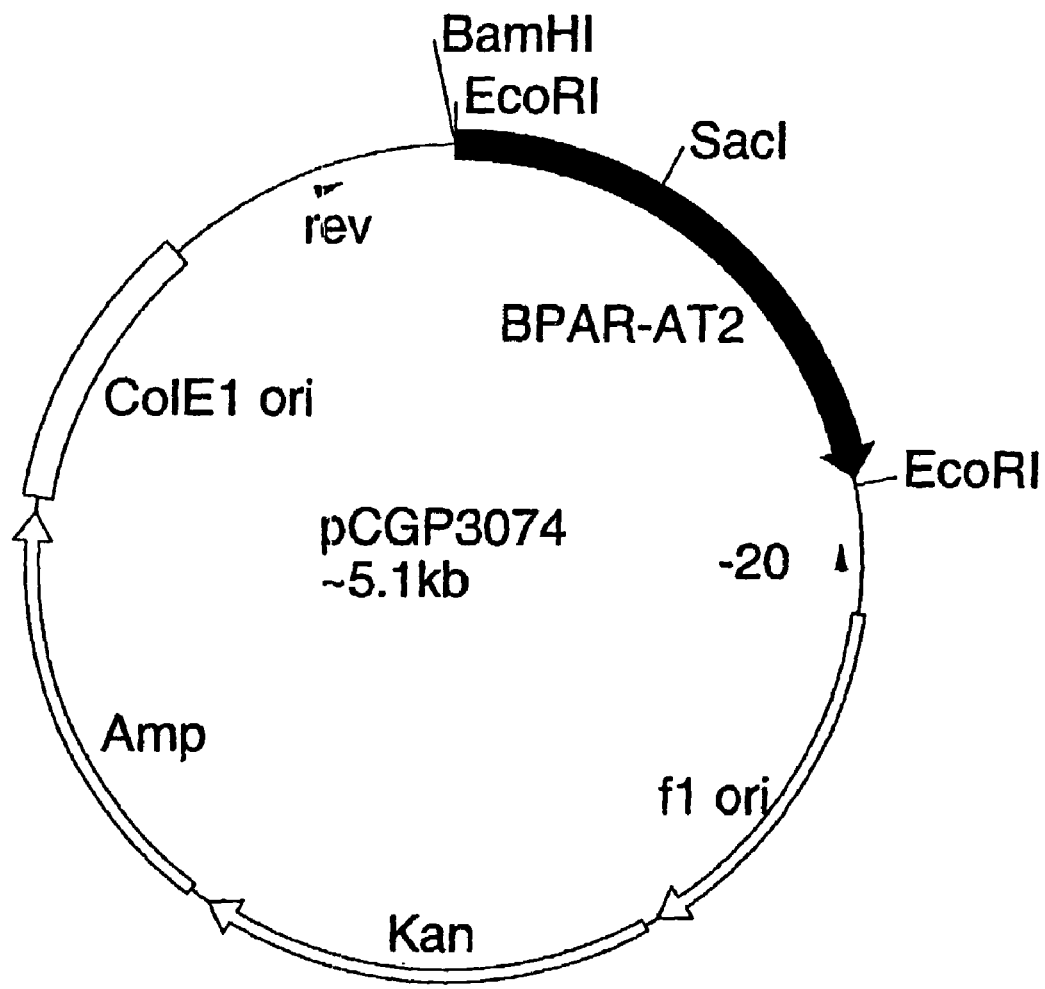
FIG. 8 is a diagrammatic representation of the plasmid pCGP3074 containing the BPAR-AT2 PCR product from *Viola* spp. cv. black pansy in a pCR 2.1 vector. Abbreviations are as follows: Amp=the ampicillin resistance gene, Kan=kanamycin resistance gene, fl ori=fl filamentous phage origin of replication, ColE1ori=plasmid origin of replication, rev=approximate location of the M13 reverse primer site used in sequence analysis, −20=approximate location of the M13 −20 primer site used in sequence analysis. A selection of restriction endonuclease recognition sites are also marked.
Figure 9:
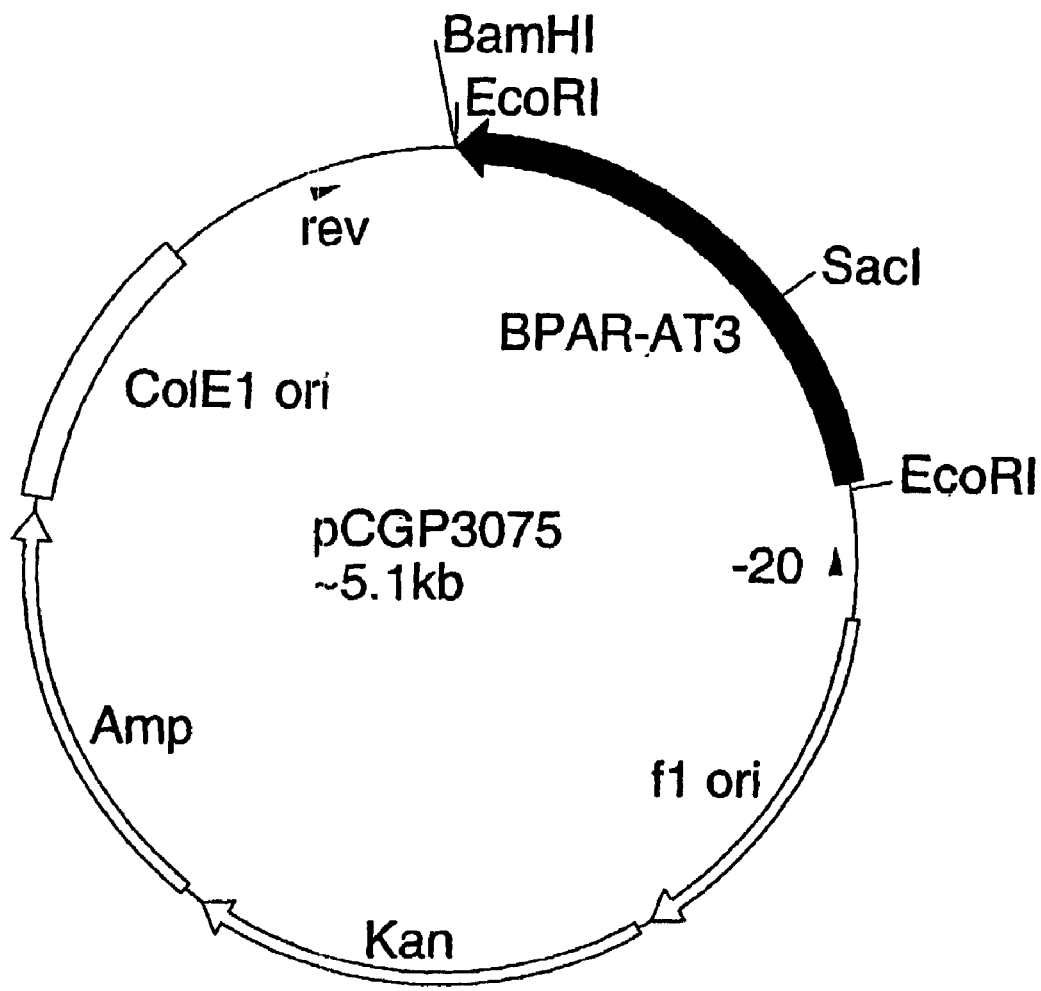
FIG. 9 is a diagrammatic representation of the plasmid pCGP3075 containing the BPAR-AT3 PCR product from *Viola* spp. cv. light blue pansy in a pCR 2.1 vector. Abbreviations are as follows: Amp=the ampicillin resistance gene, Kan=kanamycin resistance gene, fl ori=fl filamentous phage origin of replication, ColE1ori=plasmid origin of replication, rev=approximate location of the M13 reverse primer site used in sequence analysis, −20=approximate location of the M13 −20 primer site used in sequence analysis. A selection of restriction endonuclease recognition sites are also marked.

The BPAR-AT2 plasmid was designated pCGP3074 (FIG. 8) and the BPAR-AT3 plasmid as pCGP3075 (FIG. 9). Complete sequence of the 1.2 kb BPAR-AT2 (SEQ ID NO:14) and BPAR-AT3 (SEQ ID NO:16) PCR products was generated using specific oligonucleotides (SEQ ID NO:18 (BPAR-AT2F), SEQ ID NO:19 (BPAR-AT2R), SEQ ID NO:20 (BPAR-AT3F), SEQ ID NO:21 (BPAR-AT3R) designed to the sequence generated by the M13 reverse and M13 -21 primers (Table 10). BPAR-AT2 and 3 shared 95% identity at the nucleotide level and 93% identity at the amino acid level.

TABLE 10

Oligonucleotides designed to generate complete sequence of the BPAR-AT2 and BPAR-AT3 clones.

| SEQ ID NO: | Name | Sequence (5' to 3') |
|---|---|---|
| 18 | BPAT2F | CGT CGA AGC TCG AGT GGA G |
| 19 | BPAT2R | GTT TAA GGG CAA CAG GTT CTG |
| 20 | BPAT3F | CAG GTT CTG ATC TGC GTC |
| 21 | BPAT3R | CAA GTA GTA AGT TCA CTC CC |

The putative translated sequences of BPAR-AT 2 and BPAR-AT 3 were compared with the petunia AR-AT sequence using LFASTA (Table 11).

TABLE 11

Percentage sequence identity of the putative translated sequences of BPAR-AT PCR clones 2 and 3 with that of the petunia AR-AT.

|  | Petunia AR-AT (457 aa) |
| --- | --- |
| BPAR-AT2 | 28% (414 aa overlap) |
| BPAR-AT3 | 27% (400 aa overlap) |

Expression of BPAR-AT2 in Black Pansy

The developmental expression profiles in black pansy petals and leaves were determined by using the $^{32}$P-labelled fragments of a 1.2 kb EcoRI fragment from pCGP3074 (BPAR-AT2) (FIG. 8) as a probe against an RNA blot containing 10 μg of total RNA isolated from each of the five black pansy petal developmental stages as well as from black pansy leaves.

Total RNA was isolated from black pansy petal (stages 1 through 5) and leaf tissue using the method of Turpen and Griffith (1986).

RNA samples were electrophoresed through 2.2 M formaldehyde/1.2% w/v agarose gels using running buffer containing 40 mM morpholinopropanesulphonic acid (pH 7.0), 5 mM sodium acetate, 0.1 mM EDTA (pH 8.0). The RNA was transferred to Hybond-N filters (Amersham) as described by the manufacturer.

The RNA blot was probed with $^{32}$P-labelled fragments of a 1.2 kb EcoRI fragment from pCGP3074 (BPAR-AT2) (FIG. 8) ($10^8$ cpm/μg, $2 \times 10^6$ cpm/mL). Prehybridization (1 hour at 42° C.) and hybridization (16 hours at 42° C.) were carried out in 50% v/v formamide, 1 M NaCl, 1% w/v SDS, 10% w/v dextran sulphate. The filter was washed in 2× SSC, 1% w/v SDS at 65° C. for 1 to 2 hours and then 0.2×SSC, 1% w/v SDS at 65° C. for 0.5 to 1 hour. The filter was exposed to Kodak XAR film with an intensifying screen at −70° C. for 0.5 hours followed by an exposure of 16 hours.

Figure 10:
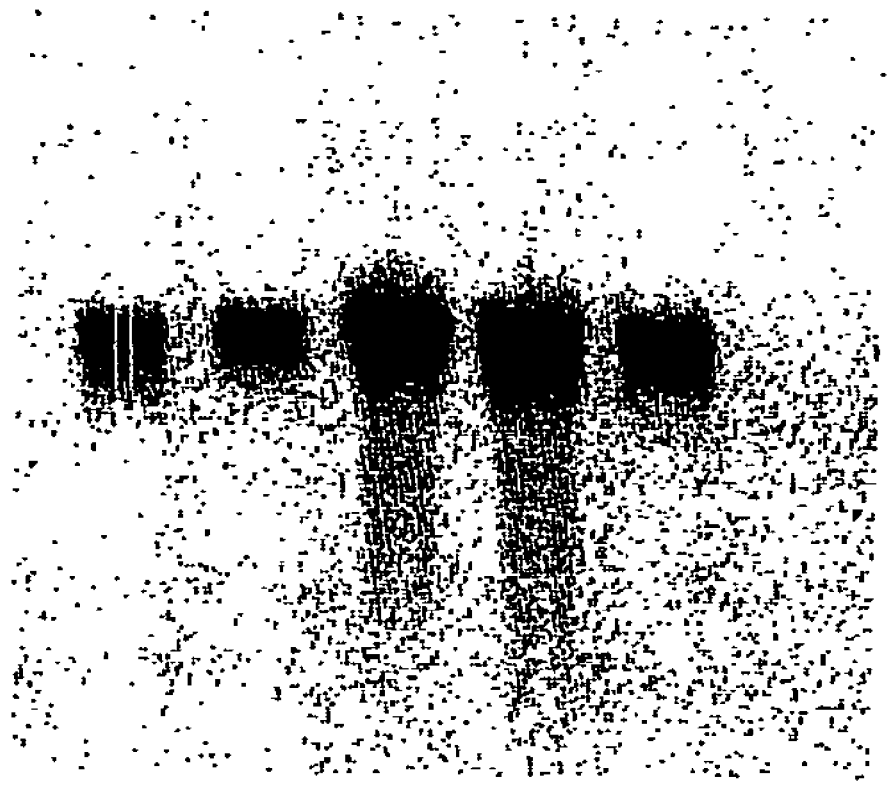
FIG. 10 is a representation of an autoradiograph of an RNA blot probed with $^{32}$P-labelled fragments of a 1.2 kb EcoRI fragment of the BPAR-AT2 clone contained in pCGP3704. Each lane contained a 10 μg sample of total RNA isolated from the flowers or leaves of plants of a *Viola* spp. cv. black pansy. A 1.4 kb transcript was detected in the petals of the black pansy. Under conditions used no transcript was detected in the leaves of the black pansy (L).

The BPAR-AT2 probe hybridized with a ~1.4 kb transcript in all stages of pansy flower development and peaked at around stage 3 of flower development. Under the conditions used, no hybridizing transcript was detected by Northern analysis of total RNA isolated from leaf (FIG. 10).

The AR-AT transcripts of black pansy would be expected to be most abundant in petals and have no or reduced levels in leaves consistent with the expression profiles of most anthocyanin biosynthetic genes (see Brugliera et al., 1994; Brugliera et al., 1999; Holton et al., 1993). These results are consistent with the expectation that BPAR-AT2 represents an AR-AT transcript that would be most abundant in petals and reduced in leaves.

Isolation of AR-AT Sequences From Light Blue Pansy

A PCR was also set up using RNA isolated from light blue pansy petals according to the conditions described above for the black pansy isolation. The 1.2 kb PCR products were ligated with pCR7 2.1 (Invitrogen). Transformants were patched onto fresh LB plates containing 100 μg/mL of ampicillin. Colony lifts were taken onto Colony/Plaque Screen ™ filters (DuPont) and treated as recommended by the manufacturer.

Prior to hybridization, the duplicate plaque lifts were washed in prewashing solution (50 mM Tris-HCl pH 7.5, 1 M NaCl, 1 mM EDTA, 0.1% w/v sarcosine) at 65° C. for 30 minutes; stripped in 0.4 M sodium hydroxide at 65° C. for 30 minutes; then washed in a solution of 0.2 M Tris-HCl pH 8.0, 0.1×SSC, 0.1% w/v SDS at 65° C. for 30 minutes and finally rinsed in 2×SSC, 1.0% w/v SDS.

The colony lifts of the transformants were screened with $^{32}$P-labelled fragments of a 1.2 kb EcoRI fragment from pCGP3075 (3PAR-AT3) (FIG. 9).

Hybridization conditions included a prehybridization step in 50% v/v formamide, 1 M NaCl, 10% w/v dextran sulphate, 1% w/v SDS at 42° C. for at least 1 hour. The $^{32}$P-labelled fragments (at $1 \times 10^6$ cpm/mL) were then added to the hybridization solution and hybridization was continued at 42° C. for a further 16 hours. The filters were then washed in 2×SSC, 1% w/v SDS at 42° C. for 2×30 minutes exposed to Kodak XAR film with an intensifying screen at −70° C. for 4 hours.

Twenty colonies (LBAR-AT 1 through 20) were positive and selected for further analysis. Sequence data were generated using the M13 Reverse and M13 Forward −21 primers. The nucleotide sequences generated from LBAR-AT1, 2, 3, 4, 6, 8, 12, 13, 14, 16, 17 and 20 were very similar to that of BPAR-AT2 (pCGP3074) (SEQ ID 14) and BPAR-AT3 (pCGP3075) (SEQ ID NO:16).

Figure 11:
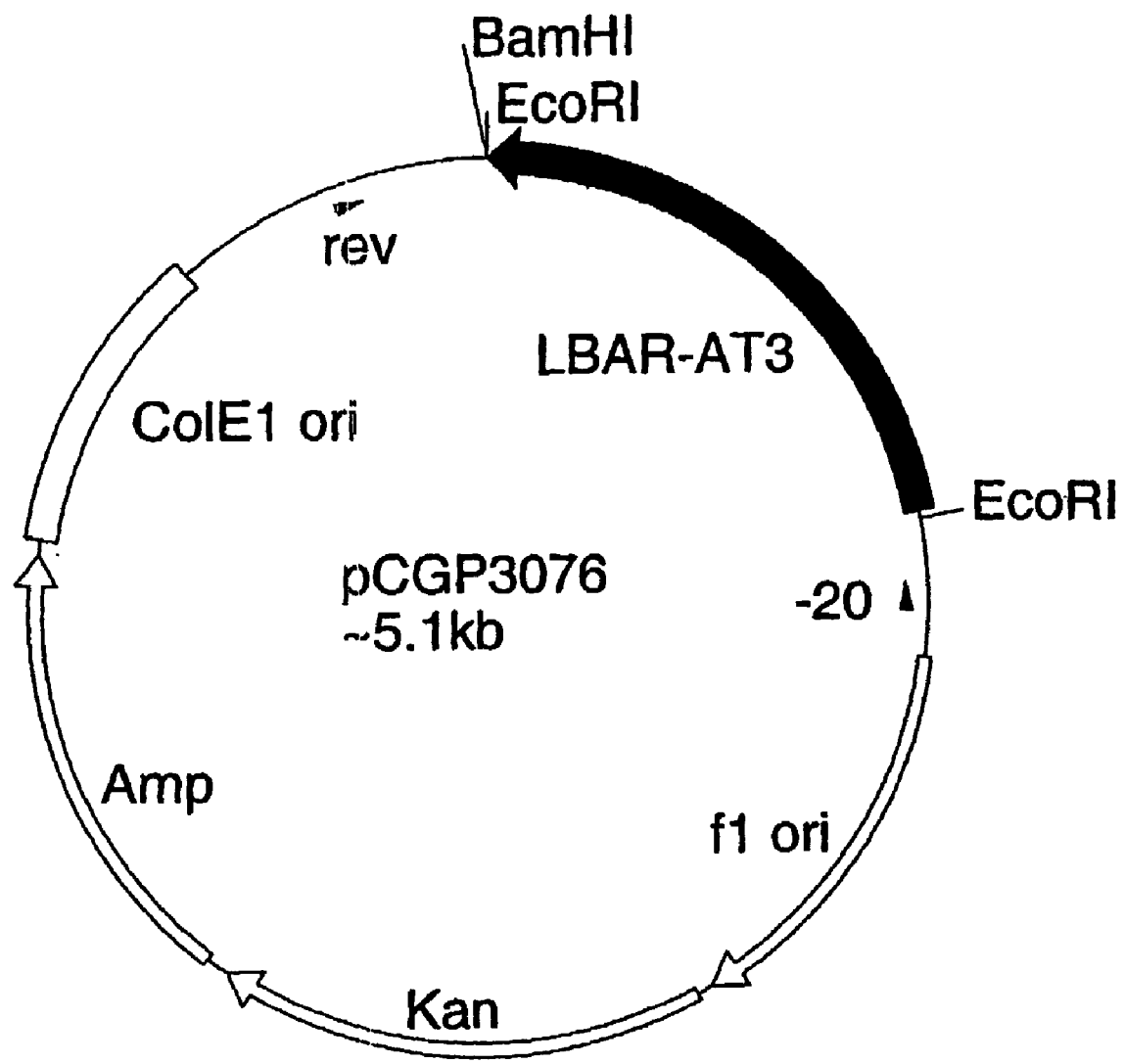
FIG. 11 is a diagrammatic representation of the plasmid pCGP3076 containing the LBAR-AT3 PCR product from *Viola* spp. cv. light blue pansy in a pCR 2.1 vector. Abbreviations are as follows: Amp=the ampicillin resistance gene, Kan=kanamycin resistance gene, fl ori=fl filamentous phage origin of replication, ColE1ori=plasmid origin of replication, rev=approximate location of the M13 reverse primer site used in sequence analysis, −20=approximate location of the M13 −20 primer site used in sequence analysis. A selection of restriction endonuclease recognition sites are also marked.
Figure 12:
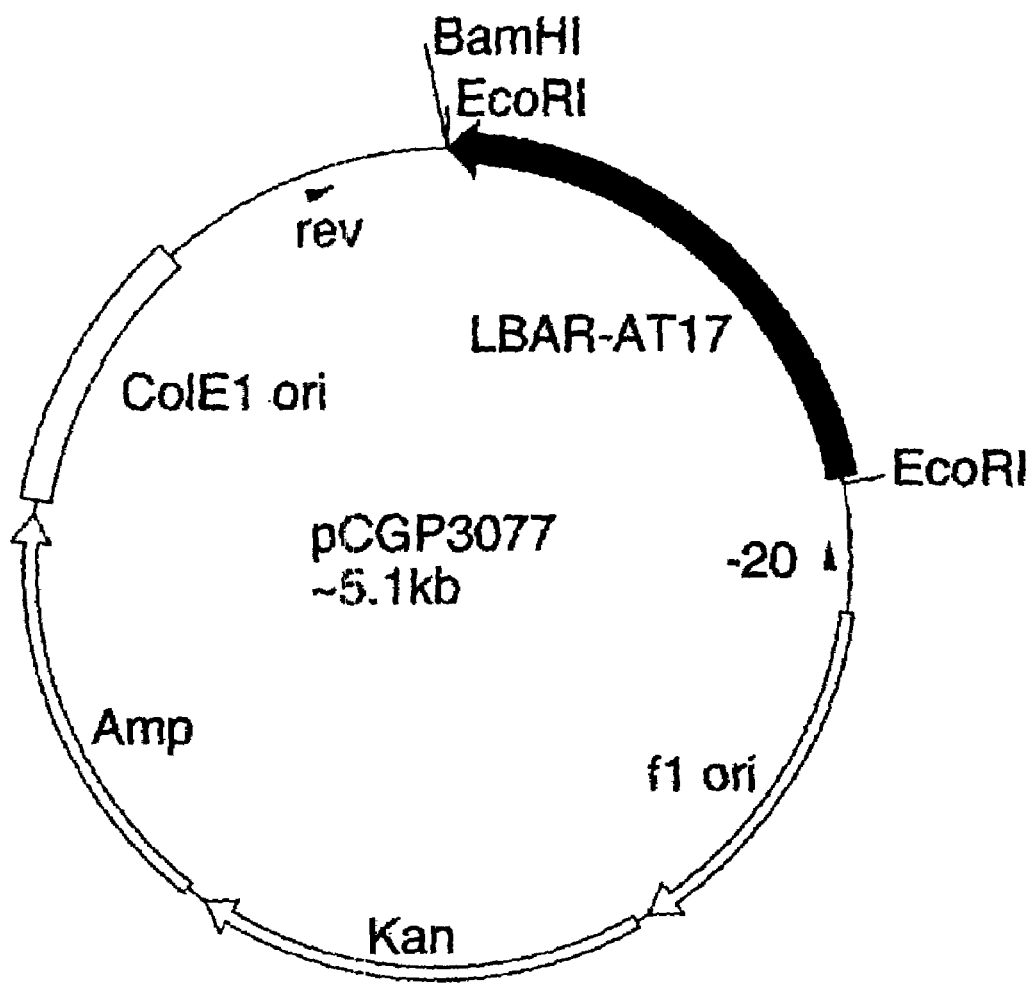
FIG. 12 is a diagrammatic representation of the plasmid pCGP3077 containing the LBAR-AT17 PCR product from *Viola* spp. cv. light blue pansy in a pCR 2.1 vector. Abbreviations are as follows: Amp=the ampicillin resistance gene, Kan=kanamycin resistance gene, fl ori=fl filamentous phage origin of replication, ColE1ori=plasmid origin of replication, rev=approximate location of the M13 reverse primer site used in sequence analysis, −20=approximate location of the M13 −20 primer site used in sequence analysis. A selection of restriction endonuclease recognition sites are also marked.

The LBAR-AT3 and LBAR-AT17 clones, designated pCGP3076 (FIG. 11) and pCGP3077 (FIG. 12) respectively, were selected for further analysis. Complete sequence of the 1.2 kb PCR products of LBAR-AT3 (SEQ ID NO:22) and LBAR-AT17 (SEQ ID NO:24) was generated using primers BPAT2F (SEQ ID NO:18, Table 10) and BPAT3R (SEQ ID NO:21, Table 10).

LBAR-AT3 and 17 shared 97% identity at both the nucleotide and amino acid levels. An LFASTA comparison with BPAR-AT 2 and 3 revealed between 93 to 98% identity at both nucleotide and amino acid levels. An LFASTA alignment between LAR-AT3 (SEQ ID NO:23) and 17 (SEQ ID NO:25) with PAR-AT (SEQ ID NO:2) revealed a 28% identity at the amino acid level (over a 400 amino acid overlap).

EXAMPLE 11

Bootstrapped Phylogenetic Tree of Plant Acyltransferases

Figure 13:
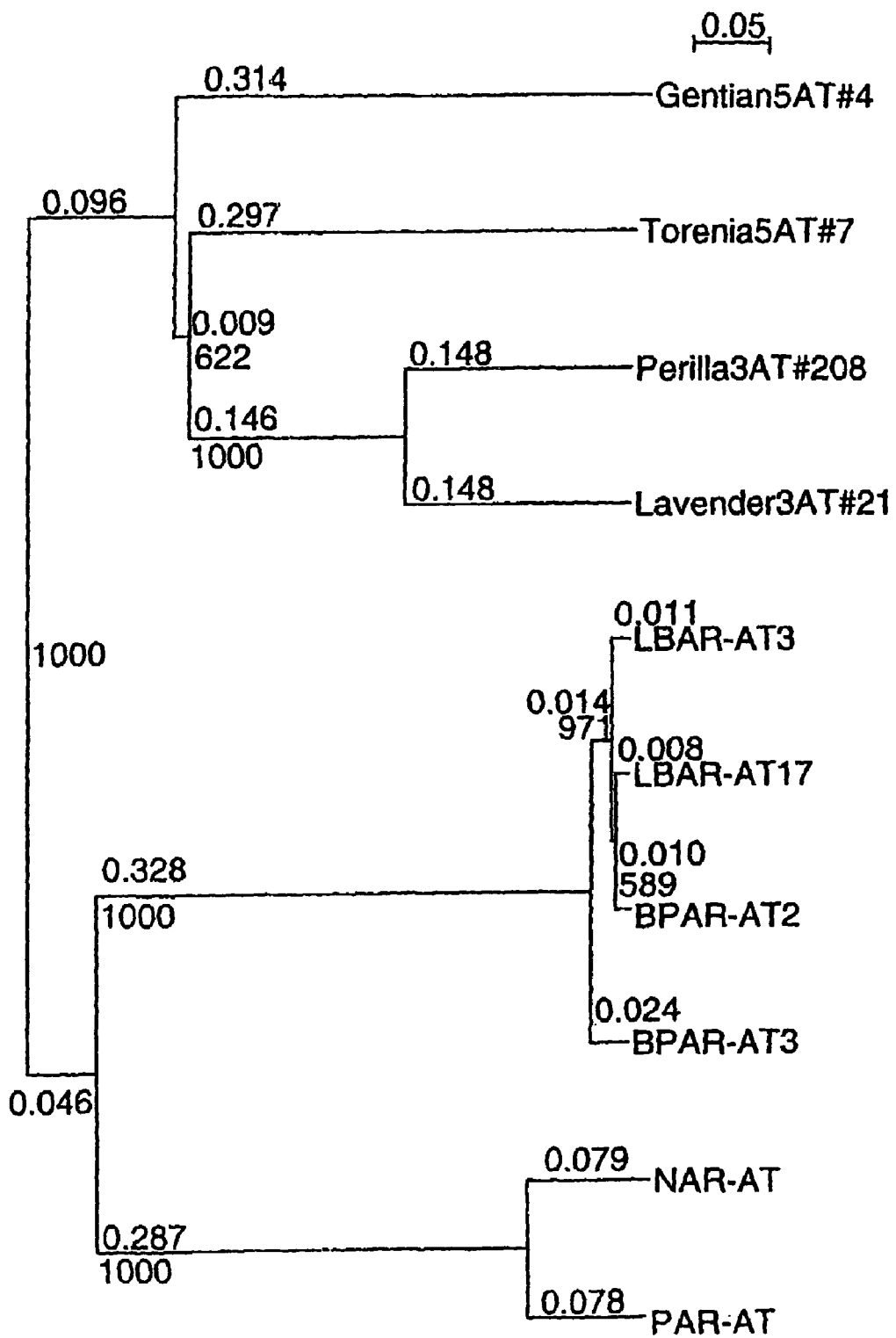
FIG. 13 is a diagrammatic representation showing phylogenetic analysis of selected plant acyltransferases highlighting that the AR-AT sequences disclosed in this specification are in a separate branch compared to the acyltransferases that acylate a glucose attached to an anthocyanidin molecule. The numbers next to the nodes represent bootstrap values from 1,000 replicates.

A phylogenetic tree (with boostrapping) was produced using ClustalW (Thompson et al., 1996) and njplot (mgouy@biomserv.univ-lyon1.fr) respectively (FIG. 13). Deduced amino acid sequences of petunia, nierembergia and pansy AR-AT sequences were aligned with plant acyltransferases shown to aromatically acylate a glucose on the 3' or 5' position of anthocyanins disclosed in International Patent Application No. PCT/JP96/00348 (International Patent Publication No. WO 96/25500).

The use of the phylogenetic tree highlights that BPAR-AT2 and 3 and LBAR-AT3 and 17 segregate into a linked grouping with the petunia AR-AT and nierembergia AR-AT and away from other ATs disclosed in aforementioned Japanese specification (FIG. 13). These data suggest that these clones encode AR-AT enzymes.

EXAMPLE 12

Isolation of Full-length Pansy AR-AT cDNA Clones

Screening of Black Pansy Petal cDNA Library

The deduced amino acid sequences of the BPAR-AT2 (SEQ ID NO:15) and BPAR-AT3 (SEQ ID NO:17) PCR products (and LBAR-AT3 and LBAR-AT17 PCR products) provided compelling evidence to suggest that these clones represent AR-AT sequences. In order to isolate full-length cDNA clones for testing in acyltransferase activity assay systems and use in transgenic plants, a black pansy petal cDNA library was screened.

About 560,000 pfus of the amplified black pansy petal cDNA library were plated onto NZY plates (Sambrook et al., 1989) at a density of 40,000 pfu per 15 cm plate after transfecting XL1-Blue MRF' cells, and incubated at 37° C. for 8 hours. After incubation at 4° C. overnight, duplicate lifts were taken onto Colony/Plaque Screen™ filters (DuPont) and treated as recommended by the manufacturer.

Prior to hybridization, the duplicate plaque lifts were washed in prewashing solution (50 mM Tris-HCl pH 7.5, 1 M NaCl, 1 mM EDTA, 0.1% w/v sarcosine) at 65° C. for 30 minutes; stripped in 0.4 M sodium hydroxide at 65° C. for 30 minutes; then washed in a solution of 0.2 M Tris-HCl pH 8.0, 0.1×SSC, 0.1% w/v SDS at 65° C. for 30 minutes and finally rinsed in 2×SSC, 1.0% w/v SDS.

One set of the duplicate lifts from the black pansy petal cDNA library was screened with $^{32}$P-labelled fragments of a 0.45 kb SacI/EcoRI fragment from pCGP3074 (BPAR-AT 2) FIG. 8) and the second set was screened with $^{32}$P-labelled fragments of a 1.2 kb EcoRI fragment from pCGP3074 (BPAR-AT 2) (FIG. 8).

Hybridization conditions included a prehybridization step in 50% v/v formamide, 1 M NaCl, 10% w/v dextran sulphate, 1% w/v SDS at 42° C. for at least 1 hour. The $^{32}$P-labelled fragments (at 1×10$^6$ cpm/mL) were then added to the hybridization solution and hybridization was continued at 42° C. for a further 16 hours. The filters were then washed in 2×SSC, 1% w/v SDS at 65° C. for 2×30 minutes followed by a wash in 0.2×SSC, 1% w/v SDS at 65° C. for 30 minutes and exposed to Kodak XAR film with an intensifying screen at ¥70° C. for 4 hours and then for 16 hours.

One hundred and seventy-eight pfus strongly hybridized with the probe generated from the 0.45 kb SacI/EcoRI fragment (representing the 5' end of the clone) whilst 357 pfus strongly hybridized with the probe generated from the 1.2 kb EcoRI fragment (representing the whole PCR product).

Thirty pfus that hybridized strongly with both probes were selected to isolate pure clones, using the hybridization conditions as described for the initial screening of the cDNA library. The plasmids contained in the λZAPII bacteriophage vector were rescued and sequence data generated from the 3' and 5' ends of the cDNA inserts using M13 reverse and −20 primers along with specific primers listed in Table 10. The functionality and specificity of the full-length cDNA clones will be ascertained using methods described in Examples 6, 7, 8 and 11.

EXAMPLE 13

Isolation of AR-AT cDNAs From Other Species

Anthocyanidin 3-acylrutinosides are produced in *Viola tricolour* (Goto et al., 1978), *Lobelia erinus* (Kondo et al., 1989), *Eustoma grandiflorum* (Asen et al., 1986) and *Iris ensenta* (Yabuya, 1991). In addition, the presence of anthocyanidin 3-rutinosides has been reported in various plants including *Petunia* (Stafford, 1990; Jonsson et al., 1982; Maizonnier and Moessner, 1980), *Antirrhinum* (Martin et al., 1991), cyclamen (Miyajima et al., 1990), *Metrosideros* (Andersen, 1988), *Alstroemeria* (Saito et al., 1988), *Potentilla* spp. (Harborne and Nash, 1984), *Saintpaulia ionantha* (African violet) (Khokhar et al., 1982), *Bromeliaceae* spp.

(Saito and Harborne, 1983), and geranium (Asen and Griesbach, 1983). It is expected that a number of these plants contain anthocyanidin 3-rutinoside acyl transferases (AR-AT).

The isolation of AR-AT cDNAs from the plants listed above and others is accomplished by the screening of respective cDNA libraries with SEQ ID NO:1, SEQ ID NO:6, SEQ ID NO:14, SEQ ID NO:16, SEQ ID NO:22 or SEQ ID NO:24 using low stringency hybridization conditions such as those described Example 9 or in the introduction of the instant specification.

Alternatively, the isolation of AR-AT cDNA fragments are accomplished using the polymerase chain reaction using CODEHOP primers as listed in Table 8 (Example 10) or degenerate primers as listed in Table 12, below. An example of the primer pair combination that can be used is shown in Table 13, below. The amplification products are cloned into bacterial plasmid vectors and DNA fragments used as probes to screen respective cDNA libraries to isolate longer and full-length AR-AT cDNA clones. The functionality and specificity of the cDNA clones are ascertained using methods described in Examples 6, 7, 8 and 11.

TABLE 12

Degenerate primers designed to areas of amino acid sequence similarity between acyltransferases that act on anthocyanins

| SEQ ID NO: | Name | Sequence (5' to 3') |
|---|---|---|
| 26 | Primer 1f | YTI WSI TTY TTY GA |
| 27 | Primer 3f | GAR GAY CAR AAY YWI TTY GGI AA |
| 28 | Primer 3r | GTT ICC RAA IWR RTT YTG RTC YTC |
| 29 | Primer 4f | GAY TTY GGI TGG GSI AA |
| 30 | Primer 4r | YTT ISC CCA ICC RAA RTC |
| 31 | XhoTTTT | GAGAGAGAGAGAGAGAGAGATCTCCAGTTTTTTT TTTTTTTTTTT | where R=A or G, Y=C or T, M=A or C, K=G or T, S=G or C, W=A or T, H=A or C or T, B=G or C or T, V=A or G or C, D=A or G or T, N=A or G or C or T, I=deoxyinosine.

TABLE 13

Primer pairs that are used in the isolation of other AR-AT cDNA fragments from different plants.

| Forward primer | Reverse primer | Expected fragment (bp) |
|---|---|---|
| SEQ ID NO:24 Primer 1f | SEQ ID NO:26 Primer 3r | ~810 |
| SEQ ID NO:24 Primer 1f | SEQ ID NO:28 Primer 4r | ~1080 |
| SEQ ID NO:24 Primer 1f | SEQ ID NO:31 XhoTTTT | ~1300 |
| SEQ ID NO:25 Primer 3f | SEQ ID NO:28 Primer 4r | ~270 |
| SEQ ID NO:25 Primer 3f | SEQ ID NO:31 XhoTTTT | ~200 |
| SEQ ID NO:27 Primer 4f | SEQ ID NO:31 XhoTTTT | ~470 |
| SEQ ID NO:8: ATf1 | SEQ ID NO:11: ATr3 | ~1140 |
| SEQ ID NO:9: ATf2 | SEQ ID NO:11: ATr3 | ~320 |
| SEQ ID NO:8 ATf1 | SEQ ID NO:12: Dt(17)Ad2Ad1 | ~1280 |
| SEQ ID NO:9: ATf2 | SEQ ID NO:12: dT(17)Ad2Ad1 | ~460 |
| SEQ ID NO:10: ATf3 | SEQ ID NO:12: dT(17)Ad2Ad1 | ~185 |
| SEQ ID NO:13: GI-anchor | SEQ ID NO:11: ATr3 | ~1260 |

Estimations of the expected size of fragment are based on the petunia AR-AT sequence (SEQ ID NO:1). The sizes obtained using RNA as template from different species would be expected to vary.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Altschul et al., *J. Mol. Biol.* 215: 403–410, 1990.
Altschul et al., *Nucl. Acids Res.* 25:3389. 1997.
Ausubel et al., Current Protocols in Molecular Biology, John Wiley & Sons Inc, 1994–1998, Chapter 15.
Andersen, O. M., *Biochem. Syst. Ecol.* 16(6): 535–540, 1988.
Asen, S. and Griesbach, R,. *J. Am. Soc. Hortic. Sci.* 108(5): 845–850, 1983.
Asen et al., *Phytochemistry,* 25(11): 2509–2514, 1986.
Ashikari et al., *Appl. Microbiol. Biotechnol.* 30: 515–520, 1989
Aviv, H. and Leder, P., *Proc. Natl. Acad. Sci. USA* 69: 1408, 1972.
Bethesda Research Laboratories. BRL pUC host: *E. coli* DH5α™ competent cells. *Bethesda Res. Lab. Focus.* 8(2): 9, 1986.
Bonner and Laskey *Eur. J. Biochem.* 46: 83, 1974
Brouillard, R. and Dangles, O., In: *The Flavonoids—Advances in Research since 1986.* Harborne, J. B. (ed), Chapman and Hall, London, UK, 1–22, 1993.
Brugliera, F., Holton, T. A., Stevenson, T. W., Farcy, E., Lu, C-Y and Cornish, E. C. *Plant J.* 5: 81–92, 1994
Brugliera, F., Barri-Rewell, G., Holton, T. and Mason, J. (1999) *Plant J.* 19: 441–451.
Bullock et al., *Biotechniques* 5: 376, 1987.
Comai et al., *Plant Molecular Biology* 15: 373–381, 1990.
Dangles et al., *Phytochemistry* 34: 119–124, 1993.
Doodeman et al., *Theor. Appl. Genet.* 67: 357–366, 1984.
Ebel, J. and Hahlbrock, K., In: *The Flavonoids: Advances in Research Since 1980.* Harbourne, J. B. (ed.), Academic Press, New York, USA, 641–679, 1988.
Fujiwara et al., *Eur. J. Biochem.* 249: 45–51, 1997.
Fujiwara et al, *Plant J.* 16: 421–431, 1998.
Gamborg et al., *Exp. Cell Res.* 50: 151–158, 1968.
Garfinkel et al., *J. Bact.* 144: 732–743, 1980.
Goto, T. and Kondo, T. *Angew. Chem. Int. Ed. Engl.* 30: 1733, 1991
Goto et al., *Tetrahedron* 27: 2413–2416, 1987.
Griesbach et al., *Phytochemistry* 30: 1729–1731, 1991.
Hahlbrock, K. and Grisebach, H., *Annu. Rev. Plant Physiol.* 30: 105–130, 1979.
Hanahan, D., *J. Mol. Biol.* 166: 557, 1983.
Harborne, J. B. and Nash, R. J., *Biochem. Syst. Ecol.* 12(3): 315–318, 1984.
Higgins, D. G. and Sharp, P. M., *Gene* 73: 237–244, 1988.
Holton, T. A., Brugliera, F. Lester, D. R., Tanaka, Y. Hyland, C. D. Menting, J. G. T., Lu, C., Farcy, E., Stevenson, T. W. and Cornish, E. C. *Nature,* 366: 276–279, 1993.
Holton, T. A. and Cornish, E. C. *Plant Cell* 7: 1071–1083, 1995.
Hopp, W. and Seitz, H. U., *Planta* 170: 74–85, 1987.
Inoue et al., *Gene* 96: 23–28, 1990.
Ito etal., *J. Bacteriol.* 153: 163–168, 1983.
Jefferson et al., *EMBO J.* 6(13): 3901–3907, 1987.
Jonsson et al., *Phytochemistry* 21(10): 2457–2460, 1982
Kamsteeg et al. *Biochem Physiol Pflanzen* 175: 403–411, 1980.
Kroon et al., *Plant J* 5: 69–80, 1994.
Khokhar et al., *Hortscience* 17(5): 810–811, 1982.
Kondo et al., *Tetrahedron Letters* 30: 6055, 1989.
Lazo et al., *Bio/technology* 9: 963–967, 1991.
Lu et al., *Phytochemistry,* 31: 289–295, 1992
Maizonnier, D. and Moessner, A., *Genetica* 52(2): 143–148, 1980.
Marmur and Doty, *J. Mol. Biol.* 5:109, 1962.
Martinet al., *The Plant Journal* 1(1): 37–49, 1991.
Merrifield, *J. Am. Chem. Soc.* 85:2149, 1964.
Miyajima et al., *Sci. Bull. Fac. Agric. Kyushu Univ.* 45(1–2): 83–90, 1990.
Murashige, T. and Skoog, F., *Physiol. Plant* 15: 73–97, 1962
Pearson, W. R. and Lipman, D. J., *Proc. Natl. Acad. Sci. USA* 85: 2444–2448, 1988.
Rose et al., *Nucl Acids Res,* 26:1628–1635, 1998.
Saito, N. and Harborne, J. B., *Phytochemistry* 22(8): 1735–1740, 1983.
Saito et al., *Phytochemistry* 27(5): 1399–1402, 1988.
Sambrook et al., *Molecular Cloning: A Laboratory Manual.* (2nd edition), Cold Spring Harbor Laboratory Press, USA, 1989.
Schenk, R. U. and Hilderbrandt, A. C., *Can. J. Bot.* 50: 199–204, 1972.
Schram et al., Biochemistry of flavonoid synthesis in *Petunia hybrida.* In: *Petunia* Sink, K. C. (ed.), Springer-Verlag, Berlin, Germany, pp 68–75, 1984.
Seitz, H. U. and Hinderer, W., Anthocyanins. In: *Cell Culture and Somatic Cell Genetics of Plants.* Constabel, F. and Vasil, I. K. (eds.), Academic Press, New York, USA, 5: 49–76, 1988.
Stafford, H. A., *Flavonoid Metabolism.* CRC Press, Inc. Boca Raton, Fla., USA, 1990.
St-Pierre, B. and De Luca, V. In: *Recent Advances in Phytochemistry-Evolution of Metabolic Pathways.* Pergamon, Oxford, UK 34, 285–316, 2000
Strack, D. and Wray, V. In: *The Flavonoids—Advances in Research since 1986.* Harborne, J. B. (ed), Chapman and Hall, London, UK, 1–22, 1993.
Tanaka et al., *J. Biochem.* 103: 954–961, 1988.
Tanaka et al., *Plant Cell Physiol* 37: 711–716, 1996.
Thompson et al., *Nucl. Acids Res.* 2: 4673–4680. 1994.
Turpen, T. H. and Griffith, O. M., *BioTechniques* 4: 11–15, 1986.
Wallroth et al., *Mol. Gen. Genet.* 202: 6–15, 1986.
Wiering, H. and De Viaming, P., Inheritance and Biochemistry of Pigments. In: *Petunia* Sink, K. C. (ed.), Springer-Verlag, Berlin, Germany, pp 49–65, 1984.
Yabuya, T., *Euphytica* 52: 215–219. 1991.
Yoshida et al., *Tetrahedron* 48: 4313, 1992.

All publications, patents, and patent applications are incorporated by reference herein, as though individually incorporated by reference.

The invention claimed is:

1. An isolated nucleic acid molecule comprising a sequence of nucleotides encoding or complementary to a sequence encoding an anthocyanidin-rutinoside acyltransferase (AR-AT) molecule, said nucleic acid molecule having the nucleotide sequence comprising:
   (i) a nucleotide sequence set forth in SEQ ID NO: 1;
   (ii) a nucleotide sequence having at least 90% sequence identity over the full length of SEQ ID NO: 1;
   (iii) a nucleotide sequence that hybridizes under high stringency conditions to SEQ ID NO: 1 or its complementary form;
   (iv) a nucleotide sequence encoding the amino acid sequence set forth in SEQ ID NO: 2;
   (v) a nucleotide sequence encoding an amino acid sequence having at least about 90% sequence identity over the full length of SEQ ID NO: 2; or
   (vi) a nucleotide sequence that hybridizes under high stringency conditions to the nucleotide sequence in (iv) or (v) or its complementary form;

wherein said nucleotide sequence encodes an AR-AT molecule having AR-AT activity.

2. An isolated nucleic acid molecule according to claim 1 wherein the molecule is of *Petunia* origin.

3. A genetic construct comprising a nucleic acid molecule encoding an AR-AT molecule, wherein said AR-AT molecule comprises:
   (i) a nucleotide sequence set forth in SEQ ID NO: 1;
   (ii) a nucleotide sequence having at least 90% sequence identity over the full length of SEQ ID NO: 1;
   (iii) a nucleotide sequence that hybridizes under high stringency conditions to SEQ ID NO: 1 or its complementary form;

(iv) a nucleotide sequence encoding the amino acid sequence set forth in SEQ ID NO: 2;
(v) a nucleotide sequence encoding an amino acid sequence having at least about 90% sequence identity over the full length of SEQ ID NO: 2; or
(vi) a nucleotide sequence that hybridizes under high stringency conditions to the nucleotide sequence in (iv) or (v) or its complementary form;

wherein said nucleotide sequence encodes an AR-AT molecule having AR-AT activity.

4. A genetic construct according to claim 3 comprising an AR-AT molecule wherein the molecule is of *Petunia* origin.

5. A transgenic plant or plant art thereof or cells therefrom comprising genetic material encoding an AR-AT molecule, wherein said AR-AT molecule comprises:
(i) a nucleotide sequence set forth in SEQ ID NO: 1;
(ii) a nucleotide sequence having at least 90% sequence identity over the full length of SEQ ID NO: 1;
(iii) a nucleotide sequence that hybridizes under high stringency conditions to SEQ ID NO: 1 or its complementary form;
(iv) a nucleotide sequence encoding the amino acid sequence set forth in SEQ ID NO: 2;
(v) a nucleotide sequence encoding an amino acid sequence having at least about 90% sequence identity over the full length of SEQ ID NO: 2; or
(vi) a nucleotide sequence that hybridizes under high stringency conditions to the nucleotide sequence in (iv) or (v) or its complementary form;

wherein said nucleotide sequence encodes an AR-AT molecule having AR-AT activity.

6. A transgenic plant or part thereof or cells therefrom according to claim 5 wherein the molecule is of *Petunia* origin.

7. A transgenic plant or part thereof or cells therefrom according to claim 5 wherein said plant or part thereof or cells therefrom is a cut-flower species.

8. A transgenic plant or part thereof or cells therefrom according to claim 7 wherein said plant or part thereof or cells therefrom is rose, chrysanthemum, tulip, lily, carnation, gerbera, orchid, lisianthus, begonia, torenia, geranium, petunia, nierembergia or *Viola* spp.

9. A transgenic plant or part thereof or cells therefrom according to claim 8 wherein said plant or part thereof or cells therefrom is petunia.

10. A transgenic plant or part thereof or cells therefrom according to claim 5 wherein said plant or part thereof or cells therefrom is an ornamental plant species.

11. A transgenic plant or part thereof or cells therefrom according to claim 5 wherein said plant or part thereof or cells therefrom is an agricultural plant species.

12. A transgenic plant or part thereof or cells therefrom according to claim 5 wherein said plant or part thereof or cells therefrom has altered flower colour compared to a non-transformed plant.

13. Flowers cut or severed from a plant according to claim 5.

14. A method of expressing a nucleotide sequence encoding an AR-AT molecule in a plant or cells of a plant, said method comprising introducing into said plant or cells of said plant a genetic construct wherein said construct comprises a nucleic acid molecule encoding an AR-AT molecule, wherein said AR-AT molecule comprises:
(i) a nucleotide sequence set forth in SEQ ID NO: 1;
(ii) a nucleotide sequence having at least 90% sequence identity over the full length of SEQ ID NO 1;
(iii) a nucleotide sequence that hybridizes under high stringency conditions to SEQ ID NO: 1 or its complementary form;
(iv) a nucleotide sequence encoding the amino acid sequence set forth in SEQ ID NO: 2;
(v) a nucleotide sequence encoding an amino acid sequence having at least about 90% sequence identity over the full length of SEQ ID NO: 2; or
(vi) a nucleotide sequence that hybridizes under high stringency conditions to the nucleotide sequence in (iv) or (v) or its complementary form;

wherein said nucleotide sequence encodes an AR-AT molecule having AR-AT activity.

15. A method of expressing a nucleotide sequence according to claim 14 wherein the molecule is of *Petunia* origin.

16. A transgenic plant or part thereof or cells therefrom according to claim 5 wherein said part is propagation or other reproductive material from said transgenic plant.

17. The transgenic plant or part thereof or cells therefrom according to claim 16 wherein the propagation or other reproductive material is pollen.

18. The transgenic plant or part thereof or cells therefrom according to claim 16 wherein the propagation or other reproductive material is root stock.

19. The transgenic plant or part thereof or cells therefrom according to claim 16 wherein the propagation or other reproductive material is meristem tissue.

20. The transgenic plant or part thereof or cells therefrom according to claim 16 wherein the propagation or other reproductive material is seed.

21. A transgenic plant or part thereof or cells therefrom according to claim 5 wherein said part is a grape.

22. A method for generating a genetically modified plant, said method comprising introducing into cells of said plant a nucleic acid molecule according to claim 1, regenerating a plant from said cells and growing said plants under conditions sufficient for expression of said nucleic acid molecule.

23. A method for generating a genetically modified plant, said method comprising introducing into cells of said plant a genetic construct according to claim 3, regenerating a plant from said cells and growing said plants under conditions sufficient for expression of said genetic construct.

24. A transgenic plant generated by the method of claims 22 or 23.

25. A progeny of the transgenic plant according to claim 24, comprising genetic material encoding an AR-AT molecule wherein said AR-AT molecule comprises:
(i) a nucleotide sequence set forth in SEQ ID NO: 1;
(ii) a nucleotide sequence having at least 90% sequence identity over the full length of SEQ ID NO: 1;
(iii) a nucleotide sequence that hybridizes under high stringency conditions to SEQ ID NO: 1 or its complementary form;
(iv) a nucleotide sequence encoding the amino acid sequence set forth in SEQ ID NO: 2;
(v) a nucleotide sequence encoding an amino acid sequence having at least about 90% sequence identity over the full length of SEQ ID NO: 2; or
(vi) a nucleotide sequence that hybridizes under high stringency conditions to the nucleotide sequence in (iv) or (v) or its complementary form;

wherein said nucleotide sequence encodes an AR-AT molecule having AR-AT activity.

26. A plant part of the plant according to claim 24.
27. A plant part of the plant according to claim 25.

* * * * *

UNITED STATES PATENT AND TRADEMARK OFFICE
CERTIFICATE OF CORRECTION

PATENT NO. : 7,173,164 B2
APPLICATION NO. : 10/259549
DATED : February 6, 2007
INVENTOR(S) : Brugliera et al.

It is certified that error appears in the above-identified patent and that said Letters Patent is hereby corrected as shown below:

In column 4, line 44, delete "nucleofide" and insert -- nucleotide --, therefor.

In column 8, line 32, after "Bells" insert -- . --.

In column 24, line 57, delete "pCGP912" and insert -- pCGP1912 --, therefor.

In column 25, line 42, after "0.1" delete "mg/L" and insert -- g/L --, therefor.

In column 26, line 34, after "Br140" insert -- = --.

In column 26, line 56, delete "minute" and insert -- mL/minute --, therefor.

In column 27, lines 17-21, after "minutes." delete "D3R=delphinidin……………..in minutes.". (Second Occurrence)

In column 29, line 1, delete "pCGP9117" and insert -- pCGP1917 --, therefor.

In column 31, line 29, after "delphinidin" insert -- - --.

In column 36, line 3, delete "(3PAR-AT3)" and insert -- (BPAR-AT3) --, therefor.

In column 37, line 22, delete "FIG. 8)" and insert -- (FIG. 8) --, therefor.

In column 38, line 18, delete "combination" and insert -- combinations --, therefor.

In column 38, line 63, after "NO:8" insert -- : --.

In column 40, line 2, delete "etal.," and insert -- et al., --, therefor.

In column 40, line 18, delete "Martinet" and insert -- Martin et --, therefor.

In column 40, line 59, delete "Viaming," and insert -- Vlaming, --, therefor.

UNITED STATES PATENT AND TRADEMARK OFFICE
CERTIFICATE OF CORRECTION

PATENT NO. : 7,173,164 B2
APPLICATION NO. : 10/259549
DATED : February 6, 2007
INVENTOR(S) : Brugliera et al.

It is certified that error appears in the above-identified patent and that said Letters Patent is hereby corrected as shown below:

In column 71, line 66, in Claim 14, delete "NO" and insert -- NO: --, therefor.

Signed and Sealed this

First Day of July, 2008

JON W. DUDAS
*Director of the United States Patent and Trademark Office*